United States Patent
Nomoto et al.

(10) Patent No.: US 7,186,459 B2
(45) Date of Patent: Mar. 6, 2007

(54) LIPOSOME COATED WITH POLYHYDROXYALKANOATE AND PRODUCTION METHOD THEREOF

(75) Inventors: Tsuyoshi Nomoto, Tokyo (JP); Tetsuya Yano, Kanagawa (JP); Shinya Kozaki, Tokyo (JP); Tsutomu Honma, Kanagawa (JP)

(73) Assignee: Canon Kabushiki Kaisha, Tokyo (JP)

( * ) Notice: Subject to any disclaimer, the term of this patent is extended or adjusted under 35 U.S.C. 154(b) by 376 days.

(21) Appl. No.: 10/190,490

(22) Filed: Jul. 9, 2002

(65) Prior Publication Data

US 2003/0113368 A1   Jun. 19, 2003

(30) Foreign Application Priority Data

Jul. 10, 2001  (JP)  ............................. 2001-210020

(51) Int. Cl.
*B32B 5/16* (2006.01)
*A61K 9/16* (2006.01)

(52) U.S. Cl. .................. 428/403; 424/497; 428/407

(58) Field of Classification Search ........... 428/403, 428/407; 424/450, 463, 490, 497, 498
See application file for complete search history.

(56) References Cited

U.S. PATENT DOCUMENTS

| | | | |
|---|---|---|---|
| 4,744,989 A | 5/1988 | Payne et al. ............... 424/490 |
| 4,873,035 A | 10/1989 | Wong ........................ 264/4.6 |
| 5,064,655 A * | 11/1991 | Uster et al. ................ 424/450 |
| 5,169,636 A * | 12/1992 | Nanba et al. ............... 424/450 |
| 5,393,530 A * | 2/1995 | Schneider et al. .......... 424/450 |
| 5,512,295 A * | 4/1996 | Kornberg et al. ........... 424/450 |
| 5,599,891 A * | 2/1997 | Horowitz et al. ........... 527/202 |
| 5,635,206 A | 6/1997 | Ganter et al. ............... 424/450 |
| 5,820,880 A * | 10/1998 | Alving et al. .............. 424/450 |
| 5,993,374 A * | 11/1999 | Kick .............................. 600/8 |
| 6,004,534 A * | 12/1999 | Langer et al. ............ 424/9.321 |
| 6,022,729 A * | 2/2000 | Steinbuchel et al. ...... 435/252.3 |
| 6,146,665 A * | 11/2000 | Marchessault et al. ...... 424/497 |
| 6,277,413 B1 * | 8/2001 | Sankaram ................... 424/501 |
| 6,410,096 B1 * | 6/2002 | Eggink et al. ............. 427/385.5 |
| 6,492,134 B1 * | 12/2002 | Aquin et al. ................... 435/41 |
| 6,586,658 B1 * | 7/2003 | Peoples et al. ............. 800/281 |
| 6,623,749 B2 * | 9/2003 | Williams et al. ............ 424/423 |
| 2001/0029039 A1 | 10/2001 | Honma et al. .............. 435/135 |
| 2001/0031488 A1 | 10/2001 | Imamura et al. ............ 435/135 |
| 2002/0052444 A1 | 5/2002 | Imamura et al. ............ 525/107 |
| 2004/0234576 A1 * | 11/2004 | Martin et al. ............... 424/426 |

FOREIGN PATENT DOCUMENTS

JP    52-114013    9/1977

(Continued)

OTHER PUBLICATIONS

Shishatskaya, "Tissue response to the implantation of biodegradable polyhydroxyalkanoate sutures", J. of Mat'l. Sci.: Materials in Medicine, Jun. 2004.*

(Continued)

*Primary Examiner*—H. Thi Le
(74) *Attorney, Agent, or Firm*—Fitzpatrick, Cella, Harper & Scinto

(57) ABSTRACT

A structure, which has both a drug holding capability and a sustained release ability utilizing a liposome and mechanical strength of a polyhydroxyalkanoate. This structure is excellent in holding capability for hydrophilic drugs and other water-soluble substances, as well as lipophilic drugs and other hydrophobic substances, and is capable of controlling the sustained release ability. The polyhydroxyalkanoate coats at least a part of the outer wall of the liposome.

22 Claims, 5 Drawing Sheets

FOREIGN PATENT DOCUMENTS

| | | |
|---|---|---|
| JP | 59-173133 | 10/1984 |
| JP | 2-139029 | 5/1990 |
| JP | 6-178930 | 6/1994 |
| JP | 6-298638 | 10/1994 |
| JP | 7-241487 | 9/1995 |
| JP | 2001-69968 | 3/2001 |
| JP | 2001-78753 | 3/2001 |

OTHER PUBLICATIONS

Volova et al., "A comparative investigation of biodegradable polyhydroxyalkanoate films as matrices for in vitro cell cultures", J. of Mat. Science: Materials in Medicine, Aug. 2004.*

Alexander Steinbüchel et al., "Diversity of Bacterial Polyhydroxyalcanoic Acids," 128 *FEMS Microbiol. Lett.* 219-228 (1995).

European Search Report in Application No. 02015375.5 (Apr. 17, 2003).

Junzo Sunamoto et al., "Liposomal Membranes. VII. Fusion and Aggregation of Egg Lecithin Liposomes as Promoted by Polysaccharides," 94(4) *Biochem. Biophys. Res. Comm.* 1367-1373 (1980).

Shmuel Batzri et al., "Interaction of Phospholipid Vesicles with Cells: Endocytosis and Fusion as Alternate Mechanisms for the Uptake of Lipid-Soluble and Water-Soluble Molecules," 66 *J. Cell Biol.* 621-634 (1975).

Y. Barenholzt et al., "A New Method for Preparation of Phospholipid Vesicles (Liposomes)—French Press," 99(1) *FEBS Lett.* 210-214 (1979).

David W. Deamer, "Preparation and Properties of Ether-Injection Liposomes," 308 *N.Y. Acad. Sci.* 250-258 (1978).

J. Brunner et al., "Single Bilayer Vesicles Prepared Without Sonication: Physico-Chemical Properties,"455 *Biochim. Biophys. Acta* 322-331 (1976).

D. Papahadjopoulos et al., "Cochleate Lipid Cylinders: Formation by Fusion of Unilamellar Lipid Vesicles," 394 *Biochim. Biophys. Acta* 483-491 (1975).

Francis Szoka, Jr., et al., "Procedure for Preparation of Liposomes with Large Internal Aqueous Space and High Capture by Reverse-Phase Evaporation," 75(9) *Proc. Natl. Acad. Sci. USA* 4194-4198 (1978).

Uri Pick, "Liposomes with a Large Trapping Capacity Prepared by Freezing and Thawing of Sonicated Phospholipid Mixtures," 212(1) *Archives Biochem. Biophys.* 186-194 (1981).

T.U. Gerngross et al., "Enzyme-Catalyzed Synthesis of Poly[(R)-(-)-3-Hydroxybutyrate]: Formation of Macroscopic Granules *in vitro*," 92 *Proc. Natl. Acad. Sci. USA* 6279-6283 (1995).

Tomoyasu Kichise et al., "Biosynthesis of Polyhydroxyalkanoates (PHA) by Recombinant *Ralstonia eutropha* and Effects of PHA Synthase Activity on *in vitro* PHA Biosynthesis," 25 *Int. J. Biol. Macromol.* 69-77 (1999).

Geoffrey A.R. Nobes et al., "Growth and Kinetics of *in vitro* Poly([R]-(-)-3-Hydroxybutyrate Granules Interpreted as Particulate Polymerization with Coalescence," 21 (2) *Rapid Macromol. Comm.* 77-84 (2000).

Ralf Jossek et al., "*In vitro* Synthesis of Poly(3-Hydroxybutyric Acid) by Using an Enzymatic Coenzyme A Recycling System," 168 *FEMS Microbiol. Lett.* 319-324 (1998).

Q. Qi et al., "*In vitro* Synthesis of Poly(3-Hydroxydecanoate): Purification and Enzymatic Characterization of Type II Polyhydroxyalkanoate Synthase PhaC1 and PhaC2 from *Pseudomonas aeruginosa*," 54 *Appl. Microbiol. Biotechnol.* 37-43 (2000).

Henry J. Vogel et al., "Acetylornithinase of *Escherichia coli*: Partial Purification and Some Properties," *J. Biol. Chem.* 97-108 (1956).

John L. Speier et al., "The Addition of Silicon Hydrides to Olefinic Double Bonds. Part I. The Use of Phenylsilane, Diphenylsilane, Phenylmethylsilane, Amylsilane and Tribromosilane," 78 *J. Amer. Chem. Soc.* 2278-2281(1956).

Molecular Cloning: A Laboratory Manual, $2^{nd}$ ed., § 5.72 (1989).

Marjan Nienke Kraak et al., "*In vitro* Activities of Granule-Bound Poly[(R)-3-Hydroxyalkanoate] Polymerase C1 of *Pseudomonas oleovorans*: Development of an Activity Test for Medium-Chain-Length-Poly(3-Hydroxydecanoate) Polymerases," 250 *Eur. J. Biochem.* 432-439 (1997).

Dale A. Pelletier et al., "2-Hydroxycyclohexanecarboxyl Coenzyme A Dehydrogenase, an Enzyme Characteristic of the Anaerobic Benzoate Degradation Pathway Used by *Rhodopseudomonas palustris*" 182 (10) *J. Bacteriol.* 2753-2760 (2000).

Katharina Fritzsche et al., "Production of Unsaturated Polyesters by *Pseudomonas oleovorans*," 12 *Int. J. Macromol.* 85-91 (1990).

Bernd H.A. Rehm et al., "A New Metabolic Link Between Fatty Acid *de Novo* Synthesis and Polyhydroxyalkanoic Acid Synthesis," 273(37) *J. Biol. Chem.* 24044-24051 (1998).

A.D. Bangham et al., "Diffusion of Univalent Ions Across the Lamellae of Swollen Phospholipids," 13 *J. Mol. Biol.* 238-252 (1965).

* cited by examiner

LIPOSOME COATED WITH POLYHYDROXYALKANOATE AND PRODUCTION METHOD THEREOF

BACKGROUND OF THE INVENTION

1. Field of the Invention

The present invention relates to an excellently biocompatibile polyhydroxyalkanoate-coated liposome having a highly stable membrane, with sustained releasability of a substance encapsulated thereon being controlled, and a production method thereof.

2. Related Background Art

Liposome, which is formed when a lipid is dispersed in water, is of extremely close proximity to cell membrane structure as a model and is expected to be aggressively utilized as a medicinal substance such as a tissue-oriented drug delivery agent, artificial erythrocyte, a cell restoration agent, or an enzyme fixation base. In addition, not only in the fields of medicine and pharmacy, but also in the area of cosmetics, it is expected as a substance that selectively transports effective components having a problem in stability to an affected part and controls gradual releasability. Liposome finds an extremely wide range of applications as mentioned above, but its fragility in membrane structure has been pointed out. In other words, chemical or physical changes of a lipid, a membrane forming substance, destroy the membrane, readily causing leakage of a substance contained and drug delivery to target cells has not been sufficiently improved. Conventionally, methods of reinforcing liposome membranes are known that include a method for providing the membrane with hydrogen bonding by adding sphingomyelin thereto and reinforcing the membrane, and a method of preventing oxidation of unsaturated lipid by adding tocopherol, etc.

Furthermore, liposome with a highly stable liposome membrane and a production method thereof have been needed in order to stabilize a liposome membrane and achieve excellent drug holding therein and gradual releasability of a drug at a target cell.

Conventionally, to enhance the mechanical strength of liposome under physiological conditions and enable the membrane to control gradual releasability of a drug, Japanese Patent Application Laid-Open No. 06-178930 has proposed a liposome membrane formed by coating the surface of the membrane with a homopolymer of 2-methacryloyloxyethyl phosphorylcholine or with a copolymer of 2-methacryloyloxyethyl phosphorylcholine and a monomer.

Further, Japanese Patent Application Laid-Open No. 06-298638 has proposed liposome coated with a sterol and/or a sterol glucoside, including sitosterol, campesterol, stigmasterol, or brassicasterol.

On the other hand, as an example of formation of a capsule containing a drug therein using polyhydroxyalkanoate as a biodegradable and biocompatible substance other than phospholipid, U.S. Pat. No. 6,146,665 has disclosed a process for preparing a drug composition composed of a fine particle that has entrapped a hydrophilic drug in a porous granule made of polyhydroxyalkanoate, or a drug composition that encapsulates as the core substance an oil droplet in which a lipophilic drug is dissolved in a shell composed of polyhydroxyalkanoate.

However, the liposome formed by coating of homopolymer of 2-methacryloyloxyethyl phosphorylcholine (MPC) or of copolymer of 2-methacryloyloxyethyl phosphorylcholine and a monomer, as disclosed in Japanese Patent Application Laid-Open No. 06-178930, is definitely improved in mechanical strength, but is neither necessarily sufficient in strength nor excellent in biocompatibility.

In addition, the fine particle that entraps a hydrophilic drug in a porous granule made of polyhydroxyalkanoate, as disclosed in U.S. Pat. No. 6,146,665, is not poisonous, has biodegradability and is capable of entrapping a drug in situ; however, it allows the hydrophilic drug to immediately disperse due to its porous structure, resulting in difficulty in control of gradual releasability.

SUMMARY OF THE INVENTION

Taking into account the problems of the prior art described above, an object of the present invention is to provide a structure that has both the drug holding capacity and sustained drug releasability of liposome and the mechanical strength of polyhydroxyalkanoate, is excellent in holding properties for hydrophilic drugs and other water-soluble substances, and lipophilic drugs and other hydrophobic substances, and can control gradual releasability.

To achieve the aforementioned object, the present invention provides a polyhydroxyalkanoate-coated liposome that feasures the fact that at least a part of the exterior wall is coated with polyhydroxyalkanoate.

A liposome in the present invention refers to a single-layer liposome or a multi-layer liposome that is comprised of lipid, particularly phospholipid alone, or both phospholipid and sterol, and can be prepared using conventionally well-known methods as its preparation process.

A substance encapsulated in the liposome may be either a water-soluble substance or a fat-soluble substance. Note that a water-soluble material is kept in the inside of liposome and a fat-soluble material in the membrane of liposome. Additionally, these substances are also adsorbed chemically or physically on the membrane surface of liposome. The aforementioned three cases in this invention, i.e., "holding; keeping in the inside," "holding; keeping in the membrane," and "holding; adsorbing on the membrane surface" are all defined as "encapsulating." These substances held by the liposome in the present invention are not particularly limited and include markers, plasmid, DNA and RNA, if the material is effective when it is administered in the living body besides unstable materials in vitro or in vivo and drugs expected to be gradually released in the body or immediately distributed in a specific organ.

The present inventors have found out the fact that a liposome can be coated with polyhydroxyalkanoate by immobilizing a polyhydroxyalkanoate synthesizing enzyme (hereinafter referred to as "polyhydroxyalkanoate synthase" or "PHA synthase") to a liposome membrane, adding 3-hydroxyacyl coenzyme A and allowing it to react, the fact that in the above case, the exterior surface of the liposome can be coated with polyhydroxyalkanoate having biodegradability and no toxicity as a result of selecting a suitable kind of 3-hydroxyacyl coenzyme A therefor, and further the fact that the properties of increased physical and mechanical strength and controllableness of sustained releasability of an enclosed substance can be imparted to the liposome by coating at least part of the membrane of the liposome with polyhydroxyalkanoate. Thereby the present invention has been completed.

The polyhydroxyalkanoate-coated liposome of the present invention has a characteristic of at least part of the exterior wall being coated with polyhydroxyalkanoate. Furthermore, the polyhydroxyalkanoate-coated liposome of the present invention features a structure with a shell being a lipid bimolecular membrane of a phospholipid in which structure at least a part of the exterior wall is coated with polyhydroxyalkanoate.

In addition, the polyhydroxyalkanoate-coated liposome according to the present invention has a characteristic of enclosing substances other than lipid inside the liposome.

The method for preparing a polyhydroxyalkanoate-coated liposome of the present invention at least a part of the exterior wall of which liposome is coated with polyhydroxyalkanoate, comprises the steps of immobilizing a polyhydroxyalkanoate synthase on the surface of the liposome dispersed in the aqueous medium, adding 3-hydroxyacyl CoA as a substrate, and coating at least a part of the surface of the liposome with polyhydroxyalkanoate by the synthesis of the polyhydroxyalkanoate.

The liposome in the present invention has a structure in which at least a part of the surface of the liposome is coated with polyhydroxyalkanoate, and all the surface does not necessarily need to be coated so far as a target property of the liposome is obtained. In the structure regarding the present invention, the coating of the whole surface enables a polyhydroxyalkanoate-coated microcapsule with a liquid as the core to be obtained where the coating layer of polyhydroxyalkanoate is comprised in the shell.

The PHA-coated liposome of the present invention is excellent in biocompatibility, has a highly stable membrane, and can control the sustained releasability of an encapsulated substance. The PHA-coated liposome of the present invention can be utilized for a variety of applications such as pigment-enclosed liposome, dye-enclosed liposome, agricultural chemical-enclosed liposome, hemoglobin-enclosed liposome, cosmetic ingredient-enclosed liposome, fertilizer component-enclosed liposome and pharmaceutical component-enclosed liposome.

The above and other objects, effects, features and advantages of the present invention will become more apparent from the following description of embodiments thereof taken in conjunction with the accompanying drawings.

DESCRIPTION OF THE PREFERRED EMBODIMENTS

Figure 1A:
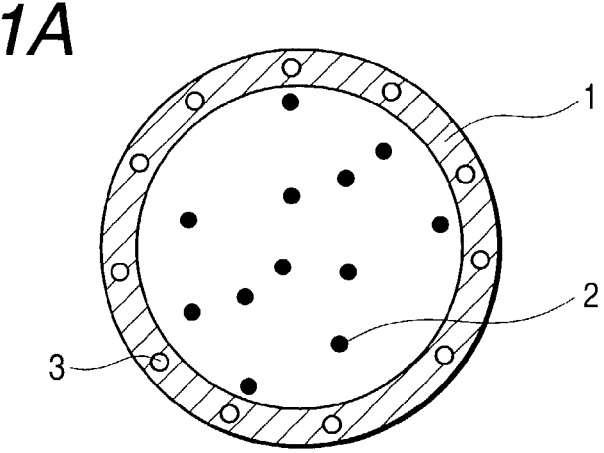
FIGS. 1A, 1B and 1C are flow charts of an example of a method for preparing the PHA-coated liposome of the present invention.

The present invention will be described more in detail hereinafter.

Liposome prior to being coated with polyhydroxyalkanoate for the polyhydroxyalkanoate-coated liposome of the present invention, can be prepared by a conventional production method generally known as a method for preparing liposome. This is, phospholipids to be used in the invention include phosphatidylcholine (PC), phosphatidylethanolamine (PE), phosphatidylserine (PS), phosphatidic acid (PA), phosphatidylinositol (PI) and sphingomyelin (SPN); a single species or a combination of a plurality of species can be utilized. The phospholipids can also include a water-added phospholipid and an enzyme-treated phospholipid. The phospholipids may be synthesized, obtained from natural substances such as eggs and soybeans, or commercially available.

A cholesterol and a phospholipid can be combined in order to produce the hardness and transparency of a lipid bimolecular membrane of the liposome. While the ratio of cholesterol to phospholipid to be used can be varied dependent on the lipid affinity of a substance enclosed, the molar ratio of cholesterol: phospholipid can be illustrated to be from 1:3 to 1:1. A liposome with the shell of a lipid bimolecular membrane made of phospholipid can be prepared by a conventional production method generally known as a production method of liposome. Such, well known techniques include the method of Bangham et al. (Journal of Molecular Biology (J. Mol. Biol.), 13, 238 (1965)), its variation (Japanese Patent Application Laid-Open Nos. 52-114013, 59-173133, 2-139029 and 7-241487), the ultrasonication method (Biochemical and Biophysical Research Communication (Biochem. Biophys. Res. Commun., 94, 1367 (1980)), the ethanol injection method (Journal of Cell Biology (J. Cell. Biol.), 66, 621 (1975)), the French press method (Febs Letters (FEBS Lett.), 99, 210 (1979)), the ether injection method (New York Academy Science (N.Y. Acad. Sci., 308, 250 (1978)), the cholic acid (surfactant) method (Biochimica et Biophysica Acta (Biochim. Biophys. Acta, 455, 322 (1976)), the calcium fusion method (Biochimica et Biophysica Acta (Biochim. Biophys. Acta, 394, 483 (1978)), the freezing and thawing method (Archive of Biochemistry and Biophysics (Arch. Biochem. Biophys.), 212, 186 (1981)), the reverse phase evaporation method (Proceedings of the Natural Academy of Sciences U.S.A. (Pro. N.A.S. USA, 75, 4194 (1978)), a method by means of glass filter (Third US-Japan Symposium on Drug Delivery System (1995)), and a method using a commercial kid such as coatsome. Liposome prepared by these well known methods can be all supplied to the present invention.

The method of producing liposome reported by Bangham et al. involves dissolving a phospholipid in an organic solvent such as chloroform; placing the resulting solution in an eggplant shape flask; removing under vacuum the solvent using a rotary evaporator, thereby forming a phospholipid thin film on the surface of the glass wall in the bottom of the flask. An aqueous buffer solution containing a substance to be encapsulated is add to the resultant with agitation, allowing the film to swell; and then the thin film is mechanically peeled by means of a voltex or the like to yield multi-membrane liposome. The swelling needs to be carried out at the temperature higher by 10° C. than the phase transition temperature of a phospholipid. Multi-membrane liposome prepared by this method has a size distribution of 0.2 to 5 µm. When the distribution is required to be as small as possible, agitation may be conducted vigorously and for a long while, or the liposome may be irradiated with a supersonic wave with a low power of 5 to 10 W for a short time.

The method for preparing liposome by ultrasonication includes further irradiating the suspension of the multi-membrane liposome prepared by the method of Bangham et al. with a high-power supersonic wave. Supersonic wave irradiation makes the size smaller gradually and yields small one-membrane liposomes with a diameter of 20 to 30 nm eventually. Supersonic wave irradiation tends to cause chemical decomposition of phospholipid molecules or oxidation of a lipid by dissolved oxygen, and thus needs to be operated in an inert gas flow of nitrogen, argon or the like and not to excessively increase temperature.

The method for preparing liposome by the ethanol injection method involves dissolving a lipid in ethanol and injecting the resulting solution into a aqueous buffer solution containing a substance to be encapsulated using a microsyringe at the phase transition temperature or higher. Liposome to be prepared is a small one-membrane liposome. Its size varies with the concentration of a lipid. Liposome with a diameter of about 30 nm is obtained in a low lipid concentration (3 mM) and liposome of about 110 nm in a high lipid concentration (36 mM). This method does not entail ultrasonication and thus is suitable for encapsulating an unstable substance. However, the liposome is diluted, and so a concentrating operation such as by ultrafiltration is required in some cases. Further, it has a disadvantage of the ethanol not being removed completely from the liposome.

The method for preparing liposome by the French press method comprises placing in a French press cell the multi-membrane liposome prepared by the method of Bangham et al., extruding the liposome at a pressure of about 20,000 psi to form one-membrane liposome and repeating this operation, thereby yielding a small one-membrane liposome with a diameter of about 30 to 50 nm. This method does not include ultrasonication and thus is suitable for encapsulating an unstable substance. Further, the application of a low pressure forms a one-membrane liposome with a diameter of about 50 to 150 nm.

The method for preparing liposome by the ether injection method includes dissolving a phospholipid in diethyl ether or in a mixture solvent of diethyl ether and methanol, introducing the resultant solution into an aqueous buffer solution containing a substance to be encapsulated, and removing the solvent. The organic solvent is removed by heating the aqueous solution from 55 to 65° C., or keeping it at 30° C. under diminished pressure. The ether injection method can produce a large one-membrane liposome.

The method for preparing liposome by the cholic acid (surfactant) method involves admixing a lipid membrane or multi-membrane liposome prepared by the method of Bangham et al. or a small one-membrane liposome prepared by another method with a surfactant such as cholic acid or deoxycholic acid, and removing the surfactant from mixture, thereby preparing a relatively large size of a one-membrane liposome (30 to 180 nm). Dialysis or gel filtration can be used to remove the surfactant. The size of formed liposome depends on the ratio of lipid to surfactant, the content of cholesterol, the rate of dialysis, etc. In this method, how to make lower the removing ratio of the surfactant in the bilayer of liposome is significant. Accordingly, long-time dialysis or several times repetition of gel filtration is required.

The method for preparing liposome by the calcium fusion method involves addition of calcium ions to liposome prepared by another method containing an acidic phospholipid to induce the fusion of the membrane, and subsequently adding a chelating reagent such as EDTA to remove the calcium, whereby yielding a large one-membrane liposome (200 to 1,000 nm). This method is limited to acidic phospholipids such as phosphatidylserine (PS) and phosphatidic acid (PA) and mixed liposome thereof.

The method for preparing liposome by the freezing and thawing method includes freezing a liposome solution treated by ultrasonication by liquid nitrogen, thawing the solution by allowing it to stand at about room temperature, and subsequently treating the resulting milk white suspension by ultrasonication for a short time. A large one-membrane liposome with a diameter of 50 to 500 nm is prepared. The method has an advantage of the holding efficiency being improved due to a concentration effect during freezing.

The method for preparing liposome by the reverse phase evaporation method includes adding water to an etheric solution of phospholipic and treating by ultrasonication to form a w/o emulsion, removing ether and shaking the emulsion by boltex to result in the inversion of the phase, and further removing the ether under diminished pressure, thereby yielding a large one-membrane liposome (200 to 1,000 nm).

The size of the liposome is affected by the composition of the lipid and the ionic strength of the aqueous solution; addition of cholesterol increases the size and increase of the ionic strength decreases the size. Substances encapsulated in the aforementioned liposomes are appropriately selected depending on the application of the polyhydroxyalkanoate-coated liposome of the present invention.

The polyhydroxyalkanoate-coated liposome of the present invention preferably encloses a substance within the liposome exclusive of a lipid.

Where the polyhydroxyalkanoate-coated liposome of the present invention is used, for example, as liposome for agricultural chemical compositions, any substance if listed in the Agricultural Chemicals Handbook (published by Japan Plant Disease Prevention Association), can be utilized as a substance encapsulated in liposome. Illustrative examples include carbamate-based insecticides, organic phosphorus-based insecticides, pyresteroid-based insecticides, urea-based insecticides, anilide-based insecticides, azole-based insecticides, and dicarboxylimide-based insecticides. These chemicals can be used in a combination of two species or more, as necessary. Liposome encapsulating an agricultural-chemical active component can be prepared by the aforementioned methods such as the ultrasonication method, the ethanol injection method, the French press method, the ether injection method, the cholic acid (surfactant) method, the calcium fusion method, the freezing and thawing method, the reverse phase evaporation method, the method using a glass filter, and the method using a commercially available kit such as coatsome.

Where the polyhydroxyalkanoate-coated liposome of the present invention is used, for example, as liposome for a fertilizer composition, substances encapsulated in the liposome include an aqueous solution of a nitrogen fertilizer such as ammonium sulfate, ammonium chloride, ammonium nitrate, urea, acetaldehyde-condensed urea, or isobutylaldehyde-condensed urea; an aqueous solution of a phosphoric acid fertilizer such as superphosphate of lime, double superphosphate of lime, or fused phosphate fertilizer; an aqueous solution of a potassium-based fertilizer such as potassium sulfate or potassium chloride; an aqueous suspention of an organic fertilizer such as fish meal, bone powder, soybean seedcake, or rape seed cake; an aqueous solution of a three-element-based composite fertilizer such as ammonium phosphate or potassium phosphate; and an aqueous solution of trace element composite fertilizer. These chemicals can be used in a combination of two species or more, as necessary. Such liposomes encapsulating a fertilizer component can be prepared by the aforementioned methods such as the ultrasonication method, the ethanol injection method, the French press method, the ether injection method, the cholic acid (surfactant) method, the calcium fusion method, the freezing and thawing method, the reverse phase evaporation method, a method using a glass filter, and a method using a commercially available kit such as coatsome.

Where the polyhydroxyalkanoate-coated liposome of the present invention is used, for example, as liposome for a cosmetic, substances encapsulated in the liposome include a moisture-keeping component; a raw drug extract; an enzyme such as tyrosinase, superoxide dismutase and lipase; a vitamin such as retinol, ascorbic acid, tocophenol, pyridoxal and riboflavin; an organic pigment such as β-carotene and chlorophyll; a moisture component such as glycerin, sorbitol, urea, lactic acid, propylene glycol, polyethylene glycol or its copolymer and a glycol derivative; an emollient component such as paraffin, stearyl alcohol, cetyl alcohol, squalane, silicone oil and stearin; a treatment component; a dandruff-restraining component; a hear tonic; a hair restoration component; a ultraviolet absorber; an antioxidant; and a perfume. These chemicals can be used in a combination of two species or more, as necessary. Liposome encapsulating a cosmetic component can be prepared by the aforementioned methods such as the ultrasonication method, the ethanol injection method, the French press method, the ether injection method, the cholic acid (surfactant) method, the calcium fusion method, the freezing and thawing method, the reverse phase evaporation method, the method using a glass filter, and the method using a commercially available kit such as coatsome.

Where the polyhydroxyalkanoate-coated liposome of the present invention is used, for example, as liposome for artificial erythrocyte, substances encapsulated in the liposome include hemoglobin and hemocyanin. These substances can be used in a combination of two species or more, as necessary. Liposome encapsulating hemoglobin can be prepared by the aforementioned methods such as the ultrasonication method, the ethanol injection method, the French press method, the ether injection method, the cholic acid (surfactant) method, the calcium fusion method, the freezing and thawing method, the reverse phase evaporation method, the method using a glass filter, and the method using a commercially available kit such as coatsome.

Where the polyhydroxyalkanoate-coated liposome of the present invention is used, for example, as liposome for ink or paint, substances encapsulated in the liposome include an aqueous dye solution and a pigment dispersion, and more particularly include an acidic dye such as C.I. Acid Red 52, C.I. Acid Blue 1, C.I. Acid Black 2, and C.I. Acid Black 123; a basic dye such as C.I. Basic Blue 7 and C.I. Basic Red 1; a direct dye such as C.I. Direct Black 19 and C.I. Direct Blue 86; an oil-soluble dye such as C.I. Solvent Black 7, C.I. Solvent Black 123, C.I. Solvent Red 8, C.I. Solvent Red 49, C.I. Solvent Red 100, C.I. Solvent Blue 2, C.I. Solvent Blue 25, C.I. Solvent Blue 55, C.I. Solvent Blue 70, C.I. Solvent Green 3, C.I. Solvent Yellow 21, C.I. Solvent Yellow 61, C.I. Solvent Orange 37, C.I. Solvent Violet 8 and C.I. Solvent Violet 21; a reactive dye such as C.I. Reactive Yellow 15, C.I. Reactive Yellow 42, C.I. Reactive Red 24, C.I. Reactive Red 218, C.I. Reactive Blue 38 and C.I. Reactive Blue 220; a black pigment such as Carbon Black, copper oxide, manganese dioxide, Aniline Black, activated carbon, non-magnetic ferrite and magnetite; a yellow pigment such as Chrome Yellow, Zinc Yellow, Yellow Oxide, Cadmium Yellow, Mineral Fast Yellow, Nickel Titanium Yellow, Neburs Yellow, Naphthol Yellow S, Hanzar Yellow G, Hanzar Yellow 10G, Benzidine Yellow G, Benzidine Yellow GR, Quinoline Yellow Lake, Permanent Yellow NCG; and Turtladine Lake; an orange pigment such as Red Chrome, Molybdenum Orange, Permanent Orange GTR, Pyrazolone Orange, Vulcan Orange, Benzidine Orange G, Indanthrene Brilliant Orange RK and Indanthrene Brilliant Orange GK; a red pigment such as Red Iron Oxide, Cadmium Red Lead, mercury sulfate, cadmium, Permanent Red 4R, Lithol Red, Pyrazolone Red, Watching red, calcium salt, Lake Red C, Lake Red D, Brilliant Carmin 6B, Brilliant Carmin 3B, Eoxine Lake, Rhodamine Lake B and Alizarin Lake; a blue pigment such as Milori Blue, Cobalt Blue, Alkali Blue Lake, Victoria Blue Lake, Phthalocyanine Blue, Non-metal Phthalocyanine Blue, partly chloride Phthalocyanine Blue, Fast Sky Blue and Indanthrene Blue BC; a violet pigment such as Manganese Violet, Fast Violet B and Methyl Violet Lake; a green pigment such as chromium oxide, Chrome Green, Pigment Green B, Malachite Green Lake and Final Yellow Green G; a white pigment such as Zinc White, titanium oxide, Antimony White and zinc sulfate; and an extender pigment such as baryta powder, barium carbonate, clay, silica, white carbon, talc and Alumina White. Of course, substances encapsulated in the liposome are not limited to these. These substances can be used in a combination of two substances or more, as necessary. Liposome encapsulating an ink component can be prepared by the aforementioned methods such as the ultrasonication method, the ethanol injection method, the French press method, the ether injection method, the cholic acid (surfactant) method, the calcium fusion method, the freezing and thawing method, the reverse phase evaporation method, the method using a glass filter, and the method using a commercially available kit such as coatsome.

Where the polyhydroxyalkanoate-coated liposome of the present invention is used, for example, as a capsule for sustained release of a drug, drugs for medicines encapsulated in the liposome include both readily water-soluble drugs and slightly water-soluble (fat-soluble) drugs. These drugs include, for example, a sterol (e.g. cholesterol and sitosterol), estrogen (for example, estrone, estradiol and esters thereof and ethynyl estradiol), corticoids and esters thereof, peptide hormone like calcitonin, antibiotics (for example, gentamicin, vancomycin, amikacin, kanamycin, streptomycin, minocycline and tetracycline), chloramphenicol, macrolide antibiotics (for example, erythromycin and derivatives thereof, in particular palmitates thereof or stearates thereof, or spiramycin), anti-parasite reagents and drugs for skin (for example, clotrimazole, miconazole and dithranol), antiphlogistic anodynes (for example, indomethacin, diclofenac, flurbiprofen, ketoprofen, 4-biphenylacetic acid and ethylates thereof), vitamins like cyanocobalamin, enzymes like urokinase, and anticancer drugs such as fluorouracil and alacitidine. These chemicals can be used in a combination of two substances or more, as necessary. Liposome encapsulating these drugs can be prepared by the aforementioned methods such as the ultrasonication method, the ethanol injection method, the French press method, the ether injection method, the cholic acid (surfactant) method, the calcium fusion method, the freezing and thawing method, the reverse phase evaporation method, a method using a glass filter, and a method using a commercially available kit such as coatsome.

Liposome prepared by an aforementioned method is increased in physical, mechanical strength by coating at least part of the outer wall with polyhydroxyalkanoate, and given biocompatibility and biodegradability. When liposome has sustained release properties, it can control sustained releasability. A method for coating the aforementioned liposome with polyhydroxyalkanoate will be described in the following.

<PHA>

PHA capable of being used in the present invention is not particularly limited as long as such a PHA can be synthesized with a PHA synthesizing enzyme involved in a biosynthesis reaction of PHA.

Here, the biosynthesis of PHA is carried out through a polymerization reaction by an enzyme using as a substrate (R)-3-hydroxyacyl CoA produced from alkanoic acids as a substrate by way of various metabolic pathways in an organism (e.g. β-oxidation system and fatty acid synthesis pathway). It is a PHA synthesizing enzyme (also referred to as PHA polymerase, PHA synthase) that catalyses this polymerization reaction. The term "CoA" is an abbreviation of coenzyme A, of which chemical structure is as follows:

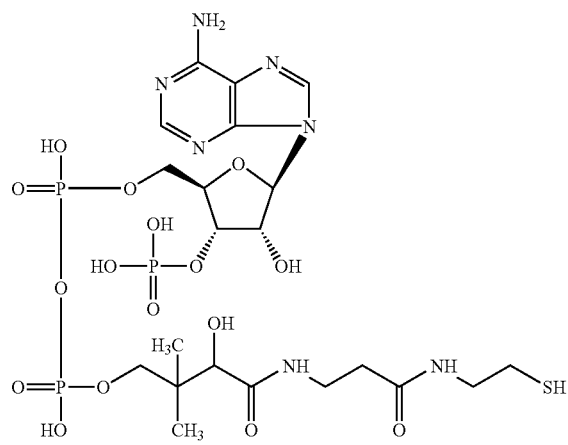

A reaction by which PHA is produced from alkanoic acid through a polymerization reaction by a β-oxidation system and a PHA synthesizing enzyme is shown in the following:

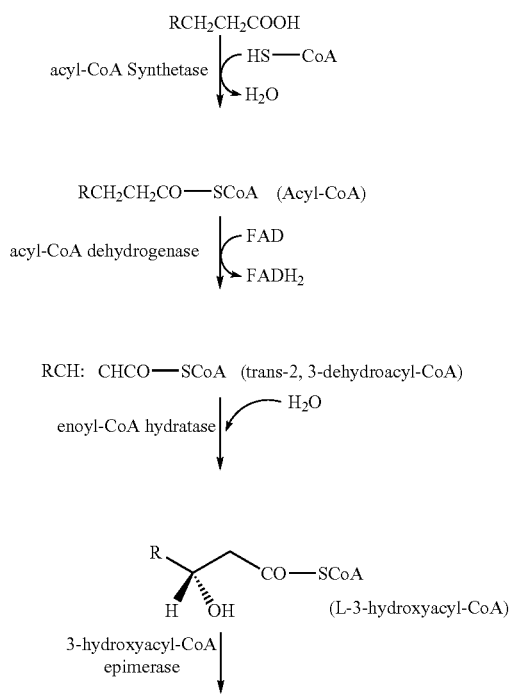

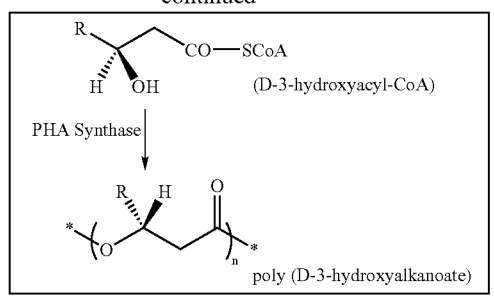

On the other hand, if the reaction is carried out by way of the fatty acid synthesis pathway, it can be considered that PHA is similarly synthesized by the PHA synthesizing enzyme using as a substrate (R)-3-hydroxyacyl CoA into which (R)-3-hydroxyacyl-ACP (ACP means an acyl carrier protein) produced in the pathway has been converted.

In addition, it is known that the above described PHB synthesizing enzyme and PHA synthesizing enzyme can be taken out from the cell to synthesize PHA in a cell-free system (in vitro), and specific examples thereof will be described below.

For example, in Proc. Natl. Acad. Sci. USA, 92, 6279–6283 (1995), it is reported that PHB comprising a 3-hydroxy-n-butanoic acid unit has been successfully synthesized by making 3-hydroxybutyryl CoA act on a PHB synthesizing enzyme derived from *Alcaligenes eutrophus*. In addition, it is reported in Int. J. Biol. Macromol., 25, 55–60 (1999) that PHA comprising a 3-hydroxy-n-butyryl acid unit or a 3-hydroxy-n-valeric acid unit has been successfully synthesized by making 3-hydroxybutyryl CoA and 3-hydroxyvaleryl CoA act on the PHB synthesizing enzyme derived from *Alcaligenes eutrophus*. In addition, according to this report, when racemic 3-hydroxybutyryl CoA was made to act on the enzyme, PHB comprising only a 3-hydroxy-n-butyric acid unit of R-configuration was synthesized due to the stereoselectivity of the enzyme. Synthesis of PHB outside the cell using a PHB synthesizing enzyme derived from *Alcaligenes eutrophus* is also reported in Macromol. Rapid Commun., 21, 77–84 (2000). In addition, it is reported in FEMS Microbiol. Lett., 168, 319–324 (1998) that PHB comprising a 3-hydroxy-n-butyric unit has been successfully synthesized by making 3-hydrozybutyryl CoA act on a PHB synthesizing enzyme derived from *Chromatium vinosum*. It is reported in Appl. Microbiol. Biotechnol., 54, 37–43 (2000) that PHA comprising a 3-hydroxydecanoic acid unit has been synthesized by making 3-hydroxydecanoyl CoA act on a PHA synthesizing enzyme from *Pseudomonas aeruginosa*.

In this way, the PHA synthesizing enzyme is an enzyme catalyzing a final stage in the PHA synthesis reaction system in an organism, and any PHA known to be capable of being synthesized in the organism is synthesized under catalytic action by the enzyme. Therefore, by making 3-hydroxyacyl CoA corresponding to desired PHA act on the enzyme fixed on the medium in the present invention, polyhydroxyalkanoate-coated liposome with any type of PHA known to be capable of being synthesized in the organism can be prepared.

As an example of PHA for use in the present invention, PHA containing at least monomer units expressed by the following formulas [1] to [10] can specifically be shown.

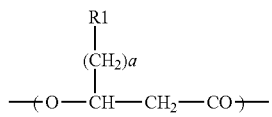

[1]

(wherein the monomer unit is at least one selected from the group consisting of monomer units having any of the following combinations of R1 and a:

a monomer unit in which R1 represents a hydrogen atom (H), and a represents an integer number of 0 to 10;

a monomer unit in which R1 represents a halogen atom, and a represents an integer number of 1 to 10;

a monomer unit in which R1 represents a chromophoric group, and a represents an integer number of 1 to 10;

a monomer unit in which R1 represents a carboxyl group or a salt thereof, and a represents an integer number of 1 to 10; and a monomer unit in which R1 represents

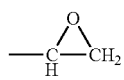

and a represents an integer number of 1 to 7.)

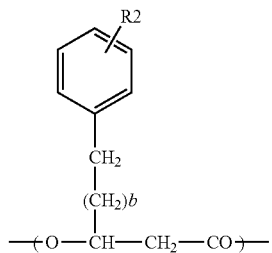

[2]

(wherein b represents an integer number of 0 to 7, and R2 represents any one selected from the group consisting of a hydrogen atom (H), halogen atom, —CN, —NO$_2$, —CF$_3$, —C$_2$F$_5$ and —C$_3$F$_7$.)

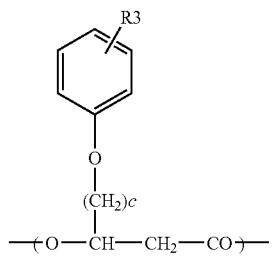

[3]

(wherein c represents an integer number of 1 to 8, and R3 represents any one selected from the group consisting of a hydrogen atom (H), halogen atom, —CN, —NO$_2$, —CF$_3$, —C$_2$F$_5$ and —C$_3$F$_7$.)

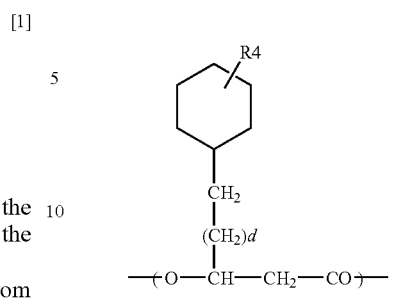

[4]

(wherein d represents an integer number of 0 to 7, and R4 represents any one selected from the group consisting of a hydrogen atom (H), halogen atom, —CN, —NO$_2$, —CF$_3$, —C$_2$F$_5$ and —C$_3$F$_7$.)

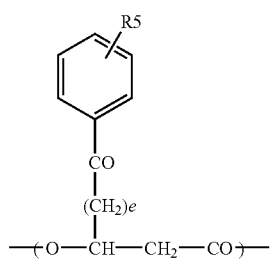

[5]

(wherein e represents an integer number of 1 to 8, and R5 represents any one selected from the group consisting of a hydrogen atom (H), halogen atom, —CN, —NO$_2$, —CF$_3$, —C$_2$F$_5$, —C$_3$F$_7$, —CNH$_3$, —C$_2$H$_5$ and —C$_3$H$_7$).

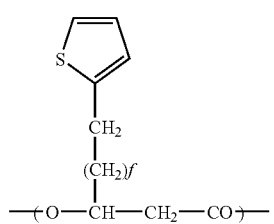

[6]

(wherein f represents an integer number of 0 to 7.)

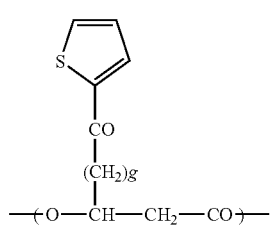

[7]

(wherein g represents an integer number of 1 to 8.)

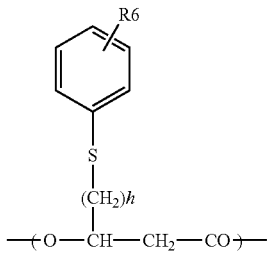

[8]

(wherein h represents an integer number of 1 to 7, R6 represents any one selected from the group consisting of a hydrogen atom (H), halogen atom, —CN, —NO$_2$, —COOR', —SO$_2$R", —CH$_3$, —C$_2$H$_5$, —C$_3$H$_7$, —CH(CH$_3$)$_2$ and —C(CH$_3$)$_3$ wherein R' represents any of a hydrogen atom (H), Na, K, —CH$_3$ and —C$_2$H$_5$, and R" represents any of —OH, —ONa, —OK, a halogen atom, —OCH$_3$ and —OC$_2$H$_5$.)

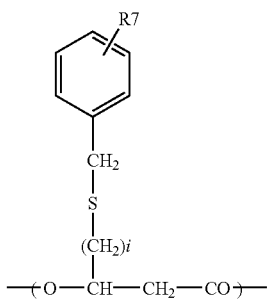

[9]

(wherein i represents an integer number of 1 to 7, R7 represents any one selected from the group consisting of a hydrogen atom (H), halogen atom, —CN, —NO$_2$, —COOR' and —SO$_2$R" wherein R' represents any of a hydrogen atom (H), Na, K, —CH$_3$ and —C$_2$H$_5$, and R" represents any of —OH, —ONa, —OK, a halogen atom, —OCH$_3$ and —OC$_2$H$_5$.)

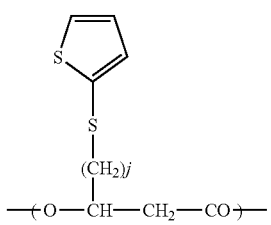

[10]

(wherein j represents an integer number of 1 to 9.)

Furthermore, examples of the above described halogen atom may include fluorine, chlorine and bromine.

A specific example of 3-hydroxyacyl CoA for use as a substrate for synthesizing the above PHA may be 3-hydroxyacyl CoA expressed by the following Chemical Formulas [12] to [21]:

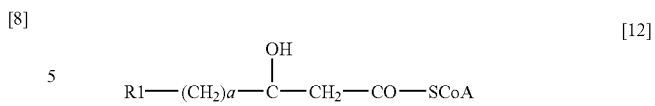

[12]

(wherein —SCoA represents a CoA bound to alkanoic acid, and the combination of R1 and a is defined as the same as the combinations of R1 and a in the monomer unit expressed by the above described Formula [1].)

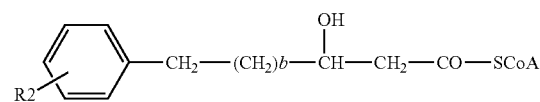

[13]

(wherein —SCoA represents a CoA bound to alkanoic acid, and b and R2 are respectively defined as the same as b and R2 in the monomer unit expressed by the above described Chemical Formula [2].)

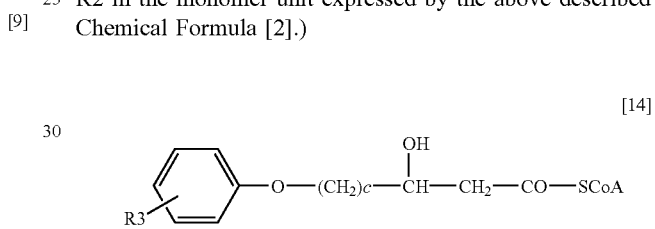

[14]

(wherein —SCoA represents a CoA bound to alkanoic acid, and c and R3 are respectively defined as the same as c and R3 in the monomer unit expressed by the above described Chemical Formula [3].)

[15]

(wherein —SCoA represents a CoA bound to alkanoic acid, and d and R4 are respectively defined as the same as d and R4 in the monomer unit expressed by the above described Chemical Formula [4].)

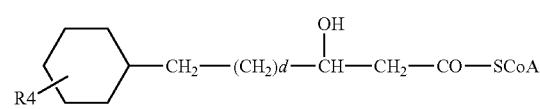

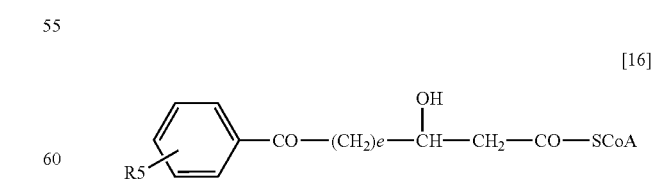

[16]

(wherein —SCoA represents a CoA bound to alkanoic acid, and e and R5 are respectively defined as the same as e and R4 in the monomer unit expressed by the above described Chemical Formula [5].)

[17]

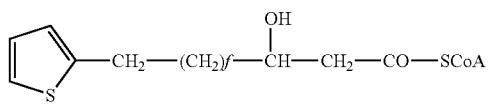

(wherein —SCoA represents a CoA bound to alkanoic acid, and f is defined as the same as f in the monomer unit expressed by the above described Chemical Formula [6].)

[18]

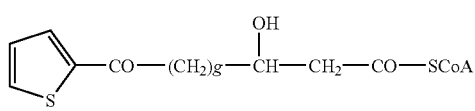

(wherein —SCoA represents a CoA bound to alkanoic acid, and g is defined as the same as g in the monomer unit expressed by the above described Chemical Formula [7].)

[19]

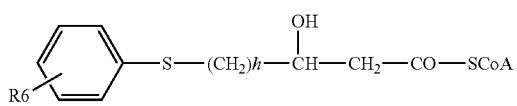

(wherein —SCoA represents a CoA bound to alkanoic acid, and h and R6 are respectively defined as the same as h and R6 in the monomer unit expressed by the above described Chemical Formula [8].)

[20]

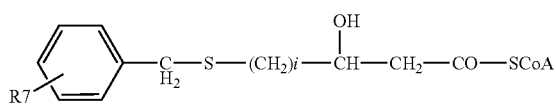

(wherein —SCoA represents a CoA bound to alkanoic acid, and i and R7 are respectively defined as the same as i and R7 in the monomer unit expressed by the above described Chemical Formula [9].)

[21]

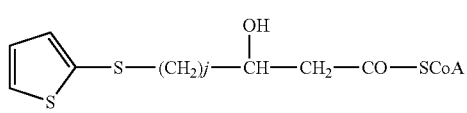

(wherein —SCoA represents a CoA bound to alkanoic acid, and j is defined as the same as j in the monomer unit expressed by the above described Chemical Formula [10].)

In addition, in the case where the polyhydroxyalkanoate-coated liposome of the present invention is used in a manner so as to be suspended in an aqueous medium, PHA having a hydrophilic functional group is used as PHA constituting the polyhydroxyalkanoate-coated liposome. The hydrophilic functional group may be any hydrophilic functional group, but an anionic functional group can be used, and the anionic functional group may be any anionic functional group, but a carboxyl group can be used in particular. An example of PHA having a carboxyl group may be PHA comprised of at least one selected the group consisting of monomer units expressed by the following formula [11].

[11]

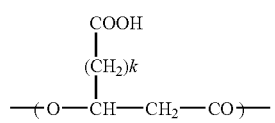

(wherein k represents any one of integer numbers of 1 to 10.)

In addition, a specific example of the above PHA may be PHA containing 3-hydroxypimelic acid expressed by the following Formula [23].

[23]

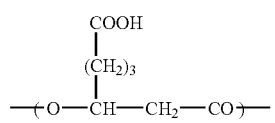

In addition, an example of 3-hydroxyacyl CoA for use as a substrate for synthesizing PHA expressed by the above Formula [11] may be 3-hydroxyacyl CoA expressed by the following Formula [22].

[22]

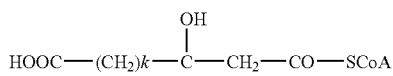

(wherein SCoA represents a CoA bound to alkanoic acid, and k represents at least one selected from the group consisting of the following numbers, and corresponds to k in the monomer unit expressed by the above described Formula [11]. K represents any one of integer numbers of 1 to 10.)

In addition, 3-hydroxyacyl CoA for use as a substrate for synthesizing PHA containing 3-hydroxypimelic acid expressed by the above Formula [23] may be 3-hydroxypimeril CoA expressed by the following Formula [24].

[24]

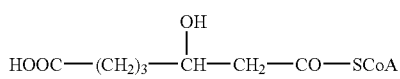

Furthermore, specific examples of the above described halogen atom may include fluorine, chlorine and bromine. In addition, the above described chromophoric group is not particularly limited as long as its 3-hydroxyacyl CoA body can be subjected to catalytic action of the PHA synthesizing enzyme, but it is more desirable that a methylene chain having 1 to 5 carbon atoms exists between the carboxyl group with CoA bound thereto and the chromophoric group in the 3-hydroxyacyl CoA molecule if considering steric hindrance that may occur during synthesis of a polymer. In addition, if the optical absorption wavelength of the chromophoric group is in the visible range, a colored polyhydroxyalkanoate-coated liposome can be obtained. Examples of such chromophoric groups may include nitroso, nitro, azo, diarylmethane, triarylmethane, xanthene, acridine, quinoline, methine, thiazole, indamine, indophenol, lactone, aminoketone, hydroxyketone, stilbene, azine, oxazine, thiazin, anthraquinone, phthalocyanine and indigoid.

For PHA to be used in the present invention, random copolymers and block copolymers each including the above described plurality of monomer units can also be used, thus making it possible to control properties of PHA and provide a plurality of functions using the properties of respective monomer units and contained functional groups, to realize new functions using interaction between functional groups, and so on. In addition, it is also possible to synthesize a block copolymer of any order and composition on the surface of the liposome by selecting as appropriate the amount and order in which 3-hydroxyacyl CoA as a substrate is added. In addition, as required, chemical modification and the like may also be made after or during synthesis of PHA.

It is also possible to change the composition of the monomer unit of PHA in the direction extending from the inside of the polyhydroxyalkanoate-coated liposome to the outside thereof by changing with time the composition such as type and concentration of 3-hydroxyacyl CoA as a substrate, for example. Thereby, for example, if it is necessary to form a polyhydroxyalkanoate-coated liposome with PHA having a low affinity for the liposome, the liposome is first covered with PHA having a high affinity for the liposome, and the composition of the monomer unit of PHA having a high affinity for the liposome is changed to the composition of the monomer unit of desired PHA in the laminated direction to form, for example, a multi-layer structure or gradient structure, thereby making it possible to form a PHA cover with its bonding to the liposome enhanced.

In addition, chemical modification of the PHA can provide polyhydroxyalkanoate-coated liposome various properties of which are improved. For example, the incorporation of a graft chain into a PHA can give polyhydroxyalkanoate-containing organic structure such as a PHA-coated liposome at least part of which has been coated with the PHA being given a variety of properties attributable to the graft chain. Further, crosslinking the PHA can provide polyhydroxyalkanoate-containing organic structure such as a PHA-coated liposome at least part of which has been coated with the PHA given a variety of physicochemical properties (for example, mechanical strength, resistance to chemicals and heat resistance). The term, "chemical modification" as used in the present invention indicates the meaning that the molecular structure of a polymer substance is altered by allowing an intramolecular or intermolecular chemical reaction of the polymer substance or a chemical reaction between the polymer substance and another chemical substance. The term, "crosslinking" indicates the meaning that a polymer substance is chemically or physicochemically bonded intramolecularly or intermolecularly to form a network structure. Furthermore, a crosslinking agent refers to a substance having a certain reactivity with the aforementioned polymer substance which is added to carry out the above crosslinking reaction.

Furthermore, PHA synthesized by a PHA synthesizing enzyme, which is used in the structure of the present invention, is generally an isotactic polymer constituted only by a R-configuration. 3-hydroxyacyl CoA as a synthesis substrate for PHA can be synthesized for use by a method appropriately selected from an in vitro synthesis method using enzymes, an in vivo synthesis method using organisms such as microorganisms and plants, a chemical synthesis method, and the like. In particular, the enzyme synthesis method is a method that is generally used for synthesis of the substrate, and known enzyme synthesis methods include a method using the following reaction using commercially available acyl CoA synthetase (Acyl CoA Ligase, E.C.6.2.1.3)(Eur. J.Biochem., 250, 432–439 (1997), Appl. Microbiol. Biotechnol., 54, 37–43 (2000), etc.):

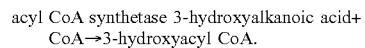

acyl CoA synthetase 3-hydroxyalkanoic acid+ CoA→3-hydroxyacyl CoA.

For the synthesis process using enzymes and organisms, a batch type synthesis method may be used, or series production may be carried out using immobilized enzymes and immobilized cells.

<PHA Synthesizing Enzymes and Microorganisms for Producing the Enzymes>

For the PHA synthesizing enzyme for use in the present invention, an enzyme produced by a microorganism appropriately selected from microorganisms capable of producing the enzyme, or a transformant with the gene of a PHA synthesizing enzyme introduced into the host may be used.

For microorganisms for producing PHA synthesizing enzymes, PHB or PHB/V producing microorganisms may be used, and as these microorganisms, *Burkholderia cepacia* KK01, *Ralstonia eutropha* TB64, *Alcaligenes* sp. TL2 that have been isolated by the inventors may be used in addition to *Aeromonas* sp., *Alcaligenes* sp., *Chromatium* sp., *Comamonas* sp., *Methylobacterium* sp., *Paracoccus* sp., *Pseudomonas* sp. and the like. Furthermore, KK01, TB64 and TL2 are deposited as FERM BP-4235, FERM BP-6933 and FERM BP-6913, respectively, in National Institute of Advanced Industrial Science and Technology, International Patent Organism Depositary.

Also, as microorganisms for producing PHA synthesizing enzymes, microorganisms producing mcl-PHA and unusual-PHA may be used, and as these microorganisms may be used *Pseudomonas* sp. microorganisms such as *Pseudomonas putida* P91, *Psuedomonas cichorii* H45, *Pseudomonas cichorii* YN2, *Pseudomonas jessenii* P161, etc. that have been isolated by the inventors, in addition to *Pseudomonas oleoborans, Pseudomonas resinoborans, Pseudomonas* sp. 61-3, *Pseudomonas putida* KT2442, *Pseudomonas aeruginosa* and the like, and *Burkholderia* sp. microorganisms such as *Burkholderia* sp. OK3 (FERM P-17370) described in Japanese Patent Application Laid-Open No. 2001-78753 and *Burkholderia* sp. OK4 (FERM P-17371) described in Japanese Patent Application Laid-Open No. 2001-69968. Also, in addition to these microorganisms, microorganisms belonging to *Aeromonas* sp., *Comamonas* sp. and the like and producing mcl-PHA and unusual-PHA can be used.

Furthermore, P91, H45, YN2 and P161 are deposited on an international basis as FERM BP-7373, FERM BP-7374, FERM BP-7375 and BP-7376, respectively, in National Institute of Advanced Industrial Science and Technology, International Patent Organism Depositary, under Budapest Treaty on international approval for deposition of microorganisms in terms of patent procedures.

For normal culture of microorganisms for use in production of PHA synthesizing enzymes according to the present invention, for example preparation of stock strains, and reproduction for securing the number of cells and their active states required for production of the PHA synthesizing enzyme, a culture medium containing components needed for growth of microorganisms to be used is appropriately selected and used. For example, any type of culture media such as general natural culture media (broths, yeast extracts, etc.) and synthetic culture media with nutrient sources added thereto may be used unless they adversely affect growth and survival of microorganisms.

For the culture, any method such as liquid culture and solid culture may be used as long as reproduction of the microorganisms is possible. In addition, any type of culture including batch culture, fed batch culture, semi-continuous culture and continuous culture may be used. As for the form of the liquid batch culture, a method in which oxygen is supplied by shaking with a shaking flask, a method in which oxygen is supplied using a stirring aeration system with a jar fermenter and the like are employed. In addition, a multi-stage method in which these steps are connected in multiple stages may be employed.

In the case where the PHA synthesizing enzyme is produced using PHA producing microorganisms as described above, for example, a method in which the microorganism is grown in an inorganic culture medium containing alkanoic acid such as octanoic acid and nonanoic acid, and cells of the microorganism in the logarithmic growth phase to the early stage of the stationary phase are collected by centrifugation or the like to extract a desired enzyme, and so on may be used. Furthermore, if the microorganism is cultured using a condition as described above, mcl-PHA derived from added alkanoic acid is synthesized in a cell of the microorganism, but in this case, it is generally said that the PHA synthesizing enzyme exists in such a manner as to be bound to small particles of PHA produced in the cell. However, as a result of studies conducted by the inventors, it has been found that almost equivalent enzyme activity is present even in the supernatant liquid after conducting centrifugation of the liquid from fragmentation of cells cultured by any of the above described methods. It is assumed that this is because an almost equivalent amount of PHA synthesizing enzyme exists in a free state in a relatively early stage of culture, which is from the logarithmic growth phase to the early stage of the stationary phase as described above, since the enzyme is actively produced continuously in the cell.

For the inorganic culture medium for use in the above culture methods, any medium containing components enabling microorganisms to be grown such as phosphorous sources (e.g. phosphates) and nitrogen sources (e.g. ammonium salts, nitrates, etc.) may be used, and inorganic culture media may include, for example, a MSB medium, E medium (J. Biol. Chem., 218, 97–106 (1956)) and M9 medium. Furthermore, the composition of the M9 medium for use in Examples of the present invention is as follows:

$Na_2HPO_4$: 6.2 g
$KH_2PO_4$: 3.0 g
NaCl: 0.5 g
$NH_4Cl$: 1.0 g
(per liter of medium, pH 7.0).

In addition, about 0.3% (v/v) of a solution containing minor components shown below is preferably added in the above inorganic culture medium for ensuring satisfactory growth of the microorganism and production of the PHA synthesizing enzyme:

(Solution Containing Minor Components)
nitrilotriacetic acid: 1.5 g
$MgSO_4$: 3.0 g
$MnSO_4$: 0.5 g
NaCl: 1.0 g
$FeSO_4$: 0.1 g
$CaCl_2$: 0.1 g
$COCl_2$: 0.1 g
$ZnSO_4$: 0.1 g
$CuSO_4$: 0.1 g
$AlK(SO_4)_2$: 0.1 g
$H_3BO_3$: 0.1 g
$Na_2MoO_4$: 0.1 g
$NiCl_2$: 0.1 g
(per liter)

The culture temperature may be any temperature at which the above microorganism can satisfactorily be grown, for example 14 to 40° C., preferably 20 to 35° C.

Also, a desired PHA synthesizing enzyme can be produced using a transformant having a PHA synthesizing enzyme gene of the aforesaid PHA producing microorganism. Cloning of the PHA synthesizing enzyme gene, preparation of an expression vector, and preparation of the transformant may be carried out in accordance with an established method. In a transformant obtained with a microorganism such as *colibacillus* as a host, the medium for use in culture is a natural medium or a synthetic medium, for example, a LB medium, M9 medium or the like. A culture temperature is in the range of from 25 to 37° C. In addition, aerobic culture is conducted for 8 to 27 hours to achieve growth of the microorganism. Thereafter, cells can be collected to collect the PHA synthesizing enzyme accumulated in the cells. Antibiotics such as kanamycin, ampicillin, tetracycline, chloramphenicol and streptomycin may be added in the medium as necessary. Also, in the case where an inductive promoter is used in the expression vector, an inductive material corresponding to the promoter may be added to the medium to promote expression when the transformant is cultured. Such inductive materials include, for example, isopropyl-1-thio-β-D-galactoside (IPTG), tetracycline and indolacrylic acid (IAA).

For the PHA synthesizing enzyme, liquids from fragmentation of cells of microorganism, and crude enzymes such as salted ammonium sulfate obtained by precipitation and collection of protein components with ammonium sulfate and the like may be used, or enzymes purified by various kinds of methods may be used. Stabilizers such as metal salts, glycerin, dithiothreitol, EDTA and bovine serum albumin (BSA), and activators may be added to the enzymes as necessary.

For isolation and purification of PHA synthesizing enzymes, any method allowing enzyme activation of PHA synthesizing enzymes to be retained may be used. For example, obtained cells of microorganism are crushed with a French press, a supersonic crusher, lysozyme, various kinds of surfactants and the like, and thereafter, for a crude enzyme solution obtained by centrifugation or salted ammonium sulfate prepared therefrom, means such as affinity chromatography, cation or anion exchange chromatography, and gel filtration is applied alone or in combination, whereby a purified enzyme can be obtained. In particular, a gene recombination protein can be purified more conveniently by expressing the protein in the form of united protein with "tags" such as histidine residues bound to the N terminal and C terminal, and making the protein to be bound to an affinity resin through these tags. For isolating a desired protein from the united protein, methods of cleaving the linkage by protease such as thrombin and a blood coagulation factor Xa, decrasing the pH, adding a high concentration of imidazole as a competitive binding agent and the like may be used. Alternatively, if the tag includes intein as in the case of using pTYB1 (manufactured by New EnglanBiolab Co., Ltd.) as a expression vector, a reduction condition is achieved by dithiothreitol or the like to cleave the linkage. For the united protein enabling purification by affinity chromatography, glutathione-S-transferase (GST), chitin bound domain (CBD), maltose bound protein (MBP) and thioredoxine (TRX) are also well known in addition to the histidine tag. The GST united protein can be purified by the GST affinity resin.

A various kinds of reported methods may be used for measuring activity of the PHA synthesizing enzyme, and for example, the activity may be measured by the following method in which as a measurement principle, CoA released in the process through which 3-hydroxyacyl CoA is polymerized under the catalytic action of the PHA synthesizing enzyme to form PHA is colored with 5,5'-dithiobis-(2-nitrobenzoic acid) to carry out measurements. Reagent 1: bovine serum albumin (manufactured by Sigma Co., Ltd.) is dissolved in a 0.1 M Tris hydrochloric buffer (pH 8.0) in the concentration of 3.0 mg/ml, Reagent 2: 3-hydroxyoctanoyl CoA is dissolved in a 0.1 M Tris hydrochloric buffer (pH 8.0) in the concentration of 3.0 mM, Reagent 3: trichloroacetic acid is dissolved in a 0.1 M Tris hydrochloric buffer (pH 8.0) in the concentration of 10 mg/ml, and Reagent 4: 5,5'-dithiobis-(2-nitrobenzoic acid) is dissolved in a 0.1 M Tris hydrochloric buffer (pH 8.0) in the concentration of 2.0 mM. First reaction (PHA synthesis reaction): 100 µl of Reagent 1 is added in 100 µl of sample (enzyme) solution and mixed together, and is pre-incubated at 30° C. for a minute. 100 µl of Reagent 2 is added thereto and mixed together, and is incubated at 30° C. for 1 to 30 minutes, followed by adding thereto Reagent 3 to stop the reaction. Second reaction (reaction of coloring free CoA): the first reaction solution of which reaction has been stopped is subjected to centrifugation (15,000×g, 10 minutes), and 500 µl of Reagent 4 is added in 500 µl of supernatant liquid of this solution, and is incubated at 30° C. for 10 minutes, followed by measuring an absorbance at 412 nm. Calculation of enzyme activity: the amount of enzyme for releasing 1 µmol of CoA per minute is defined as one unit (U).

[Process for Producing PHA-coated Liposome]

Figure 1B:
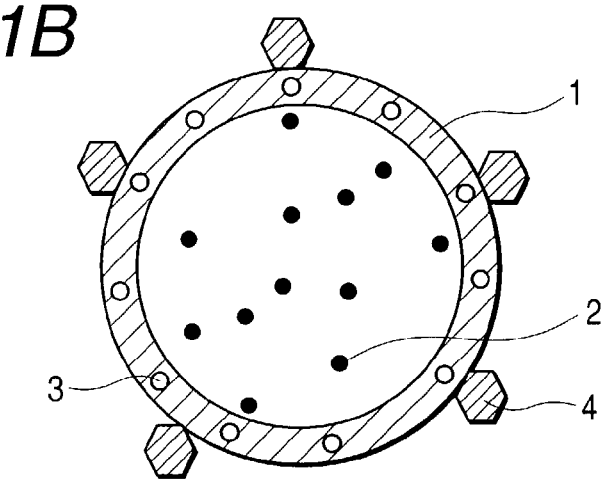
Figure 1C:
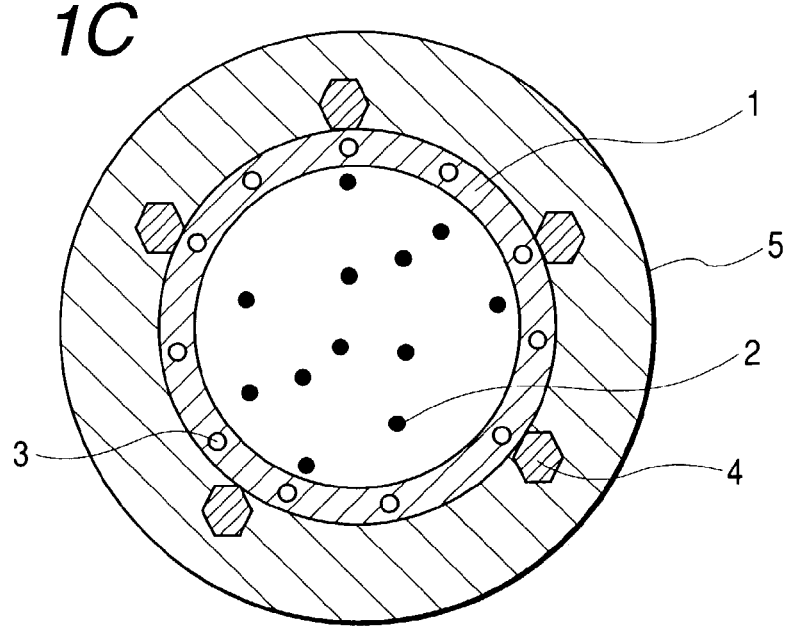

As shown in FIGS. 1A to 1C, one example of process for production of PHA-coated liposome of the present invention may be a process comprising at least steps of (1) dispersing the liposome prepared in the above-mentioned manner on an aqueous medium (FIG. 1A), (2) fixing a PHA synthesizing enzyme to the dispersed liposome (FIG. 1B), (3) adding 3-hydroxyacyl CoA as a substrate, (4) carrying out a PHA synthesis reaction (FIG. 1C) and (5) collecting the PHA-coated liposome, drying the resultant as occasion demands, and dispersing the resultant into a medium suitably selected according to a use to process the resultant as a dispersed system. In FIGS. 1A to 1C, the numeral 2 designates the liposome; 2, the water-soluble material encapsulated inside the liposome; 4, the polyhydroxyalkanoate synthase fixed to the liposome; and 5, polyhydroxyalkanoate.

The step of dispersing the liposome on the aqueous medium is conducted by adding one or more selected liposomes in the aqueous medium, and carrying out dispersion processing, followed by classifying the liposome in a desired range of particle size if necessary.

It is desirable that the liposome is dispersed in a single dispersion state in the range of from 100 nm to 100 µm for the particle size of the dispersed liposome, while such a condition depends on the use. If the particle size of the dispersed liposome is not fallen in a desired range, classification by filtration and sedimentation processes can be carried out to make an adjustment.

The particle size of the dispersed liposome can be measured by known methods such as an absorbance method, a static light-scattering method, a dynamic light scattering method method and a centrifugal sedimentation method, and for example, an apparatus for measuring particle sizes such as Coulter counter multi-sizer may be used.

The composition of the aqueous medium for synthesis of PHA in this step may be any composition that allows the liposome to be dispersed in a desired state, and does not interfere the subsequent steps of fixing the enzyme to the liposome and carrying out the PHA synthesis reaction, but the composition may be adjusted into a composition allowing the activity of the PHA synthesizing enzyme to be exerted in order to simplify the subsequent steps. As the composition allowing the activity of the PHA enzyme to be exerted, for example, a buffer may be used. For the buffer, general buffers for use in biochemical reactions, for example, acetate buffers, phosphate buffers, potassium phosphate buffers, 3-(N-morpholino)propane sulfonate (MOPS) buffers, N-tris (hydroxymethyl)methyl-3-aminopropane sulfonate (TAPS) buffers, trischloride buffers, glycin buffers, and 2-(cyclohexylamino)ethanesulfonate (CHES) buffers are suitably used. The concentration of the buffer allowing the activity of the PHA synthesizing enzyme to be exerted may be a general concentration, namely in the range of from 5 mM to 1.0 M, but is preferably in the range of from 10 to 200 mM. Also, an adjustment is made so that pH is in the range of from 5.5 to 9.0, preferably from 7.0 to 8.5, but the possibility is not excluded that a pH condition is set in a range other than the above described range depending on the most suitable pH and pH stability of a PHA synthesizing enzyme to be used.

In addition, for maintaining a liposome dispersion condition in the aqueous medium, a suitable surfactant may be added as long as the surfactant has a type and concentration not interfering the subsequent steps, and has a type and concentration not interfering the purpose of the PHA-coated liposome of the present invention. Examples of the surfactant may include, for example, anionic surfactants such as sodium oleate, sodium dodecylsulfonate, sodium dodecyl sulfate, sodium dodecyl-N-sarcosinate, sodium cholate, sodium deoxycholate and sodium taurodeoxycholate; cationic surfactants such as cetyltrimethylammonium bromide and dodecylpyridinium chloride; ampholytic surfactants such as 3-[(choleamidepropyl) dimethylammonio]-1-propanesulfonic acid (CHAPS), 3-[(3-choleamidepropyl)dimethylammonio]-2-hydroxy-1-propanesulfonic acid (CHAPSO), palmitoyllysolecithin and dodecyl-β-alanine; and nonionic surfactants such as octylglucoside, octylthioglucoside, heptylthioglucoside, decanoyl-N-methylglucamide (MEGA-10), polyoxyethylenedodecylether (Brij, Lubrol), polyoxyethylene-i-octylphenylether (Triton X), polyoxyethylenenonylphenylether (Nonidet P-40, Triton N), polyoxyethylene fatty acid ester (Span) and polyoxyethylenesorbitol ester (Tween).

In addition, for maintaining a dispersion of the liposome in the aqueous medium, a suitable auxiliary solvent may be added as long as it has a type and concentration not interfering the subsequent steps, and has a type and concentration not interfering a property necessary for a use of a PHA-coated liposome of the present invention. For the auxiliary solvent, one or two types of substances selected from, for example, linear aliphatic hydrocarbons such as hexane, and their derivatives such as monovalent alcohols such as methanol and ethanol, polyvalent alcohols such as glycerol, fatty acid ethers and carboxylates may be selected and used.

The step of fixing the PHA synthesizing enzyme to the liposome can be carried out by adding the PHA synthesizing enzyme in the aforesaid liposome dispersion, and subjecting the same to fixation processing. For the fixation processing, any method may be selected from enzyme fixation methods that are normally used as long as the method allows the activity of the enzyme to be retained, and are capable of being applied in desired liposome. For example, these methods may include a covalent binding method, ion absorption method, hydrophobic adsorption method, physical adsorption method, affinity adsorption method, crosslinking method and lattice inclusion method, but fixation methods using ion adsorption and hydrophobic adsorption are particularly convenient.

The enzyme protein such as a PHA synthesizing enzyme is a polypeptide in which a large number of amino acids are bound, and shows properties as an ion absorbent due to amino acids having free ionic groups such as lycine, histidine, arginine, asparaginic acid and glutamic acid, and have properties as a hydrophobic absorbent due to amino acids having free hydrophobic groups such as alanine, valine, leucine, isoleucine, methionine, tryptophane, phenylalanine and proline in terms that it is an organic macromolecule. Thus, the enzyme protein can be more or less adsorbed to a liposome having ionicity or hydrophobicity, or having both ionicity and hydrophobicity.

A method of immobilizing a PHA synthase primarily by means of the ion adsorption method may utilize liposome expressing a functional group on the surface thereof, for example, employ an anionic charge-providing lipid such as phosphatidylserine or phosphatidylic acid, dicethyl phosphoric acid, or phosphatidylinositol, or a coexist cationic charge-providing lipid such as a stearyl amine, thereby preparing liposome.

Fixation of the PHA synthesizing enzyme to the liposome by the ion adsorption or hydrophobic adsorption method is achieved by mixing the liposome and the PHA synthesizing enzyme together in a predetermined aqueous medium so that a predetermined concentration is obtained. At this time, it is desirable that the reaction vessel is shaken or stirred at a predetermined strength so that the enzyme can be evenly adsorbed to the surface of the liposome.

In the above described fixation processing, it is desirable that the composition of the aqueous medium in which the liposome and the enzyme are mixed together is determined in consideration of changes in positive and negative surface charge, the amount of charge and hydrophobicity of the liposome and PHA synthesizing enzyme due to the pH and salt concentration of the aqueous medium. For example, if the liposome is ion-adsorptive, the amount of charge contributing to adsorption between the liposome and the PHA synthesizing enzyme can be increased by reducing the salt concentration. Also, the opposite charge of the liposome and PHA synthesizing enzyme can be increased by changing pH. In addition, the amount of adsorption between the liposome and the PHA synthesizing enzyme can directly be measured to determine the composition. For measurements of the amount of adsorption, for example, a method may be used in which a solution of PHA synthesizing enzyme of which concentration is known is added in a solution with a liposome dispersed therein to carry out adsorption processing, followed by measuring the concentration of the PHA synthesizing enzyme in the solution and determining the amount of the adsorbed enzyme using a subtraction method.

In case of a liposome in which it is difficult for the ion adsorption method and the hydrophobic adsorption method to fix the enzyme, covalent bonding may be used for the fixation of the enzyme with the aid of any treatment as necessary that takes into account the complexity of an operation and the possibility of loss of the activity of the enzyme. For example, such cases include a process that carries out an exchange reaction between a liposome having a thiol reaction group (reactive group capable of reacting with a thiol group such as the dithiopyridyl group and the maleimide group) and a thiol group of the enzyme. In addition, a method can be used to couple the enzyme with a liposome containing a phospholipid having an amino group such as a phosphatidylethanol amine by activating a hydroxyl group, an amine group or a carboxyl group of the enzyme by use of a single functional group activation reagent such as imide N-hydroxysuccinate, ethyl chloroformate, dicyclohexylcarbodiimide (DCC), Woodward reagent K, cyanuric acid and trifluoromethane sulfonylchloride, or by activating the enzyme by use of various two-functional group crosslinking reagents containing a group with different reactivity such as some di-isocyanates.

In addition, the enzyme may be fixed to a liposome with a ligand introduced therein by affinity adsorption. In this case, any substance may be selected as the ligand as long as it enables affinity adsorption while maintaining the activity of the PHA synthesizing enzyme. Also, the enzyme may be fixed by binding a different biopolymer such as a protein to the PHA synthesizing enzyme, and subjecting the bound biopolymer to affinity adsorption. The biopolymer may be bound to the PHA synthesizing enzyme by gene recombination or the like, or by a chemical process.

Also, a peptide including amino acid sequences having binding capacity for the liposome can be united to the polyhydroxyalkanoate synthesizing enzyme and exhibited to fix the polyhydroxyalkanoate synthesizing enzyme on the surface of the liposome based on the bonding between the part of peptide corresponding to the amino acid sequence having binding capacity for the liposome and the liposome.

The amino acid sequence having binding capacity for the liposome can be determined by the screening of a random peptide library, for example. In particular, for example, a phage display peptide library prepared by coupling a random synthesis gene to the N-terminal gene of the surface protein of the M13 type phage (e.g. gene III protein) can be suitably used, but in this case, determination of the amino acid sequence having binding capacity for the liposome is carried out in accordance with the following procedure. Specifically, the phage display peptide library is added to the liposome or a phospholipid comprised in the liposome to contact the phage to the phospholipid, followed by separating bound phages and non-bound phages by washing. The liposome-bound phage is eluted with an acid or the like and neutralized with a buffer solution, and *colibacillus* is thereafter infected with the phage to amplify the phage. If this screening process is repeated several times, a plurality of clones having binding capacity for a desired liposome are concentrated. Here, for obtaining a single clone, colonies are made on the culture plate with the phage with which *colibacillus* is infected again. Each single colony is cultured on the liquid culture medium, followed by precipitating and purifying the phage existing in the supernatant liquid of the medium by polyethylene glycol or the like, and analyzing the base sequence, whereby the structure of the peptide can be known.

The amino sequence of the peptide having binding capacity for the liposome, obtained by the above described method, is united to the polyhydroxyalkanoate synthesizing enzyme using a normal gene engineering methodology for use. The peptide having binding capacity for the liposome can be coupled to the N-terminal or C-terminal of the polyhydroxyalkanoate synthesizing enzyme to be expressed. The peptide can also be expressed with an appropriate spacer sequence inserted. The spacer sequence has preferably about 3 to 400 amino acids, and may include any amino acid. Most preferably, the spacer sequence neither prevents the PHA synthesizing enzyme from functioning nor prevents the PHA synthesizing enzyme from being bound to the liposome.

The liposome with the enzyme fixed thereto, prepared by the above described method, may be used directly, but may also be used after being subjected to freeze-drying or the like.

The amount of phospholipid fixed to the liposome may be set in the range of from 10 units (U) to 1,000 units (U), desirably from 50 units (U) to 500 units (U) per 1 g of phospholipid, wherein one unit (U) is defined as the amount of PHA synthesizing enzyme when the amount of CoA released in the reaction through which PHA is synthesized by polymerization of 3-hydroxyacyl CoA equals 1 µmol per minute.

A time period over which fixation of the enzyme is carried out is desirably 1 minute to 24 hours, more desirably 10 minutes to 1 hour. Standing the sample at rest or leaving it to stand for excessively long time is not preferable because coagulation of liposomes and reduction of enzyme activity may be caused.

Also, the enzyme may be fixed to the liposome by adding the liposome directly to the enzyme solution without carrying out the previous step of dispersing the liposome in the aqueous medium, and then dispersing the liposome in the enzyme solution. In this case, electric repulsion and steric hindrance associated with the ionic functional group possessed by the enzyme fixed to the liposome makes it possible to facilitate dispersion of the liposome in the aqueous medium and eliminate necessity to add a surfactant in the aqueous medium or reduce the amount of the surfactant.

The step of adding 3-hydroxyacyl CoA as a substrate is achieved by adding a preserved solution of 3-hydroxyacyl CoA separately prepared to the aqueous dispersion of the liposome with the enzyme fixed thereto in the previous step so that a desired concentration is reached. 3-hydroxyacyl CoA as a substrate is added in final concentrations of generally from 0.1 mM to 1.0 M, desirably from 0.2 mM to 0.2 M, and further preferably 0.2 mM to 1.0 mM.

Also, in the above describe step, the composition such as type and concentration of 3-hydroxyacyl CoA in the aqueous reaction solution is changed with time, thereby making it possible to change the composition of the monomer unit of PHA covering the liposome in the direction extending from the inside toward the outside of the liposome.

The form of this liposome with the monomer unit composition changed may be, for example, a form in which the change of the composition of the PHA cover is continuous, and the liposome is covered with one layer of PHA having a gradient of composition formed in the direction extending from the inside toward the outside. The production method may be, for example, a method in which 3-hydroxyacyl CoA of different composition is added in the reaction solution while synthesizing PHA.

In addition, as another form, there may be a form in which the composition of the PHA cover is changed by stages, and PHA of different compositions covers the liposome in multiple layers. The production method for this form may be a method in which PHA is synthesized with a certain composition of 3-hydroxyacyl CoA, followed by collecting the liposome under preparation from the reaction solution on a temporary basis using centrifugation, gel filtration and the like, and adding thereto a reaction solution of 3-hydroxyacyl CoA of different composition again, and so on.

The step of carrying out a PHA synthesis reaction is carried out by preparing the composition of reaction solution so that a composition allowing activity of the PHA synthesizing enzyme to be exerted can be obtained if the composition of reaction solution has not been prepared till the previous step, and adjusting the reaction temperature and reaction time, in order that a PHA-coated liposome having a desired shape can be obtained by PHA to be synthesized.

The concentration of the buffer for the reaction solution allowing the activity of the PHA synthesizing enzyme to be exerted may be a general concentration, namely a concentration in the range of from 5 mM to 1.0 M, but is desirably a concentration in the range of from 10 to 200 mM. For pH, an adjustment is made so that the pH is in the range of from 5.5 to 9.0, preferably from 7.0 to 8.5, but the possibility is not excluded that a pH condition is set in a range other than the above described range depending on the most suitable pH and pH stability of a PHA synthesizing enzyme to be used.

The reaction temperature is set as appropriate depending on the property of the PHA synthesizing enzyme to be used, but may be set normally at 4 to 50° C., preferably at 20 to 40° C. However, the possibility is not excluded that a temperature condition is set in a range other than the above described range depending on the most suitable temperature and heat resistance of a PHA synthesizing enzyme to be used.

The reaction time is appropriately selected and set within the range of normally from 1 minute to 24 hours, preferably from 30 minutes to 3 hours depending on stability, etc. of the PHA synthesizing enzyme to be used.

The PHA-coated liposome is obtained by this step, but the structure of monomer units of PHA constituting the liposome can be determined by extracting PHA from the PHA-coated liposome with chloroform, and thereafter carrying out composition analysis by gas chromatography or the like, or using a time-of-flight secondary ion mass spectrometer (TOF-SIMS) and an ion sputtering technique.

The molecular weight of PHA is not particularly limited, but the number-average molecular weight is desirably in the range of from 1,000 to 10,000,000, more preferably from 3,000 to 1,000,000 for maintaining strength of the PHA-coated liposome, and providing a stable amount of charge. The molecular weight of PHA may be measured by GPC (gel permeation chromatography) after PHA is extracted from the PHA-coated liposome with chloroform.

The content of PHA coating depends on a use of PHA-coated liposome but is, for example, in the range of from 1 to 30% by mass, preferably from 1 to 20% by mass, more preferably 1 to 15% by mass based on the dry mass of the liposome.

The particle size of the PHA-coated liposome obtained by the above step depends on a use of PHA-coated liposome but is generally 50 µm or smaller, preferably 10 µm or smaller, more preferably 0.01 to 10 µm. The particle size of the PHA-coated liposome can be measured by known methods such as an absorbance method, a static light-scattering method, a dynamic light scattering method method and a centrifugal sedimentation method, and for example, an apparatus for measuring particle sizes such as a Coulter counter multi-sizer may be used.

In addition, the PHA-coated liposome obtained by this step may be subjected to various kinds of secondary treatments and processing such as chemical modification before being used.

For example, a PHA-coated liposome having further useful functions and properties can be obtained by subjecting PHA on the surface of the PHA-coated liposome to chemical modification. For example, a graft chain is introduced, whereby a PHA-coated liposome having various kinds of properties derived from the graft chain can be obtained. If polysiloxane as described later is introduced as a graft chain, for example, a PHA-coated liposome having more improved mechanical strength, dispersibility, weather resistance, water repellency (resistance), heat resistance and the like can be obtained. In addition, by having PHA on the PHA-coated liposome crosslinked, mechanical strength, chemical resistance, heat resistance and the like of the PHA-coated liposome can be more improved.

The method for chemical modification is not particularly limited as long as it is a method by which the purpose of obtaining a desired function and structure is achieved, but, for example, a method in which PHA having a reactive functional group on the side chain is synthesized, and chemical modification is accomplished using the chemical reaction of the functional group may be used as a suitable method.

The type of the above described reactive functional group is not particularly limited as long as it serves the purpose of obtaining a desired function and structure, and may be, for example, an epoxy group as described previously. PHA having an epoxy group on the side chain can be chemically converted as in the case of a normal polymer having an epoxy group. Specifically, for example, conversion into a hydroxyl group, and introduction of a sulfone group are possible. Also, a compound having thiol and amine can be added, and for example, a compound having a reactive functional group at the terminal, specifically a compound having an amino group having high reactivity with the epoxy group is added and reacted, whereby the graft chain of polymer is formed.

Compounds having amino groups on the terminals may include, for example, polyvinyl amine, polyethylene imine, and amino modified polymers such as amino modified polysiloxane (amino modified silicone oil). Among them, for amino modified polysiloxane, commercially available modified silicone oil, or amino modified polysiloxane that is synthesized by a method described in J. Amer. Chem. Soc., 78, 2278 (1956) or the like may be used, and the effect of improving mechanical strength, dispersibility, light resistance, weather resistance, water repellency (resistance) and heat resistance and so on by addition of the graft chain of the polymer can be expected.

In addition, another example of chemical conversion of a polymer having an epoxy group is a crosslinking reaction by a diamine compound such as hexamethylenediamine, succinic anhydrate, 2-ethyl-4-methylimidazole, or the like, and an example of physicochemical conversion is a crosslinking reaction by irradiation with electron rays or the like. Among them, the reaction between PHA having an epoxy group on the side chain and hexamethylenediamine progresses in accordance with a scheme as described below to produce a crosslinked polymer.

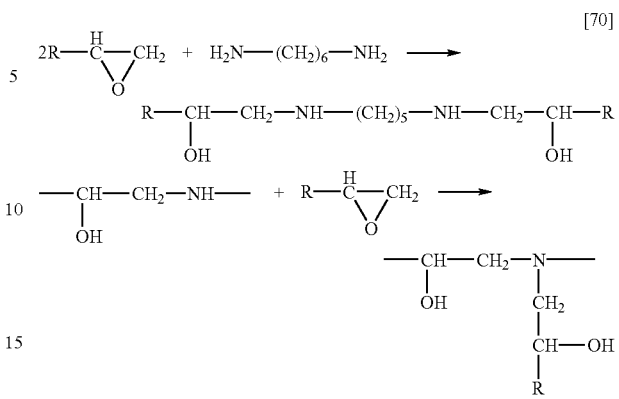

A step of retrieving liposome coated with PHA of the present invention, drying it as needed, or dispersing it in a medium and processing it as a dispersion system can be achieved by appropriately replacing the dispersion medium according to the application of PHA-coated liposome.

When a PHA-coated liposome of the present invention is used, for example, as a liposome for an agricultural chemical composition, the slurry obtained in the preceding step can be directly utilized as an agricultural chemical composition. However, it is preferable to process the slurry so as to make of it a formulation of a more readily usable form such as an aqueous suspension, a hydration agent, powder and granule for usage, in particular, the form of an aqueous suspension. The aqueous suspension is prepared by adding to the slurry obtained as described above a stabilizer such as a puffing agent, an anti-freezing agent, a specific gravity-adjusting agent and an antiseptic agent. Examples of the puffing agent to be used include polysaccharides such as carboxylmethyl cellulose, zantan gum, ramzan gum, locust bean gum, carageenan and weran gum; synthetic polymers such as sodium polyacrylate; mineral fine powders such as aluminium magnesium silicate, smectite, bentonite, hectorite and dry process silica; and alumina sol. Examples of the anti-freezing agents include alcohols such as propylene glycol. Examples of the gravity-adjusting agents include aqueous salts such as sodium sulfate, and urea.

When a PHA-coated liposome of the present invention is used, for example, as a liposome for a fertilizer composition, the slurry obtained in the preceding step can be directly utilized as a fertilizer composition. However, it is preferable to process the slurry so as to make of it a formulation of a more readily usable form such as an aqueous suspension, a hydration agent, powder and granule for usage, in particular, the form of an aqueous suspension. The aqueous suspension is prepared by adding to the slurry obtained as described above a stabilizer such as a puffing agent, an anti-freezing agent, a specific gravity-adjusting agent and an antiseptic agent. Examples of the puffing agent to be used include polysaccharides such as carboxylmethyl cellulose, zantan gum, ramzan gum, locust bean gum, carageenan and weran gum; synthetic polymers such as sodium polyacrylate; mineral fine powders such as aluminium magnesium silicate, smectite, bentonite, hectorite and dry process silica; and alumina sol. Examples of the anti-freezing agents include alcohols such as propylene glycol. Examples of the gravity-adjusting agents include aqueous salts such as sodium sulfate, and urea.

When PHA-coated liposome of the present invention is used, for example, as liposome for a fertilizer composition, the dispersing mekium may be selected from well known cosmetic bases, which are exemplified by the following: hydrocarbons such as solid or liquid paraffin, crystal oil, ceresin, ozokerite and montan wax; plant and animal fats and waxes such as olive, earth wax, carnauba wax, lanolin and spermaceti wax; fatty acids and derivatives thereof such as stearic acid, palmitic acid, oleic acid, glycerol monostearate, glycerol distearate, glycerol monooleate, isopropyl miristate, isopropyl stearate and butyl stearate; silicones such as methypolysiloxanes, methypolycyclosiloxanes, methylphenylpolysiloxanes and silicone polyether copolymers; alcohols such as ethanol, isopropyl alcohol, cetyl alcohol, stearyl alcohol, palmityl alcohol and hexyldodecyl alcohol; and polyalcohols having moisture-keeping action such as glycols, glycerin and sorbitols.

When PHA-coated liposome of the present invention is used, for example, as liposome for an artificial erythrocyte, a slurry obtained in the preceding step is suspended in physiological saline and then large particles therein are removed by well-known means such as the gel filtration method and the centrifuge separation method.

When PHA-coated liposome of the present invention is used, for example, as liposome for ink, it is dispersed in an aqueous medium. For the purpose of supporting dispersion of the cake in water, a surfactant, a protective colloid and a water-soluble organic solvent may be added in amounts not causing significant reduction in resistance of the coating. Also, a preservative, a viscosity modifier, a pH modifier, a chelator and the like may be added.

Specifically, protective colloids that may be added in the liposome for ink include natural proteins such as glue, gelatin, casein, albumin, acacia gum and fish glue, alginic acid, and synthetic polymers such as methylcellulose, carboxymethylcellulose, polyethylene oxide, hydroxyethylcellulose, polyvinyl alcohol, polyacryl amide, aromatic amide, polyacrylic acid, polyvinyl ether, polyvinyl pyrolidone, acryl and polyester.

The protective colloid is used as required for the purpose of improving fixation, viscosity modification and drying properties, and the content of protective colloid in the ink is preferably 30% by mass or lower, particularly preferably 20% by mass or lower.

A surfactant that may be added in the liposome for ink may be any of anionic, cationic, ampholytic and nonionic surfactants. Examples anionic surfactants include fatty esters such as sodium stearate, potassium oleate and semi-curable tallow fatty acid sodium; alkyl sulfates such as sodium dodecyl sulfate, tri(2-hydroxyethyl)ammonium dodecyl sulfate and sodium octadecyl sulfate; benzensulfonates such as sodium nonyl benzanesulfonate, sodium dodecyl benzenesulfonate, sodium otadecyl benzenesulfonate and sodium dodecyl diphenylether disulfonate; naphthalenesulfonates such as sodium dodecyl naphthalenesulfonate and naphthalenesulfonic acid formalin condensates; sulfosuccinates such as sodium didodecyl sulfosuccinate and sodium dioctadodecyl sulfosuccinate; polyoxyethylene sulfates such as sodium polyoxyethylenedodecylether sulfate, tri(2-hydroxyethyl)ammonia polyoxyethylene dodecylether sulfate, sodium polyoxyethylene octadecylether sulfate and sodium polyoxyethylene dodecylphenylether sulfate; and phosphates such as potassium dodecyl phosphate and sodium octadecyl phosphate. Examples of cationic surfactants include alkyl amine salts such as octadecyl ammonium acetate and coconut oil amine acetate; and fourth ammonia salts such as dodecyl trimethyl ammonium chloride, octadecyl trimethyl ammonium chloride, dioctadecyl dimethyl ammonium chloride and dodecyl benzyl dimethyl ammonium chloride. Examples of ampholytic surfactants include alkyl betains such as dodecyl betain and octadodecyl betain; and amine oxides such as dodecyl dimethyl amine oxide. Examples of nonionic surfactants include polyoxyethylene alkyl ethers such as polyoxyethylene dodecyl ether, polyoxyethylene hexadecyl ether, polyoxyethylene octadecyl ether and polyoxyethylene (9-octadecenyl) ether; polyoxyethylene phenyl ethers such as polyoxyethylene octylphenyl ether and polyoxyethylene nonylphenyl ether; oxirane polymers such as polyethylene oxide and copolymer of ethylene oxide and propylene oxide; sorbitan fatty esters such as sorbitan dodecanoic ester, sorbitan hexadecanoic ester, sorbitan octadecanoic ester, sorbitan (9-octadecenoic)ester, sorbitan (9-octadecenoic) triester, polyoxyethylene sorbitan dodekanoic ester, polyoxyethylene sorbitan hexadecanoic ester, polyoxyethylene sorbitan octadecanoic ester, polyoxyethylene sorbitan octanoic triester, polyoxyethylene sorbitan (9-octadecenoic)ester and polyoxyethylene sorbitan (9-octadecenoic)triester; sorbitol fatty esters such as polyoxyethylene sorbitol (9-octadecenoic) tetraester; and glycerin fatty esters such as glycerin octadecanoic ester and glycerin (9-octadecenoic)ester. Of these surfactants, those with HLB larger than or equal to 14 are particularly preferable. The content of the above surfactant for use in the present invention is 0 to 10%, preferably 0 to 5% based on the total amount of water-based ink composition, although it varies depending on whether a single type of surfactant is used or two or more types of surfactants are used in combination.

The polyhydroxyalkanoate-coated liposome of the present invention preferably contains 20 to 95% by mass of water and 1 to 60% by volume of the liposome based on the total amount of the composition.

The present invention will be more specifically described below using Examples. However, each of the Examples that will be described below represents one example of the most preferred embodiments of the present invention, but the technical scope of the present invention should not be limited to these Examples.

REFERENCE EXAMPLE 1

Preparation of Transformant Capable of Producing PHA Synthesizing Enzyme, and Production of PHA Synthesizing Enzyme A transformant capable of producing the PHA synthesizing enzyme was prepared by the following method.

The YN2 strain was cultured on 100 ml of LB culture medium (1% polypeptone, 0.5% yeast extract, 0.5% sodium chloride, pH 7.4) at 30° C. overnight, followed by isolating and collecting chromosome DNA using a method by Marmer, et al. The obtained chromosome DNA was fully decomposed with a restriction enzyme Hind III. pUC18 was as a vector and cleaved by the restriction enzyme Hind III. Dephosphorylation of the terminal (Molecular Cloning, 1, 572, (1989); Cold Spring Harbor Laboratory Press.) was carried out, and thereafter DNA Ligation Kit Ver. 11 (Takara Shuzo Co., Ltd.) was used to couple the cleaved site (cloning site) of the vector to the Hind III fully decomposed fragment of the chromosome DNA. A plasmid vector with this chromosome DNA fragment incorporated therein was used to transform the *Escherichia coli* HB101 strain to prepare a DNA library of the YN2 strain.

Then, for selecting the DNA fragment including the PHA synthesizing enzyme gene of the YN2 strain, a probe for colony hybridization was prepared. Oligonucleotides composed of base sequences of SEQ ID NO: 5 and SEQ ID NO: 6 were synthesized (Amasham Pharmacia•Biotech), and these oligonucleotides were used as primers to carry out PCR with the chromosome DNA as a template. The PCR-amplified DNA fragment was used as a probe. The labeling of the probe was carried out using the commercially available labeling enzyme AlkPhosDirect (Amasham Pharmacia•Biotech). The obtained labeled probe was used to select *Escherichia coli* strains having recombinant plasmids including PHA synthesizing enzyme genes from the chromosome DNA library of YN2 strains by the colony hybridization method. Plasmids were collected from the selected strains by the alkali method, whereby the DNA fragment including the PHA synthesizing enzyme gene can be obtained.

The gene DNA fragment obtained here was recombined into a vector PBBR 122 (Mo Bi Tec) including a broad-host-range replication region belonging to none of Inc P, Inc Q and Inc W constituting an incompatibility group. When this recombinant plasmid was transformed into the *Pseudomonas cichorii* YN2ml strain (strain lacking PHA synthesis capability) by the Electroporation method, PHA synthesizing capability of the YN2ml strain was recovered, thus exhibiting complement property. Thus, it is ensured that the selected gene DNA fragment includes a PHA synthesizing enzyme gene domain capable of being translated into the PHA synthesizing enzyme in *Pseudomonas cichorii* YN2ml strain.

For this DNA fragment including the PHA synthesizing enzyme gene, base sequences were determined by the Sanger's method. As a result, it was found that in the determined base sequences, there existed base sequences expressed by SEQ ID NO: 2 and SEQ ID NO: 4, each coding a peptide. As described below, it could be ensured that the proteins composed of individual peptide chains all had enzyme activity, and the base sequences expressed by SEQ ID NO: 2 and SEQ ID NO: 4 were PHA synthesizing enzymes. Specifically, it was ensured that the base sequence of SEQ ID NO: 2 coded the amino acid sequence expressed by SEQ ID NO: 1, and the base sequence of SEQ ID NO: 4 coded the amino acid sequence expressed by SEQ ID NO: 3, and the PHA synthesis capability can be exhibited with a protein having only any one of these amino acid sequences.

For the PHA synthesizing enzyme gene of base sequence expressed by SEQ ID NO: 2, PCR was carried out with Chromosome DNA as a template to reprepare the full length of the PHA synthesizing enzyme.

For the base sequence expressed by SEQ ID NO: 2, oligonucleotide having base sequences upstream to its initiation codon (SEQ ID NO: 7), which serves as an upstream primer, and oligonucleotide having base sequences downstream to its stop codon (SEQ ID NO: 8), which serves as a downstream primer were designed and synthesized, respectively (Amasham Pharmacia•Biotech). Using these oligonucleotides as primers, PCR was carried out with chromosome DNA as a template to amplify the full length of the PHA synthesizing enzyme gene (LA-PCR Kit; Takara Shuzo Co., Ltd.) In a similar way, for the PHA synthesizing enzyme gene of base sequence expressed by SEQ ID NO: 4, PCR was carried out with Chromosome DNA as a template to reprepare the full length enzyme of the PHA synthesizing enzyme. For the base sequence expressed by SEQ ID NO: 4, oligonucleotide having base sequences upstream to its initiation codon (SEQ ID NO: 9), which serves as an upstream primer, and oligonucleotide having base sequences downstream to its stop codon (SEQ ID NO: 10), which serves as a downstream primer were designed and synthesized, respectively (Amasham Pharmacia•Biotech). Using this oligonucleotide as a primer, PCR was carried out to amplify the full length gene of the PHA synthesizing enzyme (LA-PCR Kit; Takara Shuzo Co., Ltd.)

Then, PCR amplified fragment including the obtained full length gene of PHA synthesizing enzyme were each fully decomposed using the restriction enzyme Hind III. In addition, the expression vector pTrc99A was also cleaved with the restriction enzyme Hind III, and was subjected to dephosphorylation processing (Molecular Cloning, vol. 1, p. 572, 1989; Cold Spring Harbor Laboratory Press). A DNA fragment including the full length gene of the PHA synthesizing enzyme gene with unnecessary base sequences at both terminals removed was coupled to the cleaved site of this expression vector pTrc99A using DNA Ligation Kit Ver. II (Takara Shuzo Co., Ltd.).

*Escherichia coli* (HB101: Takara Shuzo Co., Ltd.) was transformed by a potassium chloride method using the obtained recombinant plasmid. The obtained recombinant was cultured, amplification of recombinant plasmid was carried out, and the recombinant plasmid was collected for each type. The recombinant plasmid retaining gene DNA of SEQ ID NO: 2 was defined as pYN2-C1 (derived from SEQ ID NO: 2), and the recombinant plasmid retaining gene DNA of SEQ ID NO: 4 was defined as pYN2-C2 (derived from SEQ ID NO: 4).

*Escherichia coli* (strain HB101fB, fadB deficient mutant) was transformed by a potassium chloride method using pYN2-C1 and pYN2-C2 to obtain recombinant *Escherichia coil* strains, a pYN2-C1 recombinant strain and a pYN2-C2 recombinant strain each having its own recombinant plasmid.

The pYN2-C1 recombinant strain and pYN2-C2 recombinant strain were each plated in 200 ml of M9 medium containing 0.5% of yeast extract and 0.1% of octanoic acid, and were subjected to shaking culture at 37° C. and 125 strokes/minute. After 24 hours, cells were collected by centrifugation, and plasmid DNA was collected using an ordinary method.

For pYN2-C1, oligonucleotide serving as an upstream primer (SEQ ID NO: 11) and oligonucleotide serving as a downstream primer (SEQ ID NO: 12) were each designed and synthesized (Amasham Pharmacia•Biotech). Using these oligonucleotides as primers, PCR was carried out with pYN2-C1 as a template to amplify the full length gene of the PHA synthesizing enzyme having the BamHI restriction site in the upstream and the XhoI restriction site in the downstream (LA-PCR Kit; Takara Shuzo Co., Ltd.).

In a similar way, for pYN2-C2, oligonucleotide serving as an upstream primer (SEQ ID NO: 13) and oligonucleotide serving as a downstream primer (SEQ ID NO: 14) were each designed and synthesized (Amasham Pharmacia•Biotech). Using this oligonucleotide as a primer, PCR was carried out with pYN2-C2 as a template to amplify the full length gene of the PHA synthesizing enzyme having the BamHI restriction site in the upstream and the XhoI restriction site in the downstream (LA-PCR Kit; Takara Shuzo Co., Ltd.).

Each of purified PCR amplified products was digested by BamHI and XhoI, and was inserted into a corresponding site of plasmid pGEX-6P-1 (manufactured by Amasham Pharmacia•Biotech Co., Ltd.). These vectors were used to transform *Escherichia coli* (JM109) to obtain a strain for expression. The strain was checked with DNA fragments obtained by treating with BamHI and XhoI plasmid DNA prepared in large quantity using Miniprep (Wizard Minipreps DNA Purification Systems, manufactured by PROMEGA Co., Ltd.). The obtained strain was pre-cultured in 10 mL of LB-Amp medium overnight, and thereafter 0.1 mL of the strain was added in 10 mL of LB-Amp medium, and was shaking-cultured at 170 rpm at 37° C. for 3 hours. Thereafter, IPTG was added (at a final concentration of 1 mM), and culture was continuously carried out at 37° C. for 4 to 12 hours.

IPTG-induced *Escherichia coli* was collected (8,000×g, 2 minutes, 4° C.), and was resuspended in 1 ml of PBS at 4° C. The cells were crushed by freezing and thawing and sonication, and were subjected to centrifugation (8,000×g, 10 minutes, 4° C.) to remove cell debris. The presence of desired expression proteins in the supernatant (cell-free extract) was confirmed with SDS-PAGE, followed by purifying the induced and expressed GST fused protein with Glutathion Sepharose 4B beads (manufactured by Amasham Pharmacia•Biotech Co., Ltd.).

The glutathion sepharose for use in the purification was treated in order to avoid nonspecific adsorption in advance. Specifically, the glutathion sepharose was washed three times with the same amount of PBS (8,000×g, 1 minute, 4° C.), and thereafter the same amount of PBS containing 4% BSA was added to treat the glutathion sepharose at 4° C. for 1 hour. After treatment, the glutathion sepharose was washed two times with the same amount of PBS, and was resuspended in ½ in quantity of PBS. 40 μL of pretreated glutathion sepharose was added to 1 mL of cell-free extract and stirred gently at 4° C. Thereby, the fused proteins GST-YN2-C1 and GST-YN2-C2 were adsorbed to glutathion sepharose.

After they were adsorbed, glutathion sepharose was collected by centrifugation (8,000×g, 1 minute, 4° C.), and was washed three times with 400 μL of PBS. Thereafter, 40 μL of 10 mM of reduced glutathion was added, and was stirred at 4° C. for 1 hour to elute the adsorbed fused protein. The supernatant was collected after centrifugation (8,000×g, 2 minutes, 4° C.), and thereafter dialysis was conducted against PBS to purify the GST fused protein. It was confirmed by SDS-PAGE that the protein exhibited a single band.

Five hundred μg of each GST fused protein was digested by PreScission protease (Amasham Pharmacia•Biotech, 5U), and was thereafter passed through glutathion sepharose to remove the protease and GST. Flow-through fractions were further processed with a sephadex G200 column equilibrated with PBS to obtain final purified expression proteins YN2-C1 and Yn2-C2. It was confirmed by SDS-PAGE that they exhibited single bands of 60.8 kDa and 61.5 kDa, respectively.

Each purified enzyme solution was concentrated using a biological solution sample concentrating agent (Mizubutorikun AB-1100, manufactured by Ato Co., Ltd.) to obtain 10 U/ml of purified enzyme solution.

The activity of each purified enzyme was measured by the aforesaid method. Also, the concentrations of proteins in the sample were measured by the Micro BCA protein quantification reagent kit (Pierce Chemical Co., Ltd.). The result of measuring the activity of each purified enzyme is shown in Table 1.

TABLE 1

|  | Activity | Specific Activity |
|---|---|---|
| YN2-C1 | 2.1 U/mL | 4.1 U/mg Protein |
| YN2-C2 | 1.5 U/mL | 3.6 U/mg Protein |

REFERENCE EXAMPLE 2

Production of PHA Synthesizing Enzyme 2

P91, H45, YN2 or P161 strain was plated in the 200 ml of M9 medium containing 0.5% of yeast extract (manufactured by Difco Co., Ltd.) and 0.1% of octanoic acid, and was subjected to shaking culture at 30° C. and 125 strokes/minute. After 24 hours, cells were collected by centrifugation (10,000 ×g, 4° C., 10 minutes), and were resuspended in 200 ml of 0.1 M Tris HCl buffer (pH 8.0) and subjected to centrifugation again, thereby washing the cells. The cells were resuspended in 2.0 ml of 0.1 M Tris HCl buffer (pH 8.0) and crushed by a supersonic crusher, followed by centrifugation (12,000×g, 4° C., 10 minutes) and collection of a supernatant to obtain a crude enzyme. The result of measuring activity of each crude enzyme is shown in Table 2.

TABLE 2

|  | Activity |
|---|---|
| P91 strain | 0.1 U/mL |
| H45 strain | 0.2 U/mL |
| YN2 strain | 0.4 U/mL |
| P161 strain | 0.2 U/mL |

Each enzyme was concentrated using a biological solution sample concentrating agent (Mizubutorikun AB-1100, manufactured by Ato Co., Ltd,) to obtain 10 U/ml of purified enzyme solution.

REFERENCE EXAMPLE 3

Synthesis of 3-hydroxyacyl CoA (R)-3-hydroxyoctanoyl-CoA was synthesized in accordance with the following procedure, based on the method of Rehm BHA, Kruger N, Steinbuchel A (1998) Journal of Biological Chemistry 273 pp 24044–24051, with the method slightly modified. Acyl-CoA synthetase (manufactured by Sigma Co., Ltd.) was dissolved in a tris hydrochloric buffer solution (50 mM, pH 7.5) containing 2 mM ATP, 5 mM $MgCl_2$, 2 mM CoA and 2 mM (R)-3-hydroxyoctanoate so that the concentration was 0.1 milliunit per microliter. The solution was stored in a warm bath at 37° C., and was sampled at appropriate times to analyze the progress of the reaction by HPLC. Sulfuric acid was added in the sampled reaction solution to make a concentration 0.02 N to stop the enzyme reaction, and thereafter (R)-3-hydroxyoctanoate being an unreacted substrate was extracted with n-heptane and removed. For the analysis by HPLC, using a RP18 column (nucleosil C18, 7 μm, Knauser), elution was conducted with the linear concentration gradient of acetonitrile using a 25 mM phosphate buffer solution (pH 5.3) as a mobile phase, and absorption spectra of 200 to 500 nm were monitored by a diode array detector, thereby detecting a thioester compound produced through the enzyme reaction. In a similar way, (R)-3-hydroxy-5-phenylvaleryl CoA, and (R)-3-hydroxy-5-(4-fluorophenyl)valeryl CoA were prepared.

EXAMPLE 1

Ink-encapsulated PHA-coated Liposome

In a 1-litter beaker containing 70 mL of a mixture solution of chloroform and isopropyl ether 1 to 1 ratio, 159.7 mg of dipalmitoylphosphatidylcholine, 172.0 mg of distearylphosphatidylcholine and 168.3 mg of cholesterol (mole ratio of 1:1:2, totaling to 500 mg) were placed. To this solution was added 10 mL of a solution of the water-soluble dye Direct Special Black AXN (available from Nihon Kayaku) and the resultant solution was emulsified by being irradiated with 50 watts of an ultrasonic wave for 30 sec and this operation was repeated 11 times using a probe-type ultrasonic generator (Ohtake) to prepare a w/o emulsion. The emulsion thus prepared was put through a rotary evaporator to remove the organic solvent at 60° C. under diminished pressure, thereby yielding a dye-encapsulated liposome. The degree of vacuum of the evaporator was high at the initial stage, and so the degree was adjusted by lowering it as the evaporation of the organic solvent proceeded so as to prevent bumping. Thereafter, a trace amount of the organic solvent remaining in the dye-encapsulated liposome was further removed by flushing nitrogen gas. An appropriate amount of a 10 mM phosphoric acid buffer solution (pH 7.0) was added to the resulting dye-encapsulated liposome to 30 mL and the resultant was subjected to filtration with a filter of 1.2 μm (Acrodisc, Gelman), followed by dialysis using a dialysis membrane (Spectrapor, Spectrum Medical) in a 10 mM phosphoric acid buffer solution for 24 hours to remove external dye, thereby obtaining a dye-encapsulated liposome. The average particle diameter of the liposome was determined by dynamic light scattering method to be 650 nm.

The PHA synthase YN2-C1 derived from *Pseudomonas cichorii* YN2 prepared in Reference Example 1 was added to the dye-encapsulated liposome (100 U) and the resulting material was allowed to stand at 20° C. for 30 minutes. Then, (R)-3-hydroxyoctanoyl CoA prepared in Reference Example 3 was added to the product so that the final concentration was 5 mM. The synthetic reaction was carried out by incubation at 37° C. for 30 minutes.

The reaction solution was size fractioned by the gel filtration method (Sephadex G-50 column) to yield a PHA-coated liposome. The PHA-coated liposome was determined by dynamic light scattering method and was found to be a monodisperse system with an average particle diameter of 750 nm.

Figure 2:
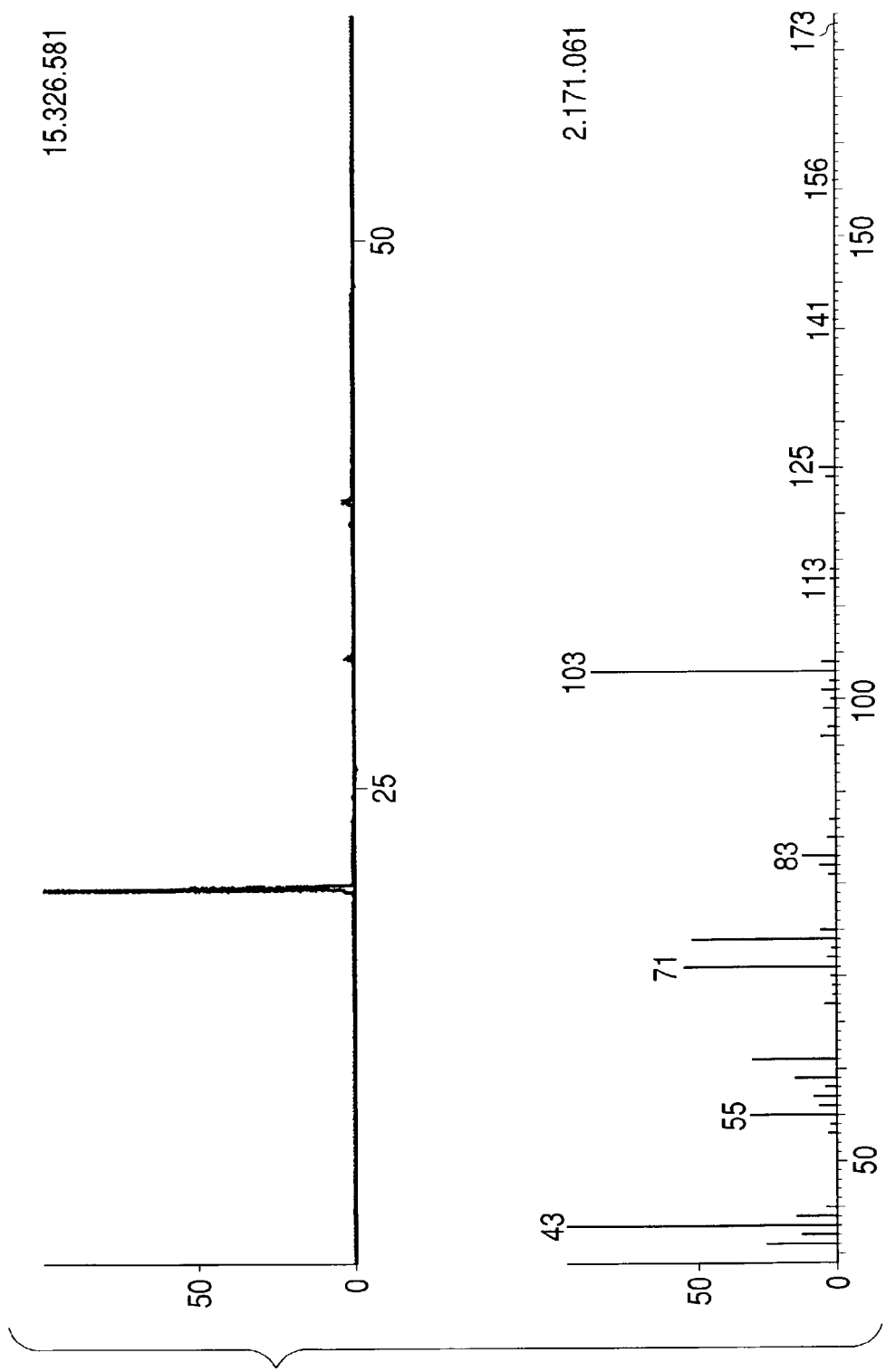
FIG. 2 shows the results by GC-MS analysis of the outer shell of PHA-coated liposome for Example 1.

A part of the prepared PHA-coated liposome was vacuum dried and the resultant was suspended in 20 mL of chloroform and then the suspension was stirred at 60° C. for 20 hours to extract PHA to compose an outer membrane. The extract was subjected to filtration using a membrane filter with a pore diameter of 0.45 μm, followed by concentration by a rotary evaporator under diminished pressure, methanolysis based on a usual method, analysis by gas chromatography and mass spectrometry (GC-MS, Shimadzu QP-5050, EI mode), and subsequent identification of the methyl esterified compound of the PHA monomer unit. As a result, the PHA was identified to be PHA having 3-hydroxyoctanoic acid as the monomer unit, as illustrated in FIG. 2. Further, the molecular weight of the PHA was determined by gel permeation chromatography (GPC: Toso HLC-8020, column: Polymer Laboratory PLgel MIXED-C (5 μm), solvent: chloroform, column temperature: 40° C., in terms of polyethylene) to be Mn=16,000 and Mw=36,000.

EXAMPLE 2

Antibiotic-encapsulated PHA-coated Liposome

Liposome encapsulating vancomycin as an antibiotic was prepared as follows. In 20 mL of chloroform were dissolved 2.1 g of refined yolk lecithin and 0.9 g of cholesterol in an eggplant shape flask. Then, the chloroform was removed using a rotary evaporator, followed by using a vacuum dryer to yield a completely dried membrane component mixture. To this mixture, 20 mL of a 5% glucose aqueous solution and 0.4 g of vancomycin were added and the resulting mixture was dispersed by ultrasonication, followed by freezing and thawing to yield a multi-lamellar vehicle containing vancomycin. The solution was gel filtered on a Sephadex G-50 column to remove the vancomycin that was not encapsulated in the liposome, giving a size-fractioned liposome fraction. The average particle diameter was determined by dynamic light scattering method to be 750 nm.

The PHA synthase YN2-C2 derived from *Pseudomonas cichorii* YN2 prepared in Reference Example 1 was added to the material (100 U) and the resulting material was allowed to stand at 20° C. for 30 minutes. Then, (R)-3-hydroxy-5-phenylvaleryl CoA prepared in Reference Example 3 was added to the product so that the final concentration was 5 mM. The synthetic reaction was carried out by incubation at 37° C. for 30 minutes.

The reaction solution was size fractioned by the gel filtration method (Sephadex G-50 column) to yield PHA-coated liposome. The PHA-coated liposome was determined by dynamic light scattering method and was found to be a monodisperse system with an average particle diameter of 820 nm.

Figure 3:
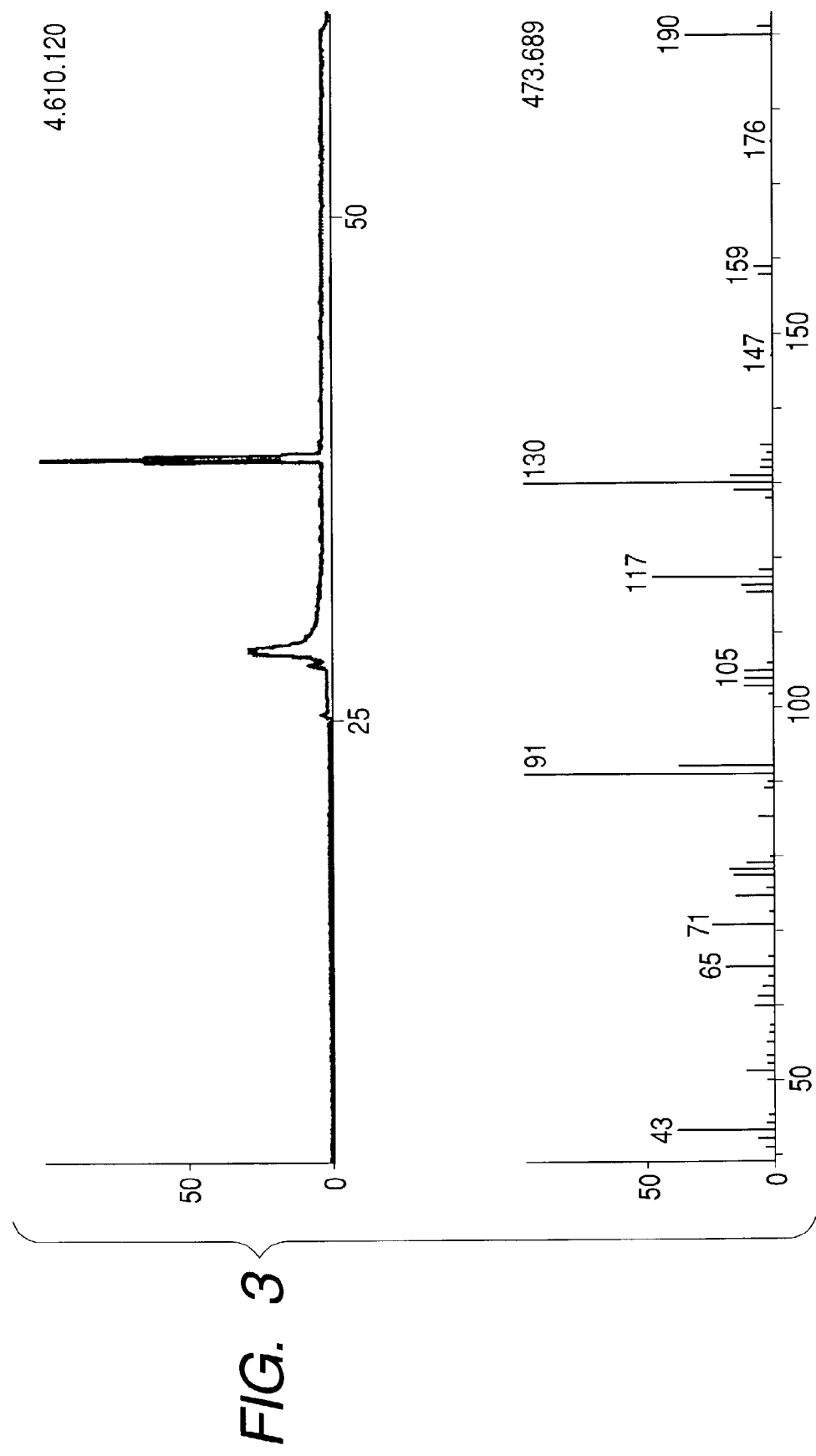
FIG. 3 shows the results by GC-MS analysis of the outer shell of PHA-coated liposome for Example 2.

A part of the prepared PHA-coated liposome was vacuum dried and the resulting material was suspended in 20 mL of chloroform and then the suspension was stirred at 60° C. for 20 hours to extract PHA to compose an outer membrane. The extract was subjected to filtration using a membrane filter with a pore diameter of 0.45 μm, followed by concentration by a rotary evaporator under diminished pressure, methanolysis based on a usual method, analysis by gas chromatography and mass spectrometry (GC-MS, Shimadzu QP-5050, EI mode), and subsequent identification of the methyl esterified compound of the PHA monomer unit. As a result, the PHA was identified to be PHA having 3-hydroxy-5-phenylvaleric acid as the monomer unit, as shown in FIG. 3. Further, the molecular weight of the PHA was determined by gel permeation chromatography (GPC: Toso HLC-8020, column: Polymer Laboratory PLgel MIXED-C (5 μm), solvent: chloroform, column temperature: 40° C., in terms of polyethylene) to be Mn=18,000 and Mw=38,000.

EXAMPLE 3

Agricultural Chemical-encapsulated PHA-coated Liposome

Liposome encapsulating o,o-dimethyl o-(3-methyl-4-nitrophenyl)phosphorothioate as an agricultural chemical active component compound was prepared as follows. In 20 mL of chloroform were dissolved 2.1 g of refined yolk lecithin and 0.9 g of cholesterol in an eggplant shape flask. Then, the chloroform was removed using a rotary evaporator, followed by using a vacuum dryer to yield a completely dried membrane component mixture. To this mixture, 20 mL of a 5% o-(3-methyl-4-nitrophenyl) phosphorothioate aqueous solution was added and the resulting mixture was dispersed by ultrasonication, followed by freezing and thawing to yield a multi-lamellar vehicle containing o-(3-methyl-4-nitrophenyl)phosphorothioate. The solution was gel filtered on a Sephadex G-50 column to remove the o-(3-methyl-4-nitrophenyl)phosphorothioate that was not encapsulated in the liposome, giving a size-fractioned liposome fraction. The average particle diameter was determined by dynamic light scattering method to be 730 nm.

The PHA synthase derived from the P161 strain prepared in Reference Example 2 was added to the material (100 U)

and the resulting material was allowed to stand at 20° C. for 30 minutes. Then, (R)-3-hydroxy-5-(4-fluorophenyl)valeryl CoA prepared in Reference Example 3 was added to the product so that the final concentration was 5 mM. The synthetic reaction was carried out by incubation at 37° C. for 30 minutes.

The reaction solution was size fractioned by the gel filtration method (Sephadex G-50 column) to yield PHA-coated liposome. The PHA-coated liposome was determined by dynamic light scattering method and was found to be a monodisperse system with an average particle diameter of 790 nm.

Figure 4:
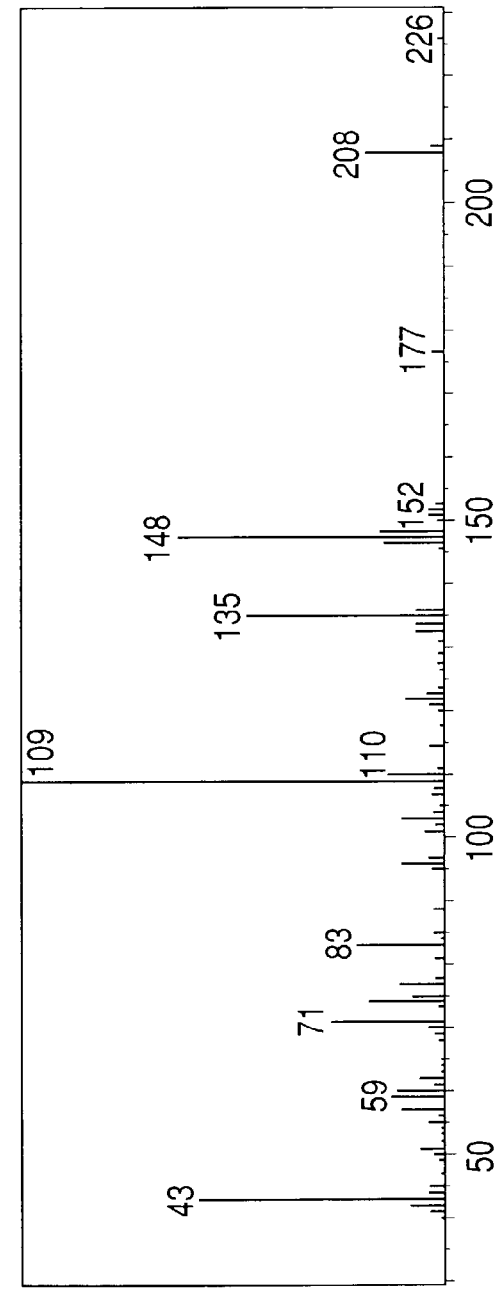
FIG. 4 shows the results by GC-MS analysis of the outer shell of PHA-coated liposome for Example 3.

A part of the prepared PHA-coated liposome was vacuum dried and the resulting material was suspended in 20 mL of chloroform and then the suspension was stirred at 60° C. for 20 hours to extract PHA to compose an outer membrane. The extract was subjected to filtration using a membrane filter with a pore diameter of 0.45 μm, followed by concentration by a rotary evaporator under diminished pressure, methanolysis based on a usual method, analysis by gas chromatography and mass spectrometry (GC-MS, Shimadzu QP-5050, EI mode), and subsequent identification of the methyl esterified compound of the PHA monomer unit. As a result, the PHA was identified to be PHA having (R)-3-hydroxy-5-(4-fluorophenyl)valeric acid as the monomer unit, as shown in FIG. 4. Further, the molecular weight of the PHA was determined by gel permeation chromatography (GPC: Toso HLC-8020, column: Polymer Laboratory PLgel MIXED-C (5 μm), solvent: chloroform, column temperature: 40° C., in terms of polyethylene) to be Mn=15,000 and Mw=35,000.

EXAMPLE 4

Cosmetic-encapsulated PHA-coated Liposome

Liposome encapsulating 2,4-dihydroxybenzophenone, an example of an ultraviolet absorbing agent, as a cosmetic was prepared as follows. In a 1-litter beaker containing 70 mL of a mixture solution of chloroform and isopropyl ether 1 to 1 ratio, 159.7 mg of dipalmitoylphosphatidylcholine, 172.0 mg of distearylphosphatidylcholine and 168.3 mg of cholesterol (mole ratio of 1:1:2, totaling to 500 mg) were placed. To this solution was added 10 mL of a 5% by weight solution of 2,4-dihydroxybenzophenone and the resultant solution was emulsified by being irradiated with 50 watts of an ultrasonic wave for 30 sec 11 times using a probe-type ultrasonic generator (Ohtake) to prepare a w/o emulsion. The emulsion thus prepared was put through a rotary evaporator to remove the organic solvent at 60° C. under diminished pressure, thereby yielding 2,4-dihydroxybenzophenone-encapsulated liposome. The degree of vacuum of the evaporator was high at the initial stage, and so the degree was adjusted by lowering it as the evaporation of the organic solvent proceeded so as to prevent bumping. Thereafter, a trace amount of the organic solvent remaining in the 2,4-dihydroxybenzophenone-encapsulated liposome was further removed by flushing nitrogen gas. An appropriate amount of a 10 mM phosphoric acid buffer solution (pH 7.0) was added to the resulting 2,4-dihydroxybenzophenone-encapsulated liposome to 30 mL and the resultant was subjected to filtration with a filter of 1.2 μm (Acrodisc, Gelman), followed by dialysis using a dialysis membrane (Spectrapor, Spectrum Medical) in a 10 mM phosphoric acid buffer solution for 24 hours to remove external 2,4-dihydroxybenzophenone, thereby obtaining a 2,4-dihydroxybenzophenone-encapsulated liposome. The average particle diameter of the liposome was determined by dynamic light scattering method to be 660 nm.

The PHA synthase derived from the H45 strain prepared in Reference Example 2 was added to the 2,4-dihydroxybenzophenone-encapsulated liposome (100 U) and the resulting material was allowed to stand at 20° C. for 30 minutes. Then, (R)-3-hydroxyoctanoyl CoA prepared in Reference Example 3 was added to the product so that the final concentration was 5 mM. The synthetic reaction was carried out by incubation at 37° C. for 30 minutes.

The reaction solution was size fractioned by the gel filtration method (Sephadex G-50 column) to yield a PHA-coated liposome. The PHA-coated liposome was determined by dynamic light scattering method and was found to be a monodisperse system with an average particle diameter of 730 nm.

A part of the prepared PHA-coated liposome was vacuum dried and the resultant was suspended in 20 mL of chloroform and then the suspension was stirred at 60° C. for 20 hours to extract PHA to compose an outer membrane. The extract was subjected to filtration using a membrane filter with a pore diameter of 0.45 μm, followed by concentration by a rotary evaporator under diminished pressure, methanolysis based on a usual method, analysis by gas chromatography and mass spectrometry (GC-MS, Shimadzu QP-5050, EI mode), and subsequent identification of the methyl esterified compound of the PHA monomer unit. As a result, the PHA was identified to be PHA having 3-hydroxyoctanoic acid as the monomer unit. Further, the molecular weight of the PHA was determined by gel permeation chromatography (GPC: Toso HLC-8020, column: Polymer Laboratory PLgel MIXED-C (5 aim), solvent: chloroform, column temperature: 40° C., in terms of polyethylene) to be Mn=17,000 and Mw=37,000.

EXAMPLE 5

Liposome for Artificial Erythrocyte

Blood (1.5 L) was collected from a vein of a bovine using a blood-collecting bag containing an anticoagulating agent. The collected blood was aseptically transported and kept at 4° C. in a sealed container. The steps below were all carried out aseptically at a low temperature of 4° C. Centrifugal cleaning was conducted by a continuous centrifuge using physiological saline to obtain 500 mL of roughly cleaned erythrocytes as a resultant of removing platelets, leukocytes and plasma from the blood. The erythrocyte was further cleaned by a plasma separator with a pore diameter of 0.45μ using physiological saline. The cleaned erythrocyte was hemolyzed by adding 1 L of pyrogen-free distilled water for 500 mL of the erythrocyte. The erythrocyte was subjected to removal of the erythrocyte membrane and filtration sterilization using a plasma separator with a pore diameter of 0.45μ and a plasma component separator with a pore diameter of 0.1μ. About 1.2 L of erythrocyte membrane-removed hemoglobin of a hemoglobin concentration of 8% (w/w) was obtained. The material was concentrated by ultrafiltration using a dialyzer TAFLOW (cellulose-based hollow dialyzer of Terumo Corp.) for dialysis to give about 180 mL of erythrocyte membrane-removed hemoglobin of a hemoglobin concentration of 50% (w/w).

In chloroform were dissolved 27.76 g of refined phosphatidylcholine of a 80% of hydrogenation rate, 6.96 g of cholesterol, and 3.75 g of refined phosphatidic acid of a 80% of hydrogenation rate. The lipid solution placed in an eggplant shape flask was subjected to chloroform removal by evaporation to thereby form a lipid membrane in the bottom of the eggplant shape flask. Further vacuum drying for 16 hours completely removed the chloroform.

A raw material solution was prepared by adding 180 mL of the erythrocyte membrane-removed hemoglobin to the lipid membrane prepared in the preparation of a liposome forming lipid to yield an emulsion by a Poltex mixer. The raw material was placed a pressure vessel with a narrow-gap nozzle, a Parr cell breaker (available from Parr Corp., U.S.); nitrogen gas was introduced into it and pressure was applied to 130 Kg/cm$^2$. It was allowed to stand for 30 minutes to sufficiently penetrate nitrogen gas into the raw material solution. Then, the valve of the nozzle was gradually opened to eject the raw material with the pressure maintained at 130 Kg/cm$^2$.

The fluid subsequent to the pressure ejection was fractioned by gel filtration (Sephadex G-50 column) to remove the hemoglobin that was not encapsulated in the liposome, thereby obtaining hemoglobin-encapsulated liposome.

The PHA synthase YN2-C1 derived from *Pseudomonas cichorii* prepared in Reference Example 1 was added to the hemoglobin-encapsulated liposome (100 U) and the resulting material was allowed to stand at 20° C. for 30 minutes. Then, (R)-3-hydroxyoctanoyl CoA prepared in Reference Example 3 was added to the product so that the final concentration was 5 mM. The synthetic reaction was carried out by incubation at 37° C. for 30 minutes.

The reaction solution was size fractioned by the gel filtration method (Sephadex G-50 column) to yield PHA-coated liposome. The PHA-coated liposome was determined by dynamic light scattering method and was found to be a monodisperse system with an average particle diameter of 720 nm.

A part of the prepared PHA-coated liposome was vacuum dried and the resultant was suspended in 20 mL of chloroform and then the suspension was stirred at 60° C. for 20 hours to extract PHA to compose an outer membrane. The extract was subjected to filtration using a membrane filter with a pore diameter of 0.45 µm, followed by concentration by a rotary evaporator under diminished pressure, methanolysis based on a usual method, analysis by gas chromatography and mass spectrometry (GC-MS, Shimadzu QP-5050, EI mode), and subsequent identification of the methyl esterified compound of the PHA monomer unit. As a result, the PHA was identified to be PHA having 3-hydroxyoctanoic acid as the monomer unit. Further, the molecular weight of the PHA was determined by gel permeation chromatography (GPC: Toso HLC-8020, column: Polymer Laboratory PLgel MIXED-C (5 µm), solvent: chloroform, column temperature: 40° C., in terms of polyethylene) to be Mn=17,000 and Mw=37,000.

EXAMPLE 6

Controlled Releasability of Calcein-encapsulated PHA-coated Liposome

In a 1-litter beaker containing 70 mL of a mixture solution of chloroform and isopropyl ether 1 to 1 ratio, 500 mg of dipalmitoylphosphatidylcholine was placed. To this solution was added 10 mL of an aqueous solution of the fluorescent aqueous compound Calcein and the resultant solution was emulsified by being irradiated with 50 watts of an ultrasonic wave for 30 sec 11 times using a probe-type ultrasonic generator (Ohtake) to prepare a w/o emulsion. The emulsion thus prepared was put through a rotary evaporator to remove the organic solvent at 60° C. under diminished pressure, thereby yielding Calcein-encapsulated liposome. The degree of vacuum of the evaporator was high at the initial stage, and so the degree was adjusted by lowering it as the evaporation of the organic solvent proceeded so as to prevent bumping. Thereafter, a trace amount of the organic solvent remaining in the Calcein-encapsulated liposome was further removed by flushing nitrogen gas. An appropriate amount of a 10 mM phosphoric acid buffer solution (pH 7.0) was added to the resulting Calcein-encapsulated liposome to 30 mL and the resultant was subjected to filtration with a filter of 1.2 µm (Acrodisc, Gelman) to thereby obtain liposome, Calcein being encapsulated inside thereof.

The PHA synthase YN2-C1 derived from *Pseudomonas cichorii* YN2 prepared in Reference Example 1 was added to part of the Calcein-encapsulated liposome (100 U) and the resulting material was allowed to stand at 20° C. for 30 minutes. Then, (R)-3-hydroxyoctanoyl CoA prepared in Reference Example 3 was added to the product so that the final concentration was 5 mM. The synthetic reaction was carried out by incubation at 20° C. for 90 minutes.

The reaction solution was size fractioned by the gel filtration method (Sephadex G-50 column) to yield a PHA-coated liposome.

Figure 5:
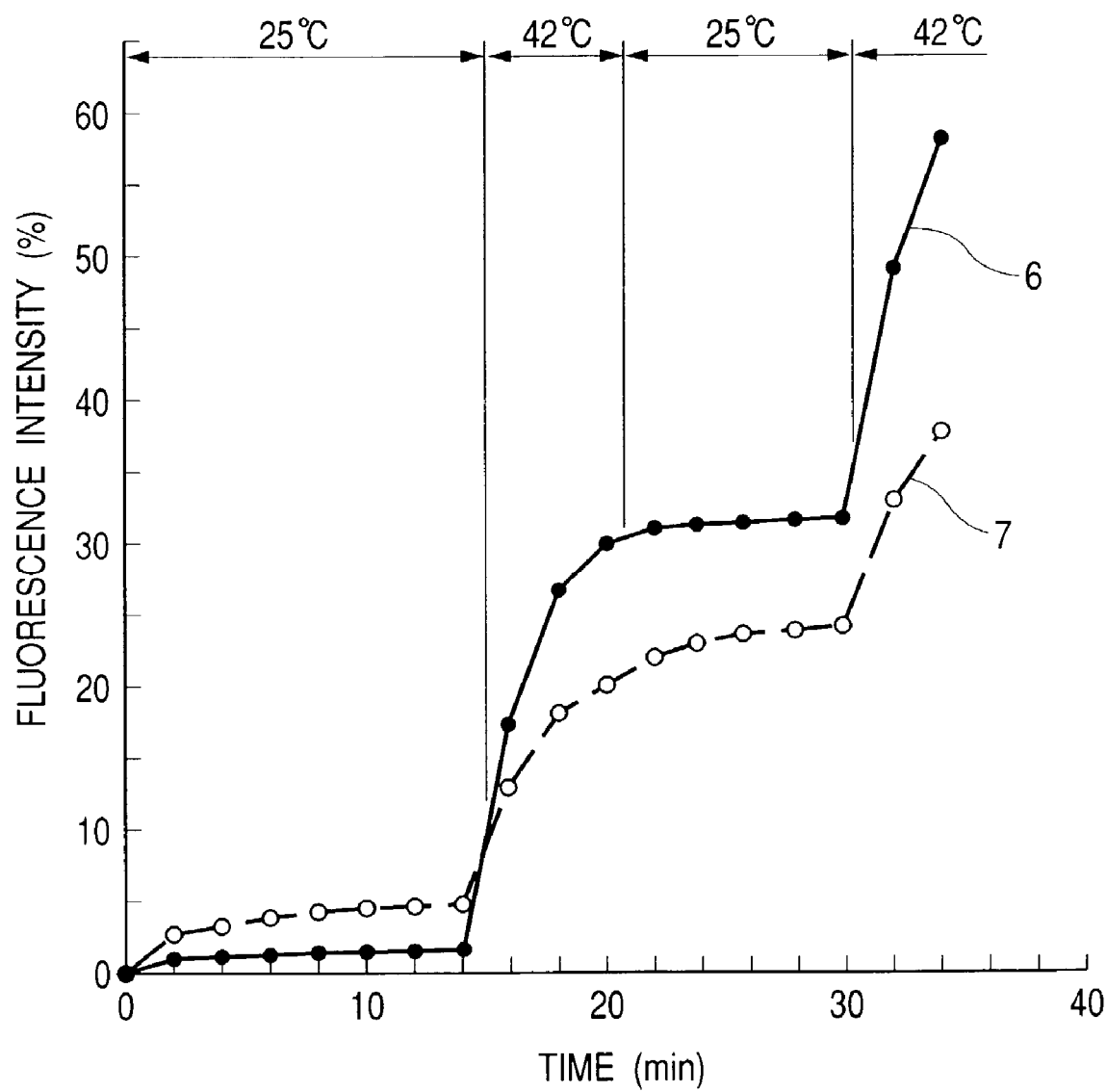
FIG. 5 shows as a function of time the release behaviors of Calcein from PHA-coated liposome and liposome without PHA at 25° C. and 42° C. in Example 6.

Calcein release from the PHA-coated liposome and a liposome not coated with PHA was determined by measuring the intensity of fluorescence for Calcein. The results are shown in FIG. 5. In FIG. 5, the numeral 6 designates the behavior of releasing Calcein from the polyhydroxyalkanoate-coated liposome; and numeral 7 designates the behavior of releasing Calcein from the liposome not coated with polyhydroxyalkanoate.

For sustained release capacity of a phospholipid membrane at a temperature (25° C.) lower that that of the phase transition temperature, the PHA-coated liposome (6) was excellent in holding ability compared with the liposome not coated with PHA (7). With sustained release capacity of a phospholipid membrane at the phase transition temperature (about 42° C.), the PHA-coated liposome (6) showed rapid release properties as compared with the liposome not coated with PHA (7). When the temperature was returned to 25° C. again, the release capacity of the PHA-coated liposome was restrained.

Thus, it has been shown that the PHA-coated liposome of this Example is improved in sustained release temperature susceptibility as compared with liposome not coated with PHA. The improvement of the holding ability at room temperature (25° C.) seems to be due to the restraint of leakage of contents from the liposome attributable to the osmotic pressure difference between the outside and inside of the liposome because of the large mechanical strength of the coating PHA. On the other hand, the reason of the improvement in release capacity at the phase transition temperature appears to be because the osmotic pressure difference in the PHA-coated liposome is kept to be large relative to that for the liposome not coated with PHA, and so this osmotic pressure difference drives the leakage of the contents to be accelerated, thus resulting in rapid penetration of the contents due to the outer shell of PHA being porous.

EXAMPLE 7

Polyhydroxyalkanoate-coated Liposome with Gradient Structure

In a 1-litter beaker containing 70 mL of a mixture solution of chloroform and isopropyl ether 1 to 1 ratio, 500 mg of dipalmitoylphosphatidylcholine was placed. To this solution was added 10 mL of an aqueous solution of the fluorescent compound Calcein and the resultant solution was emulsified by being irradiated with 50 watts of an ultrasonic wave for 30 sec 11 times using a probe-type ultrasonic generator (Ohtake) to prepare w/o emulsion. The emulsion thus prepared was put through a rotary evaporator to remove the organic solvent at 60° C. under diminished pressure, thereby yielding a Calcein-encapsulated liposome. The degree of vacuum of the evaporator was high at the initial stage, and so the degree was adjusted by lowering it as the evaporation of the organic solvent proceeded so as to prevent bumping. Thereafter, a trace amount of the organic solvent remaining in the Calcein-encapsulated liposome was further removed by flushing nitrogen gas. An appropriate amount of a 10 mM phosphoric acid buffer solution (pH 7.0) was added to the resulting Calcein-encapsulated liposome to 30 mL and the resultant was subjected to filtration with a filter of 1.2 μm (Acrodisc, Gelman) to thereby obtain liposome, Calcein being encapsulated inside thereof.

The PHA synthase YN2-C1 derived from *Pseudomonas cichorii* YN2 prepared in Reference Example 1 was added to part of the Calcein-encapsulated liposome (100 U) and the resulting solution was gently agitated at 20° C. for 30 minutes to fix the PHA synthesis enzyme on the surface of the liposome.

The resulting material was size fractioned by gel filtration (Sephadex G-50 column) to yield a synthesis enzyme-fixed liposome fraction. To the aforementioned synthesis enzyme-fixed liposome was added 100 parts by weight of 0.1 M phosphoric acid buffer (pH 7.0) containing 30 mM (R)-3-hydroxyoctanoil CoA (prepared by the method indicated in Eur. J. Biochem., 250, 432–439 (1997)) and 0.1% bovine serum albumin (available from Sigma Chemical Corp.). Then, to this reaction solution was added, with the solution being kept in gentle agitation at 30° C., 0.1 M phosphoric acid buffer (pH 7.0) containing 30 mM (R)-3-hydroxypimelyl CoA (prepared by the method indicated in J. Bacteriol., 182, 2753–2760 (2000)) and 0.1% bovine serum albumin (available from Sigma Corp.) using a microtube pump (MP-3N, available from Tokyo Rikakikai Co., Ltd.) at a rate of 25 parts by weight per minute.

After 30-munite shaking, the resulting solution was subjected to washing with 0.1 M phosphoric acid buffer (pH 7.0) to remove unreacted substances, etc., followed by air drying, thereby obtaining liposome coated with polyhydroxyalkanoate.

After this polyhydroxyalkanoate-coated liposome was freeze-dried, the molecular weight of the polymer formed on the surface thereof was determined by a time-of-flight secondary ion mass spectrometer (TOF-SIMS IV, available from CAMECA). The obtained mass spectrum showed that the surface of the polyhydroxyalkanoate-coated liposome is made up of a copolymer of 3-hydroxypimelic acid and 3-hydroxyoctanoic acid (mole ratio of 17:1). In addition, as the surface of the polyhydroxyalkanoate-coated liposome was shaved piece by piece and the mass spectrum was similarly measured by TOF-SIMS, the composition ratio of 3-hydroxypimelic acid of the aforementioned copolymer gradually decreased and the composition ratio of 3-hydroxyoctanoic acid increased. This showed that the surface of the polyhydroxyalkanoate-coated liposome of the Example is coated with polyhydroxypimelate having hydrophilic functional groups, that the layer just below the surface is coated with a copolymer of 3-hydroxypimelic acid having hydrophilic functional groups and 3-hydroxyoctanoic acid having hydrophobic functional groups, and that the liposome is made up of a gradient structure in which as the layer becomes lower, the composition ratio of 3-hydroxyoctanoic acid increases.

Further, the molecular weight of the PHA was determined by gel permeation chromatography (GPC: Toso HLC-8020, column: Polymer Laboratory PLgel MIXED-C (5 μm), solvent: chloroform, column temperature: 40° C., in terms of polyethylene) to be Mn=21,000 and Mw=40,000.

EXAMPLE 8

Preparation of Polyhydroxyalkanoate-coated Liposome (Chemical Modification)

As with Example 7, enzyme-fixed liposome was prepared by encapsulating Calcein therein and immobilizing on the surface thereof the PHA synthase YN2-C1 derived from *Pseudomonas cichorii* YN2 prepared in Reference Example 1.

One part by weight of the aforementioned enzyme-fixed liposome was suspended in 48 parts by weight of 0.1 M phosphoric acid buffer (pH 7.0) and to this suspension were added 0.8 part by weight of (R, S)-3-hydroxy-5-phenoxyvaleryl CoA which had been prepared by hydrolyzing 3-hydroxy-5-phenoxyvalerate obtained from the Reformatsky reaction of 3-phenoxypropanol and bromoacetate to yield 3-hydroxy-5-phenoxyvaleric acid, followed by the process described in Eur. J. Biochem., 250, 432–439 (1997), 0.2 part by weight of (R, S)-3-hydroxy-7,8-epoxyoctanoil CoA which had been prepared by epoxidizing the unsaturated part of 3-hydroxy-7-octenoic acid synthesized by the process described in Int. J. Biol. Macromol., 12, 85–91 (1990) with 3-chlorobenzoic acid, followed by the process described in Eur. J. Biochem., 250, 432–439 (1997), and 0.1 part by weight of bovine serum albumin (Sigma Chemical Corp.) and then the resulting solution was gently agitated at 30° C. for 2 hours to yield Sample 1.

As Comparative Reference, Sample 2 was obtained by the same method described above except that (R, S)-3-hydroxy-7,8-epoxyoctanoil CoA was replaced with 3-hydroxyoctanoil CoA.

Ten μL of the above Samples was placed on a slide glass and to this was added 10 μL of a 1% Nile Blue A aqueous solution. The resultant solution was subjected to mixing on the slide glass, placing of a cover glass thereon and subsequent fluorescence microscope observation (330 to 380 nm excitation filter, 420 nm long pass absorption filter; available from Nikon Corp.). As a consequence, all of the Samples displayed the emission of fluorescence from the surface of the liposome. Therefore, the liposome was shown to be coated with PHA on the surface thereof.

As a control, 1 part by weight of liposome not coated with polyhydroxyalkanoate was added to 49 parts by weight of 0.1 M phosphoric acid buffer (pH 7.0) and this solution was gently agitated at 30° C. for 2.5 hours and then was similarly subjected to fluorescence microscope observation. As a result, no fluorescence was emitted from the surface of the liposome at all.

Further, PHA to be the outer membrane was obtained by a method that includes retrieving part of the Sample by centrifugation (10,000 ×g, 4° C., for 10 min), vacuum drying the substance, suspending it in chloroform, agitating the suspension at 60° C. for 20 hours and subsequently extracting it. This extract was analyzed by $^1$H NMR (apparatus used: FT-NMR, Bruker DPX400, nuclear species: $^1$H, solvent used: deuterated chloroform (including TMS)). Percentages of side chain units calculated from the results are given in Table 3.

TABLE 3

Composition of the outer shell PHA of capsule structures ($^1$H NMR, unit %)

| Monomer unit | Sample 1 | Sample 2 |
|---|---|---|
| 3-hydroxy-5-phenoxyvaleric acid | 84% | 76% |
| 3-hydroxy-7,8-epoxyoctanoic acid | 16% | — |
| 3-hydroxyoctanoic acid | — | 24% |

Fifty parts by weight of Sample 1 indicated above was centrifuged (10,000×g, 4° C., for 10 min) to recover polyhydroxyalkanoate-coated liposome. The resulting liposome was suspended in 50 parts by weight of purified water and the operation was repeated three times. In this suspension was dissolved 0.5 part by weight of hexamethylenediamine as the crosslinking agent. After confirmation of the dissolution, the water was removed by freeze drying (Sample 3). Further, Sample 3 was allowed to react at 70° C. for 12 hours (Sample 4).

Samples 3 and 4 mentioned above were suspended in chloroform and the resulting suspension was stirred at 60° C. for 20 hours and then PHA to be the outer shell was extracted. After removal of the chloroform by vacuum drying, the PHA was measured by a differential scanning calorimeter (DSC: Perkin Elmer; pyris 1, rate of raising temperature: 10° C./min). The results showed that Sample 3 displayed a distinct exothermal peak near 90° C., indicating that epoxy groups in the polymer reacts with hexamethylenediamine to allow crosslinking of the polymers to each other to proceed. On the other hand, Sample 4 did not show a clear heat flow, suggesting that the crosslinking reaction had almost completed.

Further, for the same Samples, infrared spectra were measured (FT-IR: Perkin Elmer 1720X). As a result, peaks attributable to amines (near 3340 cm$^{-1}$) and epoxy groups (near 822 cm$^{-1}$), which were seen in Sample 3, did not appear for Sample 4.

In conclusion, it has been shown that the PHA having epoxy units on side chains thereof is made to react with hexamethylenediamine to yield a crosslinked polymer.

On the other hand, Sample 2 as a comparative reference was similarly evaluated; however, the results that clearly show crosslinking of polymers to each other like the above results were not obtained.

The present invention has been described in detail with respect to preferred embodiments, and it will now be that changed and modifications may be made without departing from the invention in its broader aspects, and it is the intention, therefore, in the appended claims to cover all such changes and modifications as fall within the true spirit of the invention.

What is claimed is:

1. A liposome having an outer wall, which is at least partially coated with a polyhydroxyalkanoate, wherein a portion of the liposome coated with the polyhydroxyalkanoate is hydrophilic, and wherein the liposome contains a substance other than a lipid inside a portion surrounded by the outer wall.

2. The polyhydroxyalkanoate-coated liposome according to claim 1, wherein said polyhydroxyalkanoate is comprised of at least one selected from the group consisting of monomer units expressed by Formulas [1] to [10]:

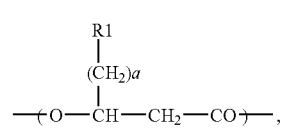

[1]

wherein symbol "a" represents an integer, and the combination of R1 and "a" is selected from the group consisting of a combination of a hydrogen atom and any one integer selected from the group consisting of 0 to 10;

a combination of a halogen atom and any one integer selected from the group consisting of 1 to 10;

a combination of a chromophoric group and any one integer selected from the group consisting of 1 to 10;

a combination of a carboxyl group or a salt thereof and any one integer selected from the group consisting of 1 to 10; and a combination of

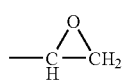

and any one integer selected from the group consisting of 1 to 7;

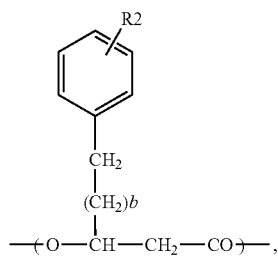

[2]

wherein b represents any one integer selected from the group consisting of 0 to 7, and R2 is selected from the group consisting of a hydrogen atom (H), a halogen atom, —CN, —NO$_2$, —CF$_3$, —C$_2$F$_5$ and —C$_3$F$_7$;

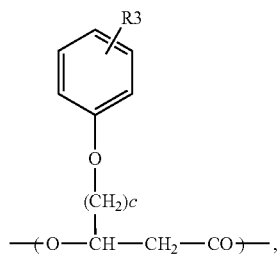

[3]

wherein c represents any one integer selected from the group consisting of 1 to 8, and R3 is selected from the group consisting of a hydrogen atom (H), a halogen atom, —CN, —NO$_2$, —CF$_3$, —C$_2$F$_5$ and —C$_3$F$_7$;

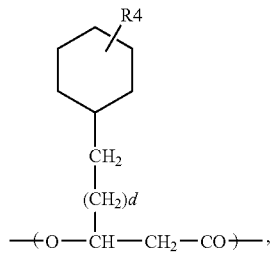

[4]

wherein d represents any one integer selected from the group consisting of 0 to 7, and R4 is selected from the group consisting of a hydrogen atom (H), a halogen atom, —CN, —NO$_2$, —CF$_3$, —C$_2$F$_5$ and —C$_3$F$_7$;

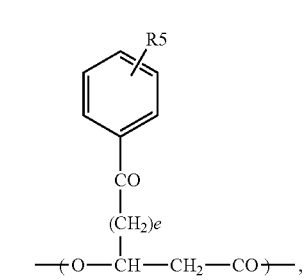

[5]

wherein e represents any one integer selected from the group consisting of 1 to 8, and R5 is selected from the group consisting of a hydrogen atom (H), a halogen atom, —CN, —NO$_2$, —CF$_3$, —C$_2$F$_5$, —C$_3$F$_7$, —CH$_3$, —C$_2$H$_5$ and —C$_3$H$_7$;

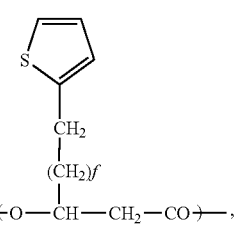

[6]

wherein f represents any one integer selected from the group consisting of 0 to 7;

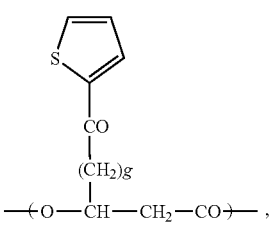

[7]

wherein g represents any one integer selected from the group consisting of 1 to 8;

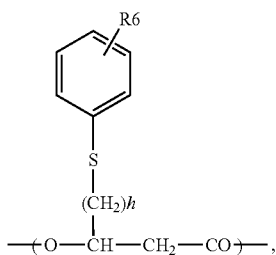

wherein h represents any one integer selected from the group consisting of 1 to 7, and R6 is selected from the group consisting of a hydrogen atom (H), a halogen atom, —CN, —NO₂, —COOR', —SO₂R'', —CH₃, —C₂H₅, —C₃H₇, —CH(CH₃)₂ and —C(CH₃)₃, wherein R' is selected from the group consisting of a hydrogen atom (H), Na, K, —CH₃ and —C₂H₅, and R'' is selected from the group consisting of —OH, ONa, —OK, a halogen atom, —OCH₃ and —OC₂H₅;

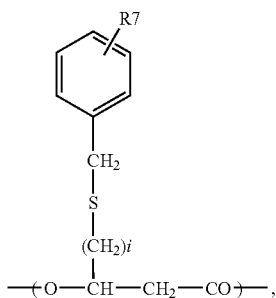

wherein i represents any one integer selected from the group consisting of 1 to 7, and R7 is selected from the group consisting of a hydrogen atom (H), a halogen atom, —CN, —NO₂, —COOR'and —SO₂R'', wherein R' is selected from the group consisting of a hydrogen atom (H), Na, K, —CH₃ and —C₂H₅, and R'' is selected from the group consisting of —OH, ONa, —OK, a halogen atom, —OCH₃ and —OC₂H₅; and

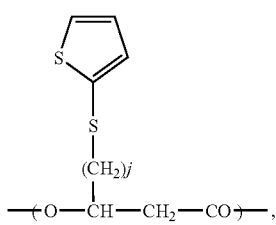

wherein j represents any one integer selected from the group consisting of 1 to 9.

3. The polyhydroxyalkanoate-coated liposome according to claim 1, wherein the polyhydroxyalkanoate has a hydrophilic functional group.

4. The polyhydroxyalkanoate-coated liposome according to claim 3, wherein the polyhydroxyalkanoate has an anionic functional group.

5. The polyhydroxyalkanoate-coated liposome according to claim 4, wherein the polyhydroxyalkanoate has a carboxyl group.

6. The polyhydroxyalkanoate-coated liposome according to claim 5, wherein the monomer unit having a carboxyl group is at least one selected from the group consisting of monomer units represented by Formula [11]

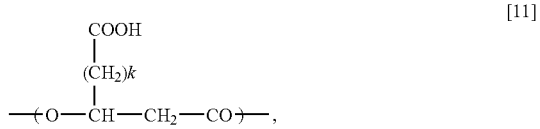

wherein k is an integer of any one of 1 to 10.

7. The polyhydroxyalkanoate-coated liposome according to claim 1, wherein a monomer unit composition of said polyhydroxyalkanoate varies in a direction in which said polyhydroxyalkanoate is laminated onto the liposome.

8. The polyhydroxyalkanoate-coated liposome according to claim 1, wherein at least a part of said polyhydroxyalkanoate is chemically modified.

9. The polyhydroxyalkanoate-coated liposome according to claim 8, wherein said chemically modified polyhydroxyalkanoate has at least a graft chain.

10. The polyhydroxyalkanoate-coated liposome according to claim 9, wherein said graft chain is formed by chemical modification of polyhydroxyalkanoate containing at least a monomer unit having an epoxy group.

11. The polyhydroxyalkanoate-coated liposome according to claim 9, wherein said graft chain is a graft chain of compounds each of which has an amino group.

12. The polyhydroxyalkanoate-coated liposome according to claim 11, wherein said compound having an amino group is an amino-terminal-modified compound.

13. The polyhydroxyalkanoate-coated liposome according to claim 12, wherein each of said amino-terminal-modified compounds is independently selected from the group consisting of polyvinyl amine, polyethylene imine and amino-terminal-modified polysiloxane.

14. The polyhydroxyalkanoate-coated liposome according to claim 8, wherein at least a part of said polyhydroxyalkanoate is crosslinked.

15. The polyhydroxyalkanoate-coated liposome according to claim 14, wherein said crosslinked polyhydroxyalkanoate is a polyhydroxyalkanoate in which a polyhydroxyalkanoate containing at least a monomer unit having an epoxy group is crosslinked.

16. The polyhydroxyalkanoate-coated liposome according to claim 14, wherein said crosslinked polyhydroxyalkanoate is a polyhydroxyalkanoate crosslinked with at least one selected from the group consisting of a diamine compound, succinic anhydride, 2-ethyl-4-methylimidazole and irradiation of electron ray.

17. The polyhydroxyalkanoate-coated liposome according to claim 16, wherein said diamine compound is hexamethylenediamine.

18. The polyhydroxyalkanoate-coated liposome according to claim 1, wherein the substance is a pigment suspension, a dye, an agricultural chemical component, hemoglobin, a cosmetic component, a fertilizer component or a pharmaceutically effective component.

19. The polyhydroxyalkanoate-coated liposome according to claim 1, wherein a number-average molecular weight of the polyhydroxyalkanoate ranges from 1,000 to 10,000,000.

20. The polyhydroxyalkanoate-coated liposome according to claim 19, wherein the number-average molecular weight of the polyhydroxyalkanoate ranges from 3,000 to 1,000,000.

21. The polyhydroxyalkanoate-coated liposome according to claim 1, wherein the substance is water-soluble.

22. The polyhydroxyalkanoate-coated liposome according to claim 1, wherein the substance is lipo-soluble.

* * * * *

UNITED STATES PATENT AND TRADEMARK OFFICE
CERTIFICATE OF CORRECTION

PATENT NO.         : 7,186,459 B2
APPLICATION NO. : 10/190490
DATED                  : March 6, 2007
INVENTOR(S)        : Tsuyoshi Nomoto et al.

It is certified that error appears in the above-identified patent and that said Letters Patent is hereby corrected as shown below:

COLUMN 1:

Line 10, "releasability" should read --release ability--;
Line 14, "Liposome," should read --A liposome,--;
Line 15, "extremely close proximity to" should read --extremely similar to a--;
Line 16, "structure as a model" should read --structure--;
Line 17, "substance" should read --substance,--;
Line 21, "expected" should read --expected to be used--;
Line 22, "components having a problem in" should read --components, which have a problem with--;
Line 23, "ity to an affected part and controls gradual releasability." should read --ity, to an affected area and controls gradual release of the components.--;
Line 24, "Liposome finds" should read --Liposomes find--;
Line 25, "but its fragility in" should read --but fragility of their--;
Line 26, "been pointed out." should read --been identified.--;
Line 27, "of" should read --in--;
Line 29, "tained" should read --tained.-- and "and" should read --. Therefore--;
Line 30, "Conventionally," should read --Conventional--;
Line 31, "are known that" should be deleted;
Line 34, "oxidation of" should read --oxidation of an--;
Line 36, "Furthermore," should read --Furthermore, a--;
Line 39, "releas-" should read --release--;
Line 40, "ability" should be deleted;
Line 41, "of" should read --of a--;
Line 43, "control gradual releasability" should read --control the gradual release--;
Line 50, "proposed" should read --proposed a--; and
Line 56, "than" should read --than a--.

COLUMN 2:

Line 5, "has" should read --is--,
Line 6, "biodegradability" should read --biodegradable--;
Line 9, "control of gradual releasability." should read --controlling gradual release.--;
Line 16, "releasability of" should read --releasing ability of a--;
Line 20, "releasability" should read --release of the substances.--;
Line 27, "of lipid, particularly" should read --of a lipid, particularly a-- and "both" should read --both a--;
Line 28, "lipid and" should read --lipid and a--;
Line 29, "methods as its preparation process." should read --methods.--;
Line 32, "in the inside of" should read --inside the--;

UNITED STATES PATENT AND TRADEMARK OFFICE
CERTIFICATE OF CORRECTION

PATENT NO. : 7,186,459 B2
APPLICATION NO. : 10/190490
DATED : March 6, 2007
INVENTOR(S) : Tsuyoshi Nomoto et al.

It is certified that error appears in the above-identified patent and that said Letters Patent is hereby corrected as shown below:

(COLUMN 2 Continued:)

Line 33, "material in the membrane of" should read --material is in the membrane of the--;
Line 35, "of" should read --of the--;
Line 51, "to" should read --on--;
Line 53, "the fact that the above case," should read --case. The inventors also found that--;
Line 54, "with" should read --with a biodegradable, non-toxic-- and "having biodegradabil-" should be deleted;
Line 55, "ity and no toxicity" should be deleted;
Line 56, "therefor, and further the fact" should read --therefore. Further, the inventors found--;
Line 58, "controllableness of sustained releasability" should read --control of sustained releasing ability--;
Line 64, "a characteristic of" should be deleted; and
Line 65, "wall being" should read --wall of the liposome--.

COLUMN 3:

Line 6, "than" should read --than a--,
Line 8, "invention" should read --invention,--;
Line 18, "all the" should read --the entire--;
Line 19, "coated so far" should read --coated, as long--;
Line 24, "is comprised in" should read --comprises--;
Line 25, "is" should be deleted;
Line 26, "excellent in" should read --has excellent--;
Line 27, "releasability" should read --release--;
Line 29, "applications" should read --applications,--
Line 58, "more in" should read --in more--;
Line 60, "Liposome" should read --A liposome,--; and
Line 64, "This is, phospholipids" should read --Phospholipids--.

COLUMN 4:

Line 6, "available." should read --obtained.--;
Line 12, "cholesteral: phospholipid can be illustrated to be" should read --cholesteral to a phospholipid can be, for example,--;
Line 13, "from" should be deleted;
Line 16, "of" should read --of a-- and "well known" should read --well-known--;

UNITED STATES PATENT AND TRADEMARK OFFICE
CERTIFICATE OF CORRECTION

PATENT NO. : 7,186,459 B2
APPLICATION NO. : 10/190490
DATED : March 6, 2007
INVENTOR(S) : Tsuyoshi Nomoto et al.

It is certified that error appears in the above-identified patent and that said Letters Patent is hereby corrected as shown below:

(COLUMN 4 Continued:)

Line 35, "of" should read --of a--;
Line 37, "kid" should read --kit,--;
Line 38, "Liposome prepared by these well known" should read --Liposomes prepared by these well-known--;
Line 39, "can be all supplied to" should read --can all be used in--;
Line 40, "producing" should read --producing a--;
Line 42, "solvent" should read --solvent,--;
Line 45, "in" should read --at--;
Line 56, "while," should read --time,--;
Line 64, "30 nm" should read --30 nm--; and
Line 65, "eventually." should be deleted.

COLUMN 5:

Line 1, "like" should read --like.--;
Line 2, "and not to excessively increase temperature." should read --The temperature should not be excessively increased.--;
Line 3, "preparing" should read --preparing a--;
Line 5, "into a" should read --into an--;
Line 7, "Lipo-" should read --A lipo- --,
Line 9, "Liposome" should read --A liposome--,
Line 11, "and" should read --and a--;
Line 15, "operation such as by ultrafiltration" should read --operation, such as ultrafiltration,--;
Line 16, "of the" should read --in that--;
Line 17, "ethanol not being removed completely" should read --ethanol may not be completely removed--;
Line 18, "preparing" should read --preparing a--;
Line 22, "form" should read --form a--;
Line 27, "forms" should read --results in the formation of--;
Line 29, "preparing" should read --preparing a--;
Line 38, "preparing" should read --preparing a--;
Line 39, "or" should read --or a--;
Line 42, "surfactant" should read --surfactant,--;
Line 46, "of" should read --of the--;
Line 47, "to" should read --to the--;
Line 48, "how to" should be deleted;
Line 49, "make lower" should read --reduction of--;
Line 51, "times repetition" should read --repetitions--;

UNITED STATES PATENT AND TRADEMARK OFFICE
CERTIFICATE OF CORRECTION

PATENT NO. : 7,186,459 B2
APPLICATION NO. : 10/190490
DATED : March 6, 2007
INVENTOR(S) : Tsuyoshi Nomoto et al.

It is certified that error appears in the above-identified patent and that said Letters Patent is hereby corrected as shown below:

(COLUMN 5 Continued:)

Line 53, "preparing" should read --preparing a--;
Line 54, "to" should read --to a--;
Line 61, "(PA) and" should read --(PA) and a--;
Line 62, "preparing" should read --preparing a--; and
Line 66, "milk white" should read --milk-white--.

COLUMN 6:

Line 2, "of" should read --in that--;
Line 3, "being" should read --is--;
Line 5, "preparing" should read --preparing a--;
Line 7, "of phospholipic" should read --of a phospholipid--;
Line 24, "as" should read --as a--;
Line 25, "substance" should read --substance,--;
Line 28, "in" should read --in the--;
Line 34, "Liposome" should read --A liposome--;
Line 36, "methods" should read --methods,--;
Line 42, "kit" should read --kit,--;
Line 44, "as" should read --as a--;
Line 46, "fertilizer" should read --fertilizer,--;
Line 50, "fertilizer" should read --fertilizer,--;
Line 51, "or" should read --or a--;
Line 52, "fertilizer" should read --fertilizer,--;
Line 54, "fertilizer" should read --fertilizer,--;
Line 56, "fertilizer" should read --fertilizer,--;
Line 58, "of" should read --of a--;
Line 61, "methods" should read --methods,--; and
Line 67, "kit" should read --kit,--.

COLUMN 7:

Line 2, "as" should read --as a--;
Line 4, "enzyme" should read --enzyme,--;
Line 6, "vitamin" should read --vitamin,--;
Line 7, "pigment" should read --pigment,--;
Line 8, "component" should read --component,--;
Line 13, "hear" should read --hair--;
Line 14, "a" should read --an--;
Line 16, "Liposome" should read --A liposome--;

UNITED STATES PATENT AND TRADEMARK OFFICE
CERTIFICATE OF CORRECTION

PATENT NO. : 7,186,459 B2
APPLICATION NO. : 10/190490
DATED : March 6, 2007
INVENTOR(S) : Tsuyoshi Nomoto et al.

It is certified that error appears in the above-identified patent and that said Letters Patent is hereby corrected as shown below:

(COLUMN 7 Continued:)

Line 18, "methods" should read --methods,--;
Line 24, "kit" should read --kit,--;
Line 26, "as liposome for" should read --as a liposome for an--;
Line 30, "Liposome" should read --A liposome--;
Line 31, "methods" should read --methods,--;
Line 37, "kit" should read --kit,--; and
Line 39, "as" should read --as a--.

COLUMN 8:

Line 3, "Carmin" (both occurrences) should read --Carmine--;
Line 21, "methods" should read --methods,--;
Line 26, "kit" should read --kit,--;
Line 34, "(e.g." should read --(e.g.,--;
Line 37, "hormone" should read --hormones--;
Line 48, "drugs" should read --drugs,--;
Line 50, "Lipo-" should read --A lipo- --;
Line 52, "methods" should read --methods,--;
Line 58, "kit" should read --kit,--;
Line 59, "Liposome" should read --A liposome-- and "is" should read --has--;
Line 60, "in" should be deleted and "by coating" should read --if--;
Line 61, "wall with polyhydroxyalkanoate, and" should read --wall is coated with a polyhydroxyalkanoate.--;
Line 62, "given biocompatibility and biodegradability." should read --It is also biocompatible and biodegradable.-- and "When" should read --When a--;
Line 65, "releasability." should read --release of compounds.--.

COLUMN 9:

Line 10, "(e.g." should read --(e.g.,--; and
Line 15, "which" should read --which a--.

COLUMN 10:

Line 22, "above described" should read --above-described--;
Line 47, "3-hydrozybutyryl" should read --3-hydroxybutyryl--; and
Line 58, "under" should read --under a--.

UNITED STATES PATENT AND TRADEMARK OFFICE
CERTIFICATE OF CORRECTION

PATENT NO. : 7,186,459 B2
APPLICATION NO. : 10/190490
DATED : March 6, 2007
INVENTOR(S) : Tsuyoshi Nomoto et al.

It is certified that error appears in the above-identified patent and that said Letters Patent is hereby corrected as shown below:

COLUMN 11:

Line 30, "7.)" should read --7).--;
Line 48, "-$C_3F_7$.)" should read -- -$C_3F_7$).--; and
Line 67, "-$C_3F_7$.)" should read -- -$C_3F_7$).--.

COLUMN 12:

Line 19, "-$C_3F_7$.)" should read -- -$C_3F_7$).--;
Line 52, "7.)" should read --7).--; and
Line 67, "8.)" should read --8).--.

COLUMN 13:

Line 22, "—$OC_2H_5$.)" should read -- —$OC_2H_5$).--;
Line 46, " —$OC_2H_5$.)" should read -- —$OC_2H_5$).--;
Line 60, "9.)" should read --9).--; and
Line 61, "above described" should read --above-described--.

COLUMN 14:

Line 12, "above described Formula [1].)" should read --above-described Formula [1]).--;
Line 24, "the same as b and" should be deleted;
Line 25, "R2" should be deleted and "above described" should read --above-described--;
Line 26, "[2].)" should read --[2]).--;
Line 38, "the same as c and" should be deleted;
Line 39, "R3" should be deleted and "above described" should read --above-described--;
Line 40, "[3].)" should read --[3]).--;
Line 51, "the same as d and" should be deleted;
Line 52, "R4" should be deleted and "above described" should read --above-described--;
Line 53, "[4].)" should read --[4]).--;
Line 65, "the same as e and" should be deleted;
Line 66, "R4" should be deleted and "above described" should read --above-described--; and
Line 67, "[5].)" should read --[5]).--.

UNITED STATES PATENT AND TRADEMARK OFFICE
CERTIFICATE OF CORRECTION

PATENT NO. : 7,186,459 B2
APPLICATION NO. : 10/190490
DATED : March 6, 2007
INVENTOR(S) : Tsuyoshi Nomoto et al.

It is certified that error appears in the above-identified patent and that said Letters Patent is hereby corrected as shown below:

COLUMN 15:

Line 11, "the same as f" should be deleted;
    Line 12, "above described Chemical Formula [6].)" should read --above-described Chemical Formula [6]).--;
    Line 23, "the same as g" should be deleted;
    Line 24, "above described Chemical Formula [7].)" should read --above-described Chemical Formula [7]).--;
    Line 35, "the same as h and" should be deleted;
    Line 36, "R6" should be deleted and "above described" should read --above-described--;
    Line 37, "[8].)" should read --[8]).--;
    Line 48, "the same as i and R7" should be deleted;
    Line 49, "above described" should read --above-described--;
    Line 50, "[9].)" should read --[9]).--;
    Line 60, "the same as j" should be deleted; and
    Line 61, "above described Chemical Formula [10].)" should read --above-described Chemical Formula [10]).--.

COLUMN 16:

Line 1, "group," should read --group.--;
    Line 2, "but an" should read --An-- and "used, and the" should read --used. The--;
    Line 17, "10.)" should read --10).--;
    Line 43, "the following numbers, and corresponds" should read --any integer from 1 to 10, and corresponding--;
    Line 44, "above described" should read --above-described--;
    Line 45, "K represents any one of integer numbers of 1 to 10.)" should be deleted;
    Line 57, "above described" should read --above-described--;
    Line 59, "above described" should read --above-described--; and
    Line 65, "molecule" should read --molecule,--.

COLUMN 17:

Line 9, "above" should read --above- --;
    Line 17, "as appropriate the" should read --an appropriate--;
    Line 18, "as a sub-" should read --is added as a substrate.--;
    Line 19, "strate is added." should be deleted;
    Line 36, "its bonding to the liposome" should read --enhanced bonding to the liposome.--;

UNITED STATES PATENT AND TRADEMARK OFFICE
CERTIFICATE OF CORRECTION

PATENT NO. : 7,186,459 B2
APPLICATION NO. : 10/190490
DATED : March 6, 2007
INVENTOR(S) : Tsuyoshi Nomoto et al.

It is certified that error appears in the above-identified patent and that said Letters Patent is hereby corrected as shown below:

(COLUMN 17 Continued:)

Line 37, "enhanced." should be deleted;
Line 39, "various" should read --various improved--;
Line 40, "erties of which are improved." should read --erties.--;
Line 41, "give" should read --provide a--;
Line 42, "structure" should read --structure,-- and "liposome" should read --liposome,--;
Line 43, "PHA being" should read --PHA, with--;
Line 44, "given" should be deleted;
Line 46, "structure" should read --structure,--;
Line 48, "PHA given" should read --PHA, with--;
Line 51, "the meaning" should be deleted;
Line 56, "the meaning" should be deleted;
Line 61, "substance" should read --substance,--; and
Line 66, "by a" should read --by an-- and "3-hydroxyacyl" should read --¶ 3-hydroxyacyl--.

COLUMN 18:

Line 2, "organisms" should read --organisms,--;
Line 25, "host" should read --host,--;
Line 29, "TL2" should read --TL2 which--;
Line 30, "inventors" should read --inventors,--;
Line 41, "sp. microorganisms" should read --s.p. microorganisms,--;
Line 43, "etc." should read --etc.,--;
Line 45, "oleoborans," should read --oleovorans,--;
Line 47, "microorganisms" should read --microorganisms,--; and
Line 57, "BP-7376," should read --FERM BP-7376,--.

COLUMN 19:

Line 7, "as liquid culture and" should read --as a liquid culture and a--;
Line 8, "used" should read --used,--;
Line 9, "culture" should read --culture,--;
Line 10, "batch culture, fed batch culture," should read --a batch culture, a fed batch culture, a--;
Line 11, "and continuous culture" should read --and a continuous culture,--;
Line 22, "acid such" should read --acid, such--;
Line 30, "as to be" should read --that it is--;
Line 32, "that" should read --that an--;

UNITED STATES PATENT AND TRADEMARK OFFICE
CERTIFICATE OF CORRECTION

PATENT NO. : 7,186,459 B2
APPLICATION NO. : 10/190490
DATED : March 6, 2007
INVENTOR(S) : Tsuyoshi Nomoto et al.

It is certified that error appears in the above-identified patent and that said Letters Patent is hereby corrected as shown below:

(COLUMN 19 Continued:)

Line 36, "above described" should read --above-described--;
Line 38, "of" should read --of the--;
Line 41, "actively produced continuously" should read --actively and continuously produced--;
Line 44, "grown" should read --grown,--;
Line 45, "(e.g." (both occurrences) should read --(e.g.,--;
Line 46, "etc.)" should read --etc.),--; and
Line 47, "a" should read --an--.

COLUMN 20:

Line 2, "COCl$_2$:0.1g" should read --CoCl$_2$:0.1g--;
Line 8, "NiCl$_{2:0.1}$g" should read --NiCl$_2$:0.1g--;
Line 11, "satisfactorily be grown" should read --exhibit satisfactory growth,--;
Line 20, "microorganism" should read --microorganism,--;
Line 21, "in" should read --in the--;
Line 22, "a LB" should read --an LB--;
Line 23, "from" should be deleted;
Line 24, "addition," should read --addition, an--;
Line 27, "Antibiotics" should read --Antibiotics,--;
Line 28, "streptomycin" should read --streptomycin,--;
Line 37, "cells of" should read --cells of the-- and "enzymes" should read --enzymes,--;
Line 40, "like" should read --like,--;
Line 41, "Stabilizers" should read --Stabilizers,--;
Line 48, "microorganism" should read --a microorganism--;
Line 49, "lysozyme," should read --a lysozyme,--;
Line 52, "means" should read --a means--;
Line 57, "of" should read --of a--;
Line 58, ""tags"" should read --"tags",--;
Line 59, "making the protein to be bound" should read --binding the protein--;
Line 61, "by" should read --by a--;
Line 62, "protease" should read --protease,--; and
Line 67, "as a" should read --as an-- and "condition" should be deleted.

COLUMN 21:

Line 8, "A various" should read --Various--;
Line 9, "enzyme, and for" should read --enzyme. For--;

UNITED STATES PATENT AND TRADEMARK OFFICE
CERTIFICATE OF CORRECTION

PATENT NO. : 7,186,459 B2
APPLICATION NO. : 10/190490
DATED : March 6, 2007
INVENTOR(S) : Tsuyoshi Nomoto et al.

It is certified that error appears in the above-identified patent and that said Letters Patent is hereby corrected as shown below:

(COLUMN 21 Continued:)

Line 17, "in the" should read --at the --;
Line 20, "in the" should read --at the --;
Line 22, "in the" should read --at the --;
Line 27, "mixed together, and is" should read --the components are mixed and--;
Line 29, "together, and is" should read --and--;
Line 32, "solution of which reaction has been stopped" should read --solution, in which a reaction has been stopped--;
Line 37, "amount of" should read --amount of the--;
Line 40, "of" should read --of the--;
Line 41, "production of" should read --producing a--;
Line 42, "least" should read --least the--;
Line 48, "occasion demands," should read --as needed,--;
Line 51, "the numeral 2" should read --numeral 1--;
Line 53, "liposome;" should read --liposome; 3, a lipid soluble material;--;
Line 60, "size" should read --size,--,
Line 63, "liposome, while such a" should read --liposome depending on intended--;
Line 64, "condition depends on the" should be deleted; and
Line 65, "fallen in" should read --within--.

COLUMN 22:

Line 2, "methods" should read --methods,--;
Line 4, "method method" should read --method--;
Line 5, "sizes" should read --sizes,--;
Line 10, "interfere" should read --interfere with--;
Line 11, "reaction, but" should read --reaction. However,--;
Line 12, "into a composition allow-" should read --to allow--;
Line 13, "ing" should be deleted;
Line 22, "buffers" should read --buffers,--;
Line 25, "of" should be deleted;
Line 26, "of" should be deleted;
Line 28, "8.5, but the" should read --8.5. However, the pH may be set outside the above-describe ranges,--;
Line 29, "possibility is not excluded that a pH condition is set in a" should be deleted;
Line 30, "range other than the above described range" should be deleted;
Line 35, "added" should read --added,--, "has" should read --is of--, and "and concentration" should read --and has a concentration,--;

UNITED STATES PATENT AND TRADEMARK OFFICE
CERTIFICATE OF CORRECTION

PATENT NO. : 7,186,459 B2
APPLICATION NO. : 10/190490
DATED : March 6, 2007
INVENTOR(S) : Tsuyoshi Nomoto et al.

It is certified that error appears in the above-identified patent and that said Letters Patent is hereby corrected as shown below:

(COLUMN 22 Continued:)

Line 36, "not interfering" should read --which do not interfere with--, and "has a type and" should read --is of a type and has a--;
    Line 37, "concentration not interfering" should read --concentration, which do not interfere with--;
    Line 39, "surfactants" should read --surfactants,--;
    Line 43, "surfactants" should read --surfactants,--;
    Line 44, "surfactants" should read --surfactants,--;
    Line 49, "surfactants" should read --surfactants,--;
    Line 58, "has a type and concentration" should read --is of a type and has a concentration, which do--;
    Line 59, "interfering" should read --interfere with-- and "has a type and" should read --is of a type and has a--;
    Line 60, "tration not interfering" should read --tration, which do not interfere with--;
    Line 63, "hydrocarbons" should read --hydrocarbons,--;
    Line 64, "derivatives such as monovalent alcohols" should read --derivatives, such as monovalent alcohols,--;
    Line 65, "alcohols" should read --alcohols,--; and
    Line 66, "carboxylates" should read --carboxylates,--.

COLUMN 23:

Line 6, "used" should read --used,--;
    Line 7, "retained, and are" should read --retained and it is--;
    Line 8, "in" should read --to the--;
    Line 15, "protein" should read --protein,-- and "enzyme" should read --enzyme,--;
    Line 17, "bound, and shows properties as" should read --bound and which shows properties of--;
    Line 18, "groups" should read --groups,--;
    Line 19, "have" should read --which has--,
    Line 21, "groups" should read --groups,--;
    Line 25, "ionicity or hydrophobicity, or having both" should read --ionic and/or hydrophobic characteristics.--;
    Line 26, "ionicity and hydrophobicity." should be deleted;
    Line 28, "utilize" should read --utilize a--;
    Line 29, "thereof, for" should read --thereof. For--;
    Line 30, "lipid" should read --lipid,--;
    Line 33, "lipid" should read --lipid,--;
    Line 34, "preparing" should read --preparing the--;

UNITED STATES PATENT AND TRADEMARK OFFICE
CERTIFICATE OF CORRECTION

PATENT NO. : 7,186,459 B2
APPLICATION NO. : 10/190490
DATED : March 6, 2007
INVENTOR(S) : Tsuyoshi Nomoto et al.

It is certified that error appears in the above-identified patent and that said Letters Patent is hereby corrected as shown below:

(COLUMN 23 Continued:)

Line 38, "medium" should read --medium,--;
Line 41, "strength" should read --strength,--;
Line 43, "above described" should read --above-described--; and
Line 46, "in consideration of" should read --considering--.

COLUMN 24:

Line 1, "any treatment as" should read --any necessary treatment, taking--;
Line 2, "necessary that takes" should be deleted;
Line 7, "thiol group" should read --thiol group,--;
Line 11, "group" should read --group,-- and "amine" should read --amine,--;
Line 14, "reagent" should read --reagent,--;
Line 19, "reactivity" should read --reactivity,--;
Line 22, "ligand" should read --ligand,--;
Line 25, "biopolymer" should read --biopolymer,--;
Line 42, "(e.g." should read --(e.g.,--;
Line 64, "above described" should read --above-described--;
Line 66, "methodology for" should read --methodology.--; and
Line 67, "use." should be deleted.

COLUMN 25:

Line 11, "above described" should read --above-described--;
Line 14, "of" should read --of a--;
Line 15, "of" should be deleted;
Line 16, "1g of" should read --1g of a--;
Line 25, "preferable" should read --preferable,--;
Line 26, "reduction of" should read --reduction in--;
Line 39, "preserved" should read --preserved, separately prepared--;
Line 40, "separately prepared" should be deleted;
Line 41, "step" should read --step,--;
Line 43, "concentrations of" should read --concentrations, which are--;
Line 46, "above describe step, the composition" should read --above-described step, the composition,--;
Line 47, "type" should read --the type--;
Line 48, "solution" should read --solution,--;
Line 59, "of" should read --of a--; and
Line 62, "by" should read --in--.

UNITED STATES PATENT AND TRADEMARK OFFICE
CERTIFICATE OF CORRECTION

PATENT NO. : 7,186,459 B2
APPLICATION NO. : 10/190490
DATED : March 6, 2007
INVENTOR(S) : Tsuyoshi Nomoto et al.

It is certified that error appears in the above-identified patent and that said Letters Patent is hereby corrected as shown below:

COLUMN 26:

Line 3, "of different composition again," should read --of a different composition,--;
Line 5, "carried out" should read --performed-- and "of reaction solution" should read --of a reaction solution,--;
Line 6, "so that a composition allowing" should read --which allows the--;
Line 7, "can" should read --to--;
Line 8, "till" should read --until--;
Line 10, "that" should read --for--;
Line 11, "can" should read --to--;
Line 16, "of" should be deleted;
Line 17, "of" should be deleted and "For" should read --For the--;
Line 18, "of" should be deleted;
Line 21, "above described range" should read --above-described range,--;
Line 25, "The reaction temperature is set as appropriate" should read --The appropriate reaction temperature is set,--;
Line 29, "above" should read --above- --;
Line 30, "range" should read --range,--;
Line 34, "range of" should read --range, which is--;
Line 35, "hours" should read --hours,--;
Line 46, "of" should be deleted;
Line 48, "amount of" should read --amount of the--;
Line 52, "of" (both occurrences) should read --of the--;
Line 53, "liposome" should read --liposome,-- and "of" should be deleted;
Line 56, "mass" should read --mass,--;
Line 59, "liposome" should read --liposome,--, and
Line 62, "methods" should read --methods,--.

COLUMN 27:

Line 3, "processing" should read --processing,-- and "modification" should read --modification,--;
Line 22, "limited" should read --limited,--;
Line 23, "achieved, but," should read --achieved. However,--;
Line 27, "used as a suitable" should read --suitably used.--;
Line 28, "method." should be deleted;
Line 30, "above described" should read --above-described--;
Line 31, "limited" should read --limited,--;
Line 38, "and" should read --and an--;
Line 41, "having high reactivity" should read --that is highly reactive--;

UNITED STATES PATENT AND TRADEMARK OFFICE
CERTIFICATE OF CORRECTION

PATENT NO. : 7,186,459 B2
APPLICATION NO. : 10/190490
DATED : March 6, 2007
INVENTOR(S) : Tsuyoshi Nomoto et al.

It is certified that error appears in the above-identified patent and that said Letters Patent is hereby corrected as shown below:

(COLUMN 27 Continued:)

Line 47, "amino modified polymers" should read --amino-modified polymers,-- and "as" should read --as an-- and "amino modified" should read --amino-modified--;
Line 49, "for amino modified" should read --for the amino-modified--;
Line 50, "or amino modified" should read --or the amino-modified--;
Line 59, "compound" should read --compound,--; and
Line 66, "below" should read --below may be used--.

COLUMN 28:

Line 6, "  " should read -- 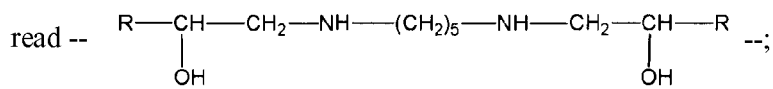 --;

Line 19, "retrieving" should read --retrieving a--;
Line 24, "of" should read --of the--;
Line 30, "form" should read --form,--;
Line 32, "in particular, the form of" should read --particularly,--;
Line 34, "stabilizer" should read --stabilizer,-- and "puffing" should read --puffing (swelling)--;
Line 37, "polysaccharides" should read --polysaccharides,--;
Line 38, "zantan" should read --zanthan--;
Line 39, "polymers" should read --polymers,--;
Line 40, "powders" should read --powders,--;
Line 44, "alcohols" should read --alcohols,--;
Line 45, "salts" should read --salts,--;
Line 52, "form" should read --form,--;
Line 53, "in particular," should read --particularly,--;
Line 54, "the form of" should be deleted;
Line 56, "stabilizer" should read --stabilizer,-- and "puffing" should read --puffing (swelling)--;
Line 59, "polysaccharides" should read --polysaccharides,-- and "zantan" should read --zanthan--;

UNITED STATES PATENT AND TRADEMARK OFFICE
CERTIFICATE OF CORRECTION

PATENT NO. : 7,186,459 B2
APPLICATION NO. : 10/190490
DATED : March 6, 2007
INVENTOR(S) : Tsuyoshi Nomoto et al.

It is certified that error appears in the above-identified patent and that said Letters Patent is hereby corrected as shown below:

(COLUMN 28 Continued:)

Line 61, "polymers" should read --polymers,--;
    Line 62, "powders" should read --powders,--;
    Line 65, "alcohols" should read --alcohols,--; and
    Line 66, "salts" should read --salts,--.

COLUMN 29:

Line 1, "When" should read --When a--;
    Line 2, "as liposome for a fertilizer" should read --as a liposome for a cosmetic--;
    Line 3, "mekium" should read --medium-- and "well known" should read --well-known--;
    Line 5, "hydrocarbons" should read --hydrocarbons,--;
    Line 7, "waxes" should read --waxes,--;
    Line 8, "thereof" should read --thereof,--;
    Line 11, "silicones" should read --silicones,--;
    Line 14, "alcohols" should read --alcohols,--;
    Line 16, "moisture-keeping action" should read --moisture-retaining characteristics,--;
    Line 18, "When" should read --When a--;
    Line 19, "as" should read --as a--;
    Line 22, "means" should read --means,--;
    Line 24, "When" should read --When a--;
    Line 26, "supporting" should read --supporting a--;
    Line 32, "in" should read --to--;
    Line 33, "proteins" should read --proteins,--;
    Line 35, "polymers" should read --polymers,--;
    Line 38, "pyrolidone," should read --pyrrolidone,--;
    Line 43, "particularly" should read --particularly,--;
    Line 45, "in" should read --to--;
    Line 47, "Examples" should read --Examples of--;
    Line 48, "esters" should read --esters,--;
    Line 49, "sulfates" should read --sulfates,--;
    Line 51, "benzensul-" should read --benzenesul- --;
    Line 52, "fonates" should read --fonates,-- and "benzanesulfonate," should read --benzenesulfonate,--;
    Line 55, "napththalenesulfonates" should read --naphthalenesulfonates,--;
    Line 57, "sulfosuccinates" should read --sulfosuccinates,--;
    Line 59, "sulfates" should read --sulfates,--;

UNITED STATES PATENT AND TRADEMARK OFFICE
CERTIFICATE OF CORRECTION

PATENT NO. : 7,186,459 B2
APPLICATION NO. : 10/190490
DATED : March 6, 2007
INVENTOR(S) : Tsuyoshi Nomoto et al.

It is certified that error appears in the above-identified patent and that said Letters Patent is hereby corrected as shown below:

(COLUMN 29 Continued:)

Line 63, "phosphates" should read --phosphates,--;
Line 65, "salts" should read --salts,--; and
Line 67, "salts" should read --salts,--.

COLUMN 30:

Line 4, "betains" should read --betains,--;
Line 5, "oxides" should read --oxides,--;
Line 7, "ethers" should read --ethers,--;
Line 10, "ethers" should read --ethers,--;
Line 12, "ploymers" should read --polymers,--,
Line 14, "esters" should read --esters,--;
Line 22, "esters" should read --esters,--;
Line 23, "esters" should read --esters,--;
Line 25, "larger" should read --greater--;
Line 28, "5%" should read --5%,-- and "of" should read --of the--; and
Line 55, "was" should read --was used--.

COLUMN 31:

Line 18, "PBBR" should read --pBBR--;
Line 23, "Electroporation" should read --electroporation--;
Line 49, "NO: 2," should read --NO: 2, an--;
Line 52, "and" should read --and an--;
Line 54, "primer" should read --primer,--;
Line 59, "Ltd.)" should read --Ltd.).-- and "In" should read --¶ In--;
Line 60, "of" should read --of a--; and
Line 64, "4," should read --4, an--.

COLUMN 32:

Line 1, "primer" should read --primer,--;
Line 5, "Ltd.)" should read --Ltd.).--;
Line 6, "fragment" should read --fragment,--;
Line 7, "enzyme were each" should read --enzyme, was--;
Line 14, "gene" should read --gene,--;
Line 15, "removed" should read --removed,--;
Line 31, "*coil*" should read --*coli*--;

UNITED STATES PATENT AND TRADEMARK OFFICE
CERTIFICATE OF CORRECTION

PATENT NO. : 7,186,459 B2
APPLICATION NO. : 10/190490
DATED : March 6, 2007
INVENTOR(S) : Tsuyoshi Nomoto et al.

It is certified that error appears in the above-identified patent and that said Letters Patent is hereby corrected as shown below:

(COLUMN 32 Continued:)

Line 48, "in the" (both occurrences) should be deleted and "XhoI" should read --XhoI--;
Line 51, "and" should read --and an--;
Line 57, "in the" (both occurrences) should be deleted; and
Line 59, "of" should read --of the--.

COLUMN 33:

Line 9, "resuspended" should read --re-suspended--;
Line 19, "treated" should read --treated in advance-- and "adsorption in advance." should read --adsorption.--;
Line 25, "PBS, and was resus-" should read --PBS and re-sus- --;
Line 32, "was" should be deleted;
Line 34, "added, and was" should read --added and--; and
Line 35, "adsorbed" should read --adsorbed,--.

COLUMN 34:

Line 7, "to" should read --to a--;
Line 9, "resuspended" should read --re-suspended--;
Line 44, "and was" should read --and--; and
Line 64, "1-litter" should read --1-liter--.

COLUMN 35:

Line 5, "30 sec" should read --30 sec,--;
Line 18, "30 mL" should read --30 mL,--;
Line 32, "product" should read --product,--;
Line 35, "size fractioned" should read --size-fractioned--;
Line 41, "vacuum" should read --vacuum- --;
Line 42, "dried" should read --dried,--;
Line 46, "concentration" should read --concentrating--;
Line 47, "by" should read --using--;
Line 16, "product" should read --product,--;
Line 19, "size fractioned" should read --size-fractioned--;
Line 20, "yield" should read --yield a--;
Line 22, "by" should read --by a--;
Line 25, "vacuum" should read --vacuum- --;

UNITED STATES PATENT AND TRADEMARK OFFICE
CERTIFICATE OF CORRECTION

PATENT NO. : 7,186,459 B2
APPLICATION NO. : 10/190490
DATED : March 6, 2007
INVENTOR(S) : Tsuyoshi Nomoto et al.

It is certified that error appears in the above-identified patent and that said Letters Patent is hereby corrected as shown below:

(COLUMN 35 Continued:)

Line 26, "dried" should read --dried,--; and
Line 27, "chloroform and the" should read --chloroform. Then,--.

COLUMN 37:

Line 4, "product" should read --product,--;
Line 7, "size fractioned" should read --size-fractioned--;
Line 8, "yield" should read --yield a--;
Line 10, "and was found" should be deleted;
Line 14, "vacuum" should read --vacuum- --;
Line 16, "chloroform" should read --chloroform,--;
Line 40, "1-litter" should read --1-liter--;
Line 41, "ether 1" should read --ether (1--;
Line 56, "so as" should be deleted; and
Line 62, "30 mL" should read --30 mL,--.

COLUMN 38:

Line 2, "by" should read --by a--;
Line 9, "product" should read --product,--;
Line 12, "size fractioned" should read --size-fractioned--;
Line 15, "dynamic" should read --a dynamic-- and "and was found" should be deleted;
Line 18, "vacuum" should read --vacuum- --;
Line 19, "dried and" should read --dried,--;
Line 20, "form" should read --form,--;
Line 33, "(5 aim)," should read --(5 μm),--;
Line 59, "TAFLOW" should read --TAF10W--;
Line 64, "of a 80% of" should read --at an 80%--;
Line 65, "of a" should read --at an--; and
Line 66, "of" should be deleted.

COLUMN 39:

Line 1, "in" should read --at--;
Line 11, "minutes to" should read --minutes, so that nitrogen gas could sufficiently penetrate--;
Line 12, "sufficiently penetrate nitrogen gas" should be deleted;
Line 19, "obtaining" should read --obtaining a--;

UNITED STATES PATENT AND TRADEMARK OFFICE
CERTIFICATE OF CORRECTION

PATENT NO. : 7,186,459 B2
APPLICATION NO. : 10/190490
DATED : March 6, 2007
INVENTOR(S) : Tsuyoshi Nomoto et al.

It is certified that error appears in the above-identified patent and that said Letters Patent is hereby corrected as shown below:

(COLUMN 39 Continued:)

Line 25, "product" should read --product,--;
    Line 28, "size fractioned" should read --size-fractioned--;
    Line 29, "yield" should read --yield a--;
    Line 34, "vacuum" should read --vacuum- --;
    Line 35, "dried and" should read --dried,--;
    Line 36, "form" should read --form,--;
    Line 55, "Releasability" should read --Release--;
    Line 57, "1-litter" should read --1-liter--; and
    Line 61, "Calcein" should read --Calcein,--.

COLUMN 40:

Line 10, "obtain" should read --obtain a--;
    Line 17, "product" should read --product,--;
    Line 20, "size fractioned" should read --size-fractioned--;
    Line 33, "was" should read --exhibited an--;
    Line 34, "in" should be deleted;
    Line 40, "again" should be deleted;
    Line 43, "is improved in" should read --has an improved--;
    Line 45, "of" should read --in--;
    Line 49, "liposome because of" should read --liposome, which is due to--;
    Line 50, "of" should read --for--;
    Line 52, "because" should be deleted;
    Line 53, "liposome is kept to be" should read --liposome, which is--;
    Line 55, "drives" should read --accelerates--;
    Line 56, "contents to be accelerated, thus" should read --contents,--;
    Line 63, "1-litter" should read --1-liter--;
    Line 64, "1 to 1 ratio," should read --(1 to 1 ratio),--; and
    Line 67, "Calcein" should read --Calcein,--.

COLUMN 41:

Line 3, "prepare" should read --prepare a--;
    Line 15, "filter of 1.2 μm" should read --1.2 μm filter--;
    Line 16, "obtain" should read --obtain a--;
    Line 20, "to" should read --to a--;
    Line 24, "size fractioned" should read --size-fractioned--;
    Line 40, "30-munite shaking," should read --shaking for 30 minutes,--; and
    Line 43, "obtaining" should read --obtaining a--.

UNITED STATES PATENT AND TRADEMARK OFFICE
CERTIFICATE OF CORRECTION

PATENT NO. : 7,186,459 B2
APPLICATION NO. : 10/190490
DATED : March 6, 2007
INVENTOR(S) : Tsuyoshi Nomoto et al.

It is certified that error appears in the above-identified patent and that said Letters Patent is hereby corrected as shown below:

COLUMN 42:

Line 23, "bromoacetate" should read --bromoacetate,--;
Line 27, "CoA" should read --CoA,--;
Line 29, "acid" should read --acid,--;
Line 40, "slide glass" should read --glass slide--;
Line 43, "slide glass," should read --glass slide,--;
Line 51, "of" should read --of the--; and
Line 57, "liposome at all." should read --liposome.--.

COLUMN 44:
Line 14, "is made to react" should read --reacts--;
Line 18, "other" should read --other,--;
Line 19, "results" should read --results,--;
Line 21, "embodiments, and it will now be that" should read --embodiments.--;
Line 22, "changed" should read --However, changes--; and
Line 25, "modifications as" should read --modifications, which--.

Signed and Sealed this

Fifth Day of August, 2008

JON W. DUDAS
*Director of the United States Patent and Trademark Office*

SEQUENCE LISTING

```
<160> NUMBER OF SEQ ID NOS: 14

<210> SEQ ID NO 1
<211> LENGTH: 559
<212> TYPE: PRT
<213> ORGANISM: Pseudomonas cichorii YN2 ; FERM BP-7375

<400> SEQUENCE: 1

Met Ser Asn Lys Ser Asn Asp Glu Leu Lys Tyr Gln Ala Ser Glu Asn
 1               5                  10                  15

Thr Leu Gly Leu Asn Pro Val Val Gly Leu Arg Gly Lys Asp Leu Leu
            20                  25                  30

Ala Ser Ala Arg Met Val Leu Arg Gln Ala Ile Lys Gln Pro Val His
        35                  40                  45

Ser Val Lys His Val Ala His Phe Gly Leu Glu Leu Lys Asn Val Leu
    50                  55                  60

Leu Gly Lys Ser Gly Leu Gln Pro Thr Ser Asp Asp Arg Arg Phe Ala
65                  70                  75                  80

Asp Pro Ala Trp Ser Gln Asn Pro Leu Tyr Lys Arg Tyr Leu Gln Thr
                85                  90                  95

Tyr Leu Ala Trp Arg Lys Glu Leu His Asp Trp Ile Asp Glu Ser Asn
            100                 105                 110

Leu Ala Pro Lys Asp Val Ala Arg Gly His Phe Val Ile Asn Leu Met
        115                 120                 125

Thr Glu Ala Met Ala Pro Thr Asn Thr Ala Ala Asn Pro Ala Ala Val
    130                 135                 140

Lys Arg Phe Phe Glu Thr Gly Gly Lys Ser Leu Leu Asp Gly Leu Ser
145                 150                 155                 160

His Leu Ala Lys Asp Leu Val His Asn Gly Gly Met Pro Ser Gln Val
                165                 170                 175
```

-continued

```
Asn Met Gly Ala Phe Glu Val Gly Lys Ser Leu Gly Val Thr Glu Gly
            180                 185                 190
Ala Val Val Phe Arg Asn Asp Val Leu Glu Leu Ile Gln Tyr Lys Pro
        195                 200                 205
Thr Thr Glu Gln Val Tyr Glu Arg Pro Leu Leu Val Pro Pro Gln
    210                 215                 220
Ile Asn Lys Phe Tyr Val Phe Asp Leu Ser Pro Asp Lys Ser Leu Ala
225                 230                 235                 240
Arg Phe Cys Leu Arg Asn Asn Val Gln Thr Phe Ile Val Ser Trp Arg
                245                 250                 255
Asn Pro Thr Lys Glu Gln Arg Glu Trp Gly Leu Ser Thr Tyr Ile Glu
            260                 265                 270
Ala Leu Lys Glu Ala Val Asp Val Val Thr Ala Ile Thr Gly Ser Lys
        275                 280                 285
Asp Val Asn Met Leu Gly Ala Cys Ser Gly Gly Ile Thr Cys Thr Ala
    290                 295                 300
Leu Leu Gly His Tyr Ala Ala Ile Gly Glu Asn Lys Val Asn Ala Leu
305                 310                 315                 320
Thr Leu Leu Val Ser Val Leu Asp Thr Thr Leu Asp Ser Asp Val Ala
                325                 330                 335
Leu Phe Val Asn Glu Gln Thr Leu Glu Ala Ala Lys Arg His Ser Tyr
            340                 345                 350
Gln Ala Gly Val Leu Glu Gly Arg Asp Met Ala Lys Val Phe Ala Trp
        355                 360                 365
Met Arg Pro Asn Asp Leu Ile Trp Asn Tyr Trp Val Asn Asn Tyr Leu
    370                 375                 380
Leu Gly Asn Glu Pro Pro Val Phe Asp Ile Leu Phe Trp Asn Asn Asp
385                 390                 395                 400
Thr Thr Arg Leu Pro Ala Ala Phe His Gly Asp Leu Ile Glu Leu Phe
                405                 410                 415
Lys Asn Asn Pro Leu Ile Arg Pro Asn Ala Leu Glu Val Cys Gly Thr
            420                 425                 430
Pro Ile Asp Leu Lys Gln Val Thr Ala Asp Ile Phe Ser Leu Ala Gly
        435                 440                 445
Thr Asn Asp His Ile Thr Pro Trp Lys Ser Cys Tyr Lys Ser Ala Gln
    450                 455                 460
Leu Phe Gly Gly Asn Val Glu Phe Val Leu Ser Ser Ser Gly His Ile
465                 470                 475                 480
Gln Ser Ile Leu Asn Pro Gly Asn Pro Lys Ser Arg Tyr Met Thr
                485                 490                 495
Ser Thr Glu Val Ala Glu Asn Ala Asp Glu Trp Gln Ala Asn Ala Thr
            500                 505                 510
Lys His Thr Asp Ser Trp Trp Leu His Trp Gln Ala Trp Gln Ala Gln
        515                 520                 525
Arg Ser Gly Glu Leu Lys Lys Ser Pro Thr Lys Leu Gly Ser Lys Ala
    530                 535                 540
Tyr Pro Ala Gly Glu Ala Ala Pro Gly Thr Tyr Val His Glu Arg
545                 550                 555
```

<210> SEQ ID NO 2
<211> LENGTH: 1680
<212> TYPE: DNA
<213> ORGANISM: Pseudomonas cichorii YN2 ; FERM BP-7375

<400> SEQUENCE: 2

-continued

| | |
|---|---|
| atgagtaaca agagtaacga tgagttgaag tatcaagcct ctgaaaacac | 50 |
| cttgggcttt aatcctgtcg ttgggctgcg tggaaaggat ctactggctt | 100 |
| ctgctcgaat ggtgcttagg caggccatca agcaaccggt gcacagcgtc | 150 |
| aaacatgtcg cgcactttgg tcttgaactc aagaacgtac tgctgggtaa | 200 |
| atccggctg caaccgacca gcgatgaccg tcgcttcgcc gatccggcct | 250 |
| ggagccagaa cccgctctat aaacgttatt tgcaaaccta cctggcgtgg | 300 |
| cgcaaggaac tccacgactg gatcgatgaa agtaacctcg cccccaagga | 350 |
| tgtggcgcgt gggcacttcg tgatcaacct catgaccgaa gccatggcgc | 400 |
| cgaccaacac cgcggccaac ccggcggcag tcaaacgctt tttcgaaacc | 450 |
| ggtggcaaaa gcctgctcga cggcctctcg cacctggcca aggatctggt | 500 |
| acacaacggc ggcatgccga gccaggtcaa catgggtgca ttcgaggtcg | 550 |
| gcaagagcct gggcgtgacc gaaggcgcgg tggtgtttcg caacgatgtg | 600 |
| ctggaactga tccagtacaa gccgaccacc gagcaggtat acgaacgccc | 650 |
| gctgctggtg gtgccgccgc agatcaacaa gttctacgtt ttcgacctga | 700 |
| gcccggacaa gagcctggcg cggttctgcc tgcgcaacaa cgtgcaaacg | 750 |
| ttcatcgtca gctggcgaaa tcccaccaag gaacagcgag agtggggcct | 800 |
| gtcgacctac atcgaagccc tcaaggaagc ggttgatgtc gttaccgcga | 850 |
| tcaccggcag caaagacgtg aacatgctcg gcgcctgctc cggcggcatc | 900 |
| acttgcaccg cgctgctggg ccattacgcg gcgattggcg aaaacaaggt | 950 |
| caacgccctg accttgctgg tgagcgtgct tgataccacc ctcgacagcg | 1000 |
| atgttgccct gttcgtcaat gaacagaccc ttgaagccgc caagcgccac | 1050 |
| tcgtaccagg ccggcgtact ggaaggccgc gacatggcga aggtcttcgc | 1100 |
| ctggatgcgc cccaacgatc tgatctggaa ctactgggtc aacaattacc | 1150 |
| tgctaggcaa cgaaccgccg gtgttcgaca tcctgttctg gaacaacgac | 1200 |
| accacacggt tgcccgcggc gttccacggc gacctgatcg aactgttcaa | 1250 |
| aaataaccca ctgattcgcc cgaatgcact ggaagtgtgc ggcacccca | 1300 |
| tcgacctcaa gcaggtgacg gccgacatct ttccctggc cggcaccaac | 1350 |
| gaccacatca ccccgtggaa gtcctgctac aagtcggcgc aactgtttgg | 1400 |
| cggcaacgtt gaattcgtgc tgtcgagcag cgggcatatc cagagcatcc | 1450 |
| tgaacccgcc gggcaatccg aaatcgcgct acatgaccag caccgaagtg | 1500 |
| gcggaaaatg ccgatgaatg gcaagcgaat gccaccaagc ataccgattc | 1550 |
| ctggtggctg cactggcagg cctggcaggc ccaacgctcg ggcgagctga | 1600 |
| aaaagtcccc gacaaaactg ggcagcaagg cgtatccggc aggtgaagcg | 1650 |
| gcgccaggca cgtacgtgca cgaacggtaa | 1680 |

<210> SEQ ID NO 3
<211> LENGTH: 560
<212> TYPE: PRT
<213> ORGANISM: Pseudomonas cichorii YN2 ; FERM BP-7375

<400> SEQUENCE: 3

Met Arg Asp Lys Pro Ala Arg Glu Ser Leu Pro Thr Pro Ala Lys Phe
 1               5                  10                  15

```
Ile Asn Ala Gln Ser Ala Ile Thr Gly Leu Arg Gly Arg Asp Leu Val
             20                  25                  30

Ser Thr Leu Arg Ser Val Ala Ala His Gly Leu Arg His Pro Val His
         35                  40                  45

Thr Ala Arg His Ala Leu Lys Leu Gly Gly Gln Leu Gly Arg Val Leu
     50                  55                  60

Leu Gly Asp Thr Leu His Pro Thr Asn Pro Gln Asp Arg Arg Phe Asp
 65                  70                  75                  80

Asp Pro Ala Trp Ser Leu Asn Pro Phe Tyr Arg Arg Ser Leu Gln Ala
                 85                  90                  95

Tyr Leu Ser Trp Gln Lys Gln Val Lys Ser Trp Ile Asp Glu Ser Asn
            100                 105                 110

Met Ser Pro Asp Asp Arg Ala Arg Ala His Phe Ala Phe Ala Leu Leu
        115                 120                 125

Asn Asp Ala Val Ser Pro Ser Asn Ser Leu Leu Asn Pro Leu Ala Ile
    130                 135                 140

Lys Glu Ile Phe Asn Ser Gly Gly Asn Ser Leu Val Arg Gly Ile Gly
145                 150                 155                 160

His Leu Val Asp Asp Leu Leu His Asn Asp Gly Leu Pro Arg Gln Val
                165                 170                 175

Thr Arg His Ala Phe Glu Val Gly Lys Thr Val Ala Thr Thr Thr Gly
            180                 185                 190

Ala Val Val Phe Arg Asn Glu Leu Leu Glu Leu Ile Gln Tyr Lys Pro
        195                 200                 205

Met Ser Glu Lys Gln Tyr Ser Lys Pro Leu Leu Val Val Pro Pro Gln
    210                 215                 220

Ile Asn Lys Tyr Tyr Ile Phe Asp Leu Ser Pro His Asn Ser Phe Val
225                 230                 235                 240

Gln Phe Ala Leu Lys Asn Gly Leu Gln Thr Phe Val Ile Ser Trp Arg
                245                 250                 255

Asn Pro Asp Val Arg His Arg Glu Trp Gly Leu Ser Thr Tyr Val Glu
            260                 265                 270

Ala Val Glu Glu Ala Met Asn Val Cys Arg Ala Ile Thr Gly Ala Arg
        275                 280                 285

Glu Val Asn Leu Met Gly Ala Cys Ala Gly Gly Leu Thr Ile Ala Ala
    290                 295                 300

Leu Gln Gly His Leu Gln Ala Lys Arg Gln Leu Arg Arg Val Ser Ser
305                 310                 315                 320

Ala Thr Tyr Leu Val Ser Leu Leu Asp Ser Gln Leu Asp Ser Pro Ala
                325                 330                 335

Thr Leu Phe Ala Asp Glu Gln Thr Leu Glu Ala Ala Lys Arg Arg Ser
            340                 345                 350

Tyr Gln Lys Gly Val Leu Glu Gly Arg Asp Met Ala Lys Val Phe Ala
        355                 360                 365

Trp Met Arg Pro Asn Asp Leu Ile Trp Ser Tyr Phe Val Asn Asn Tyr
    370                 375                 380

Leu Met Gly Lys Glu Pro Pro Ala Phe Asp Ile Leu Tyr Trp Asn Asn
385                 390                 395                 400

Asp Asn Thr Arg Leu Pro Ala Ala Leu His Gly Asp Leu Leu Asp Phe
                405                 410                 415

Phe Lys His Asn Pro Leu Ser His Pro Gly Gly Leu Glu Val Cys Gly
            420                 425                 430
```

```
Thr Pro Ile Asp Leu Gln Lys Val Thr Val Asp Ser Phe Ser Val Ala
        435                 440                 445

Gly Ile Asn Asp His Ile Thr Pro Trp Asp Ala Val Tyr Arg Ser Thr
    450                 455                 460

Leu Leu Leu Gly Gly Glu Arg Arg Phe Val Leu Ala Asn Ser Gly His
465                 470                 475                 480

Val Gln Ser Ile Leu Asn Pro Pro Asn Asn Pro Lys Ala Asn Tyr Leu
                485                 490                 495

Glu Gly Ala Lys Leu Ser Ser Asp Pro Arg Ala Trp Tyr Tyr Asp Ala
                500                 505                 510

Lys Pro Val Asp Gly Ser Trp Trp Thr Gln Trp Leu Gly Trp Ile Gln
            515                 520                 525

Glu Arg Ser Gly Ala Gln Lys Glu Thr His Met Ala Leu Gly Asn Gln
            530                 535                 540

Asn Tyr Pro Pro Met Glu Ala Ala Pro Gly Thr Tyr Val Arg Val Arg
545                 550                 555                 560

<210> SEQ ID NO 4
<211> LENGTH: 1683
<212> TYPE: DNA
<213> ORGANISM: Pseudomonas cichorii YN2 ; FERM BP-7375

<400> SEQUENCE: 4
atgcgcgata aacctgcgag ggagtcacta cccacccccg ccaagttcat        50
caacgcacaa agtgcgatta ccggcctgcg tggccgggat ctggtttcga       100 cttttgcgcag tgtcgccgcc catggcctgc gccaccccgt gcacaccgcg       150
cgacacgcct tgaaactggg tggtcaactg ggacgcgtgt tgctgggcga       200
caccctgcat cccaccaacc gcaagaccg tcgcttcgac gatccggcgt        250
ggagtctcaa tcccttttat cgtcgcagcc tgcaggcgta cctgagctgg       300
cagaagcagg tcaagagctg gatcgacgaa agcaacatga gcccggatga       350
ccgcgcccgt gcgcacttcg cgttcgccct gctcaacgat gccgtgtcgc       400
cgtccaacag cctgctcaat ccgctggcga tcaaggaaat cttcaactcc       450
ggcggcaaca gcctggtgcg cgggatcggc catctggtcg atgacctctt       500
gcacaacgat ggcttgcccc ggcaagtcac caggcatgca ttcgaggttg       550
gcaagaccgt cgccaccacc accggcgccg tggtgtttcg caacgagctg       600
ctggagctga tccaatacaa gccgatgagc gaaaagcagt attccaaacc       650
gctgctggtg gtgccgccac agatcaacaa gtactacatt tttgacctca       700
gcccccataa cagcttcgtc cagttcgcgc tcaagaacgg cctgcaaacc       750
ttcgtcatca gctggcgcaa tccggatgta cgtcaccgcg aatggggcct       800
gtcgacctac gtcgaagcgg tggaagaagc catgaatgtc tgccgggcaa       850
tcaccggcgc gcgcgaggtc aacctgatgg gcgcctgcgc tggcgggctg       900
accattgctg ccctgcaggg ccacttgcaa gccaagcgac agctgcgccg       950
cgtctccagc gcgacgtacc tggtgagcct gctcgacagc caactggaca      1000
gcccggccac actcttcgcc gacgaacaga ccctggaggc ggccaagcgc      1050
cgctcctacc agaaaggtgt gctggaaggc gcgacatgg ccaaggtttt       1100 cgcctggatg cgccccaacg atttgatctg gagctacttc gtcaacaatt      1150
acctgatggg caaggagccg ccggcgttcg acattctcta ctggaacaat      1200
```

-continued

```
gacaacacac gcctgccggc cgccctgcat ggtgacttgc tggacttctt         1250
caagcacaac ccgctgagcc atccgggtgg cctggaagtg tgcggcaccc         1300
cgatcgactt gcaaaaggtc accgtcgaca gtttcagcgt ggccggcatc         1350
aacgatcaca tcacgccgtg ggacgcggtg tatcgctcaa ccctgttgct         1400
cggtggcgag cgtcgctttg tcctggccaa cagcggtcat gtgcagagca         1450
ttctcaaccc gccgaacaat ccgaaagcca actacctcga aggtgcaaaa         1500
ctaagcagcg accccagggc ctggtactac gacgccaagc ccgtcgacgg         1550
tagctggtgg acgcaatggc tgggctggat tcaggagcgc tcgggcgcgc         1600
aaaaagaaac ccacatggcc ctcggcaatc agaattatcc accgatggag         1650
gcggcgcccg ggacttacgt gcgcgtgcgc tga                          1683
```

<210> SEQ ID NO 5
<211> LENGTH: 20
<212> TYPE: DNA
<213> ORGANISM: Artificial Sequence
<220> FEATURE:
<223> OTHER INFORMATION: Primer for PCR multiplication

<400> SEQUENCE: 5

```
tgctggaact gatccagtac                                          20
```

<210> SEQ ID NO 6
<211> LENGTH: 23
<212> TYPE: DNA
<213> ORGANISM: Artificial Sequence
<220> FEATURE:
<223> OTHER INFORMATION: Primer for PCR multiplication

<400> SEQUENCE: 6

```
gggttgagga tgctctggat gtg                                      23
```

<210> SEQ ID NO 7
<211> LENGTH: 29
<212> TYPE: DNA
<213> ORGANISM: Artificial Sequence
<220> FEATURE:
<223> OTHER INFORMATION: Primer for PCR multiplication

<400> SEQUENCE: 7

```
ggaccaagct tctcgtctca gggcaatgg                                29
```

<210> SEQ ID NO 8
<211> LENGTH: 29
<212> TYPE: DNA
<213> ORGANISM: Artificial Sequence
<220> FEATURE:
<223> OTHER INFORMATION: Primer for PCR multiplication

<400> SEQUENCE: 8

```
cgagcaagct tgctcctaca ggtgaaggc                                29
```

<210> SEQ ID NO 9
<211> LENGTH: 29
<212> TYPE: DNA
<213> ORGANISM: Artificial Sequence
<220> FEATURE:
<223> OTHER INFORMATION: Primer for PCR multiplication

<400> SEQUENCE: 9

```
gtattaagct tgaagacgaa ggagtgttg                                    29

<210> SEQ ID NO 10
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 10
catccaagct tcttatgatc gggtcatgcc                                   30

<210> SEQ ID NO 11
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 11
cgggatccag taacaagagt aacgatgagt                                   30

<210> SEQ ID NO 12
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 12
cgatctcgag ttaccgttcg tgcacgtacg                                   30

<210> SEQ ID NO 13
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 13
cgggatcccg cgataaacct gcgagggagt                                   30

<210> SEQ ID NO 14
<211> LENGTH: 30
<212> TYPE: DNA
<213> ORGANISM: Artificial Sequence
<220> FEATURE:
<223> OTHER INFORMATION: Primer for PCR multiplication

<400> SEQUENCE: 14
cgatctcgag gcgcacgcgc acgtaagtcc                                   30
```